United States Patent

US 9,000,050 B2

Wang et al.

(10) Patent No.: US 9,000,050 B2
(45) Date of Patent: Apr. 7, 2015

(54) SHIP1 MODULATORS AND RELATED METHODS

(75) Inventors: Xiaoxia Wang, Vancouver (CA); Labros George Meimetis, Vancouver (CA); Matthew Bruce Nodwell, Munich (DE); Raymond Andersen, Vancouver (CA)

(73) Assignee: The University of British Columbia, Vancouver, BC (CA)

( * ) Notice: Subject to any disclaimer, the term of this patent is extended or adjusted under 35 U.S.C. 154(b) by 0 days.

(21) Appl. No.: 13/817,106

(22) PCT Filed: Aug. 22, 2011

(86) PCT No.: PCT/US2011/048650
§ 371 (c)(1),
(2), (4) Date: May 6, 2013

(87) PCT Pub. No.: WO2012/024682
PCT Pub. Date: Feb. 23, 2012

(65) Prior Publication Data
US 2013/0217674 A1 Aug. 22, 2013

Related U.S. Application Data

(60) Provisional application No. 61/375,698, filed on Aug. 20, 2010.

(51) Int. Cl.
| | |
|---|---|
| A61K 31/045 | (2006.01) |
| A61K 31/015 | (2006.01) |
| C07C 43/23 | (2006.01) |
| C07C 215/44 | (2006.01) |
| C07C 251/44 | (2006.01) |
| C07D 223/32 | (2006.01) |
| C07C 69/65 | (2006.01) |
| C07C 39/17 | (2006.01) |
| C07C 49/747 | (2006.01) |
| C07C 49/753 | (2006.01) |
| C07C 37/50 | (2006.01) |
| C07C 41/18 | (2006.01) |
| C07C 45/30 | (2006.01) |
| C07C 45/65 | (2006.01) |
| C07C 67/08 | (2006.01) |
| C07C 69/734 | (2006.01) |
| C07C 213/02 | (2006.01) |
| C07C 215/64 | (2006.01) |
| C07C 249/08 | (2006.01) |

(52) U.S. Cl.
CPC .............. *C07C 43/23* (2013.01); *A61K 31/045* (2013.01); *C07C 215/44* (2013.01); *C07C 251/44* (2013.01); *C07D 223/32* (2013.01); *C07C 69/65* (2013.01); *C07C 39/17* (2013.01); *C07C 49/747* (2013.01); *C07C 49/753* (2013.01); *C07C 37/50* (2013.01); *C07C 41/18* (2013.01); *C07C 45/30* (2013.01); *C07C 45/65* (2013.01); *C07C 67/08* (2013.01); *C07C 69/734* (2013.01); *C07C 213/02* (2013.01); *C07C 215/64* (2013.01); *C07C 249/08* (2013.01); *C07B 2200/07* (2013.01); *C07C 2103/40* (2013.01)

(58) Field of Classification Search
USPC .......................................... 514/738, 764, 765
See application file for complete search history.

(56) References Cited

FOREIGN PATENT DOCUMENTS

| | | |
|---|---|---|
| WO | WO 03/033517 A1 | 4/2003 |
| WO | WO 2007/147251 A1 | 12/2007 |
| WO | WO 2007147251 A1 * | 12/2007 |

OTHER PUBLICATIONS

Liermann, J.C., et al. J. Nat. Prod. vol. 71 pp. 1654-1656. Published online Sep. 5, 2008.*
Liermann, J.C. et al (Journal of Natural Products vol. 71, pp. 1654-1646, published on line Sep. 5, 2008.*

(Continued)

*Primary Examiner* — Paul Zarek
*Assistant Examiner* — George W Kosturko
(74) *Attorney, Agent, or Firm* — Seed IP Law Group PLLC

(57) ABSTRACT

Compounds of structure (I): including stereoisomers and pharmaceutically acceptable salts thereof, wherein $R^1$, $R^2$ and A are as defined herein are disclosed. Such compounds have enhanced water solubility and have activity as SHIP1 modulators, and thus may be used to treat any of a variety of diseases, disorders or conditions that would benefit from SHIP1 modulation. Enantioselective methods for preparation of compounds of structure (I), compositions comprising a compound of structure (I) in combination with a pharmaceutically acceptable carrier or diluents and methods of SHIP1 modulation by administration of such compounds to an animal in need thereof are also disclosed.

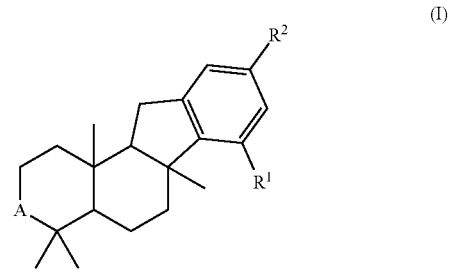

16 Claims, No Drawings

(56) References Cited

OTHER PUBLICATIONS

Abdel-Magid et al., "Reductive Amination of Aldehydes and Ketones with Sodium Triacetoxyborohydride. Studies on Direct and Indirect Reductive Amination Procedures," *J Org Chem* 61(11): 3849-3862, 1996.

Bryant et al., "Improved Hydroxylamine Method for the Determination of Aldehydes and Ketones. Displacement of Oxime Equilibria by Means of Pyridine," *J Am Chem Soc* 57: 52-61, 1935.

Dess et al., "A Useful 12-I-5 Triacetoxyperiodinane (the Dess-Martin Periodinane) for the Selective Oxidation of Primary or Secondary Alcohols and a Variety of Related 12-I-5 Species," *J Am Chem Soc* 113(19): 7277-7287, 1991.

Hayashi et al., "Remarkably Mild and Efficient Intramolecular Friedel-Crafts Cyclization Catalyzed by In(III)," *Organic Letters* 9(7): 1311-1314, 2007.

Kantorowski et al., "Expansion to Seven-Membered Rings," *Tetrahedron* 56: 4317-4353, 2000.

Wang et al., "Lipase-Catalyzed Irreversible Transesterifications Using Enol Esters as Acylating Reagents: Preparative Enantio—and Regioselective Syntheses of Alcohols, Glycerol Derivatives, Sugars, and Organometallics," *J Am Chem Soc* 110(21): 7200-7205, 1988.

Wong et al., "Organocatalytic Oxidation. Asymmetric Epoxidation of Olefins Catalyzed by Chiral Ketones and Iminium Salts," *Chem Rev* 108(9): 3958-3987, 2008.

\* cited by examiner

SHIP1 MODULATORS AND RELATED METHODS

CROSS-REFERENCE TO RELATED APPLICATIONS

This application claims the benefit under 35 U.S.C. §119 (e) of U.S. Provisional Patent Application No. 61/375,698 filed Aug. 20, 2010, where this provisional application is incorporated herein by reference in its entirety.

BACKGROUND

1. Technical Field

The present invention is generally directed to SHIP1 modulators, as well as to compositions and methods related to the same.

2. Description of the Related Art

In response to extracellular signals, phosphoinositide 3-kinase (PI3K) becomes activated and phosphorylates phosphatidylinositol-4,5-bisphosphate (PI-4,5-$P_2$) within the plasma membrane to generate phosphatidylinositol-3,4,5-trisphosphate ($PIP_3$). $PIP_3$ then initiates a cascade of downstream signaling pathways by interacting with pleckstrin homology (PH) domain-containing proteins, such as protein kinase B (PKB, also known as Akt), that regulate cellular activation, function, proliferation and/or survival, depending on the cell type and stimulus (Deane et al., *Annu Rev Immunol* 22, 563-598, 2004). Cellular levels of $PIP_3$ are normally tightly regulated by PI3K, the 5' inositol phosphatases SHIP1 (SH2 domain-containing inositol phosphatase), SHIP2 and by the 3' inositol phosphatase PTEN. SHIP1 and SHIP2 dephosphorylate $PIP_3$ to phosphatidylinositol-3,4-bisphosphate (PI-3,4-$P_2$), whereas PTEN dephosphorylates $PIP_3$ to PI-4,5-$P_2$ (Sly et al., *Exp Hematol* 31, 1170-1181, 2003; Vivanco et al., *Nat Rev Cancer* 2, 489-501, 2002). Of these, SHIP1 is unique in that its expression is restricted primarily to immune and hematopoietic cells (Sly et al., *Exp Hematol* 31, 1170-1181, 2003; Damen et al., *Proc Natl Acad Sci USA* 93, 1689-1693, 1996).

SHIP1's role in immune cell homeostasis is shown both by the myeloproliferative syndrome observed in SHIP1$^{-/-}$ mice, as well as the hypersensitivity of SHIP1$^{-/-}$ mice and cells to immune stimulation (Helgason et al., *Genes Dev* 12, 1610-1620, 1998; Sly et al., *Immunity* 21, 227-239, 2004). SHIP1 has been shown to mediate signaling from the inhibitory FcγRIIB receptor (Coggeshall et al., *Mol Immunol* 39, 521-529, 2002), and is important in terminating signal transduction from activating immune/hematopoietic cell receptor systems (Kalesnikoff et al., *Rev Physiol Biochem Pharmacol* 149, 87-103, 2003). Diminished SHIP1 activity or expression has also been observed in human inflammatory diseases (Vonakis et al., *J Allergy Clin Immunol* 108, 822-831, 2001) and hematopoietic malignancies (Liang et al., *Proteomics* 6, 4554-4564, 2006; Fukuda et al., *Proc Natl Acad Sci USA* 102, 15213-15218, 2005; Luo et al., *Zhongguo Shi Yan Xue Ye Xue Za Zhi* 12, 420-426, 2004; Vanderwinden et al., *Cell Signal* 18, 661-669, 2006).

Because dysregulated activation of the PI3K pathway contributes to inflammatory/immune disorders and cancer, intense efforts have been invested into the development of inhibitors of PI3K itself, as well as downstream protein kinases (Workman et al., *Nat Biotechnol* 24, 794-796, 2006; Simon, *Cell* 125, 647-649, 2006; Hennessy et al., *Nat Rev Drug Discov* 4, 988-1004, 2005; Knight et al., *Cell* 125, 733-747, 2006). The precedent for discovery and biologic efficacy of kinase inhibitors is well established, and a number of promising new PI3K isoform-specific inhibitors have recently been developed and used in mouse models of inflammatory disease (Camps et al., *Nat Med* 11, 936-943, 2005; Barber et al., *Nat Med* 11, 933-935, 2005) and glioma (Fan et al., *Cancer Cell* 9, 341-349, 2006) with minimal toxicities. However, because of the dynamic interplay between phosphatases and kinases in regulating biologic processes, inositol phosphatase activators represent a complementary, alternative approach to reduce cellular $PIP_3$ levels. Of the phosphoinositol phosphatases that degrade $PIP_3$, SHIP1 is a particularly ideal target for development of therapeutics for treating immune and hemopoietic disorders because its hematopoietic-restricted expression would limit the effects of a specific SHIP1 agonist to target cells.

To date, a number of small molecule SHIP1 modulators have been disclosed, including sesquiterpene compounds such as pelorol, which is a natural product isolated from the tropical marine sponge *Dactylospongia elegans* (Kwak et al., *J Nat Prod* 63, 1153-1156, 2000; Goclik et al., *J Nat Prod* 63, 1150-1152, 2000). Other reported SHIP1 modulators include the compounds set forth in Ong et al. *Blood* 110, 1942-1949, 2007; Kennah et al. *Experimental Hematology* 37, 1274-1283, 2009; Yang et al. *Org. Lett.* 7, 1073-1076, 2005; WO2003/033517, WO2004/035601, WO2007/147251 and WO2007/147252.

While significant efforts have been made in this field, there remains a need for effective small molecule SHIP1 modulators having enhanced water solubility. There is also a need for pharmaceutical compositions containing such compounds and methods for preparing such compounds as well as for methods relating to the use thereof to treat disorders or conditions that would benefit from SHIP1 modulation. The present invention fulfills these needs, and provides other related advantages.

BRIEF SUMMARY

In brief, this invention is generally directed to compounds having the following structure (I):

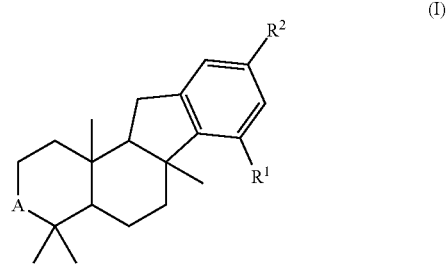

(I)

including stereoisomers and pharmaceutically acceptable salts thereof, wherein $R^1$, $R^2$ and A are as defined below.

Compounds of structure (I) have activity as SHIP1 modulators and utility over a wide range of therapeutic applications, and may be used to treat any of a variety of disorders or conditions that would benefit from SHIP1 modulation. For example, such disorders or conditions include (but are not limited to) autoimmune diseases such as idiopathic pulmonary fibrosis, inflammatory bowel disease (including Crohn's Disease and ulcerative colitis), rheumatoid arthritis, Still's Disease, Sjögren's Syndrome, systemic lupus erythematosus, and systemic sclerosis; inflammatory diseases such as allergic rhinitis, Alzheimer's Disease, asthma, ocular inflammatory diseases (including allergic conjunctivitis, dry eye, and uveitis), chronic obstructive pulmonary disease, eczema, post operative inflammation, multiple sclerosis, psoriasis, seronegative spondyloarthropathies (including anklyosing spondylitis, psoriatic arthritis, and Reiter's Syndrome), and vasculitis (including Wegener's Granulomatosis, polyarteritis nodosa, leucocytoclastic vasculitis, Churg-Strauss Syndrome, cryoglobulinemic vasculitis and giant cell arteritis); and neoplastic diseases or other cell proliferative disorders such as acute myelogenous leukemia, chronic myelogenous leukemia, acute lymphocytic leukemia, chronic lymphocytic leukemia, basophilic leukemia, cutaneous T-cell lymphoma, Sezary Syndrome, Hodgkin's Disease, Non-Hodgkin's Lymphoma, multiple myeloma, hypereosinophilic syndromes, mastocytosis and thrombocythemia.

In addition to having activity as SHIP1 modulators, compounds of structure (I) also show enhanced water solubility compared to other known SHIP1 modulators. Accordingly, in one embodiment of this invention SHIP1 modulators having increased water solubility compared to other reported SHIP1 modulators are provided.

Methods of this invention include enantioselective synthesis of compounds of structure (I). Accordingly, in another embodiment a method for the preparation of compounds of structure (I) using enantioselective catalysts are disclosed.

Methods of this invention include administering an effective amount of a compound of structure (I), typically in the form of a pharmaceutical composition, to an animal in need thereof, including a mammal (such as a human). Accordingly, in another embodiment, pharmaceutical compositions are disclosed containing one or more compounds of structure (I) in combination with a pharmaceutically acceptable carrier and/or diluent.

These and other aspects of the invention will be apparent upon reference to the following detailed description. To this end, various references are set forth herein which describe in more detail certain background information, procedures, compounds and/or compositions, and are each hereby incorporated by reference in their entirety.

DETAILED DESCRIPTION

As mentioned above, this invention is generally directed to small molecule modulators of SHIP1, as well as to corresponding compositions and methods of use. As used herein, a SHIP1 modulator can serve as either an agonist or antagonist of SHIP1.

In one embodiment, compounds are disclosed having the following structure (I):

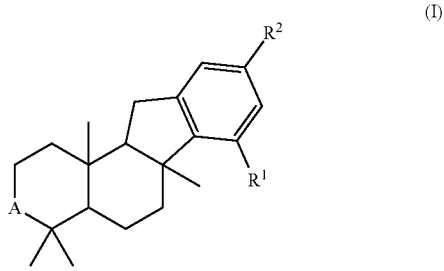

(I)

or a pharmaceutically acceptable salt or stereoisomer thereof, wherein $R^1$ and $R^2$ are each independently hydrogen, hydroxyl, alkyl or alkoxy, provided that at least one of $R^1$ and $R^2$ is hydroxyl or alkoxy;

A is —CHR$^3$—, —C(R$^4$)(R$^5$)NR$^6$—, —NR$^6$C(R$^4$)(R$^5$)—, —C(=O)— or —C(=N—OR$^6$)—;

$R^3$ is —OR$^6$, —OC(=O)R$^6$ or —NR$^6$R$^7$;

$R^4$ and $R^5$ are each hydrogen or both of $R^4$ and $R^5$ may be taken together to form an oxo moiety; and $R^6$ and $R^7$ are, at each occurrence, independently hydrogen, alkyl, optionally substituted aryl or optionally substituted aralkyl.

As used herein, the following terms have the meanings set forth below.

"Alkyl" means a straight chain or branched, noncyclic or cyclic, unsaturated or saturated aliphatic hydrocarbon containing from 1 to 10 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like. Cyclic alkyls are also referred to herein as "homocycles" or "homocyclic rings." Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

"Aryl" means an aromatic cyclic alkyl, such as phenyl and naphthyl.

"Aralkyl" means an alkyl having at least one alkyl hydrogen atom replaced with an aryl moiety, such as —CH$_2$-phenyl, and the like.

An "optionally substituted" aryl or aralkyl means an aryl or aralkyl, moiety as defined above wherein 1 to 4 hydrogen atoms of the aryl or aralkyl moiety are replaced with a substituent. In the case of an oxo substituent ("=O") two hydrogen atoms are replaced. When substituted, "substituents" within the context of this invention include oxo, halogen, hydroxyl, alkoxy, and alkyl.

"Alkoxy" means an alkyl moiety attached through an oxygen bridge (i.e., —O-alkyl), such as methoxy, ethoxy, and the like.

"Hydroxyl" means —OH.

"Halogen" means fluoro, chloro, bromo and iodo.

As noted above, one embodiment of the present invention is a compound of structure (I):

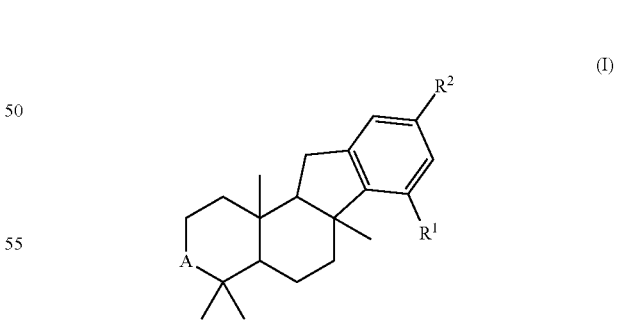

(I)

or a pharmaceutically acceptable salt or stereoisomer thereof, wherein $R^1$ and $R^2$ are each independently hydrogen, hydroxyl, alkyl or alkoxy, provided that at least one of $R^1$ and $R^2$ is hydroxyl or alkoxy;

A is —CHR$^3$—, —C(R$^4$)(R$^5$)NR$^6$—, —NR$^6$C(R$^4$)(R$^5$)—, —C(=O)— or —C(=N—OR$^6$)—;

$R^3$ is —OR$^6$, —OC(=O)R$^6$ or —NR$^6$R$^7$;

$R^4$ and $R^5$ are each hydrogen or both of $R^4$ and $R^5$ may be taken together to form an oxo moiety; and $R^6$ and $R^7$ are, at each occurrence, independently hydrogen, alkyl, optionally substituted aryl or optionally substituted aralkyl.

In another embodiment, $R^1$ and $R^2$ are each methoxy and the compound has the following structure (II):

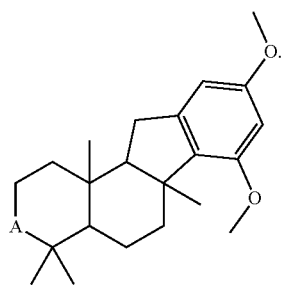

(II)

In another embodiment, $R^1$ and $R^2$ are each hydroxyl and the compound has the following structure (I11):

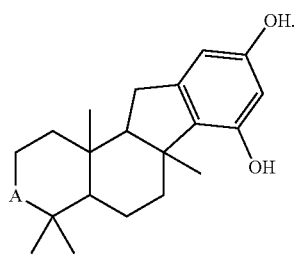

(III)

In yet other embodiments, A is —$CHR^3$—, and the compound has the following structure (IV):

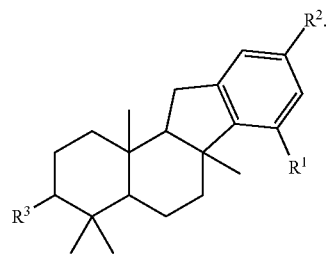

(IV)

In other embodiments of structure (IV), the compound has one of the following structures (IV-1) or (IV-2):

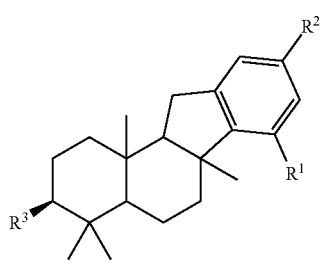

(IV-1)

or

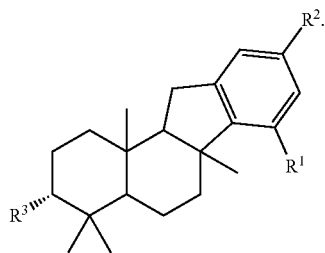

(IV-2)

In other embodiments, the compound has one of the following structures (IV-3), (IV-4) or (IV-5):

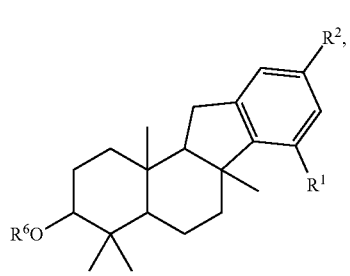

(IV-3)

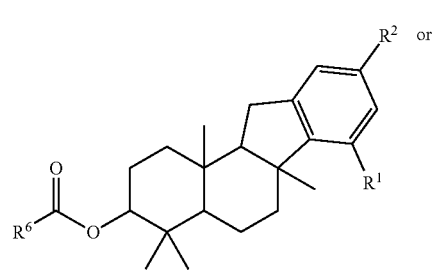

(IV-4) or

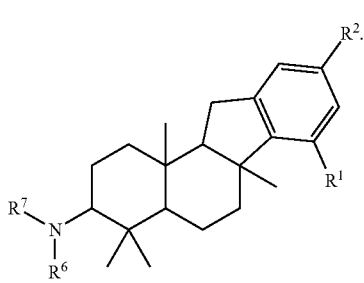

(IV-5)

In yet other embodiments of structure (IV), the compound has one of the following structures (IV-6), (IV-7), (IV-8), (IV-9), (IV-10), (IV-11), (IV-12), (IV-13), (IV-14), (IV-15), (IV-16), (IV-17), (IV-18), (IV-19) or (IV-20):

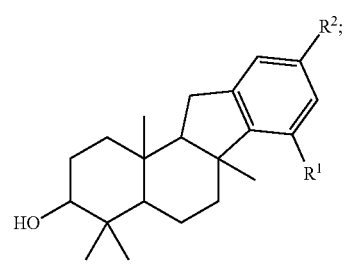

(IV-6)

(IV-7)
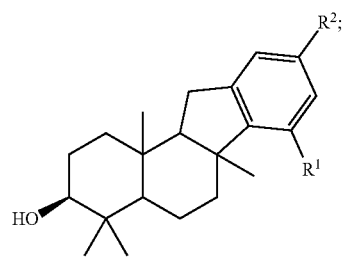
(IV-8)
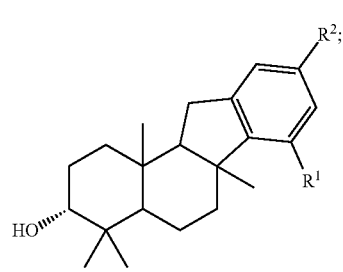
(IV-9)
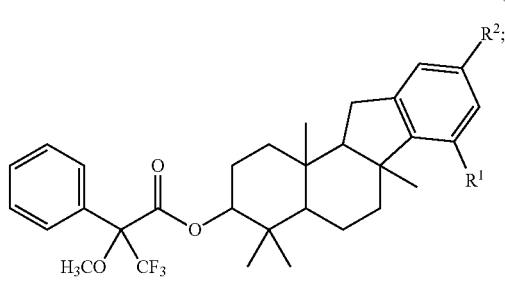
(IV-10)
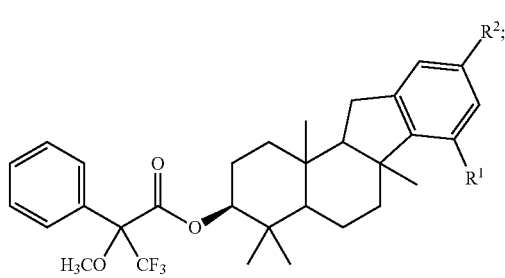
(IV-11)
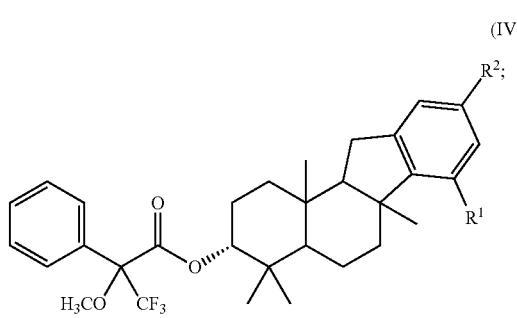
(IV-12)
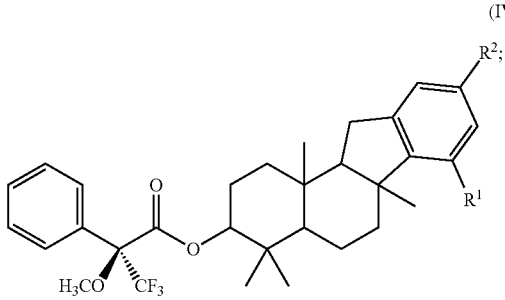
(IV-13)
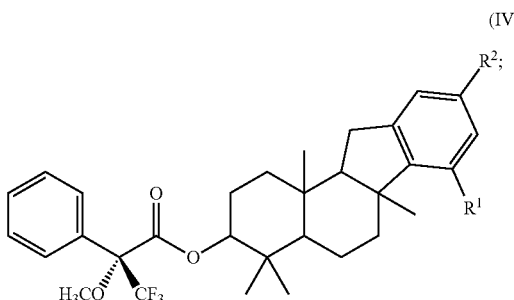
(IV-14)
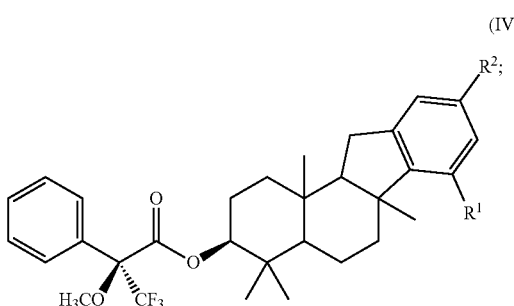
(IV-15)
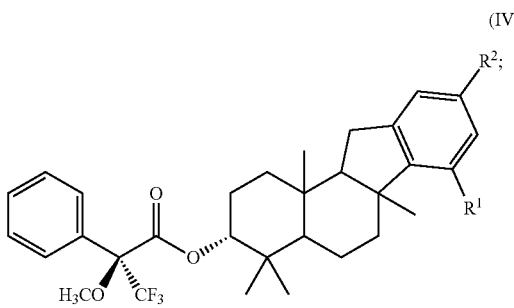
(IV-16)
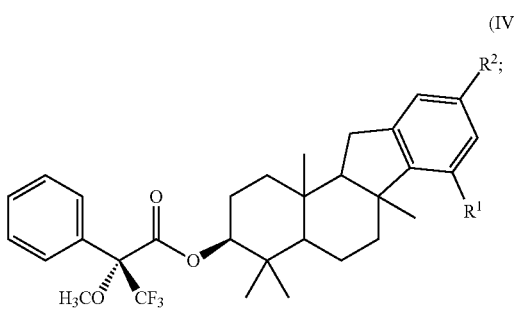

(IV-17)
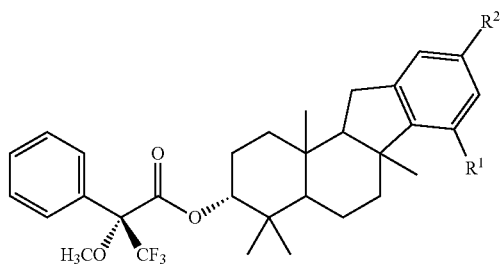

(IV-18)
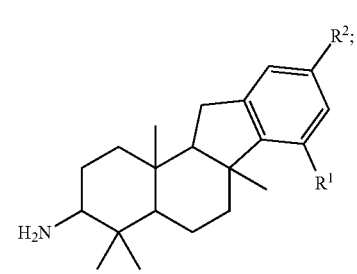

(IV-19)
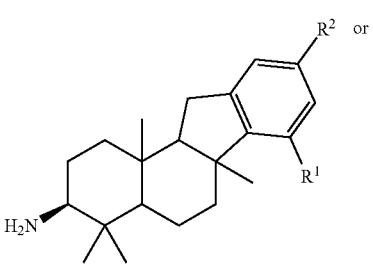

(IV-20)
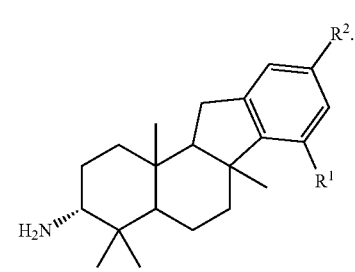

In other embodiments, A is —C(R⁴)(R⁵)NR⁶—, and the compound has the following structure (V):

(V)
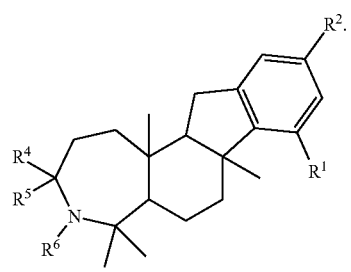

In other embodiments of structure (V), the compound has one of the following structures (V-1) or (V-2):

(V-1)
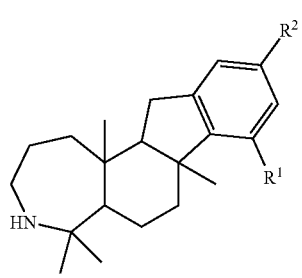

or (V-2)
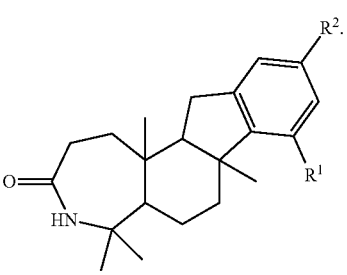

In other embodiments, A is —NR⁶C(R⁴)(R⁵)—, and the compound has the following structure (VI):

(VI)
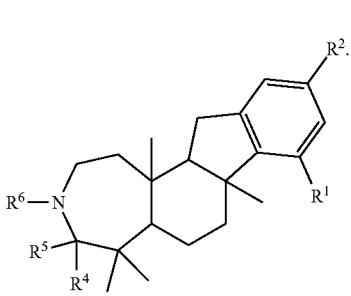

In other embodiments of structure (VI), the compound has one of the following structures (VI-1) or (VI-2):

(VI-1)
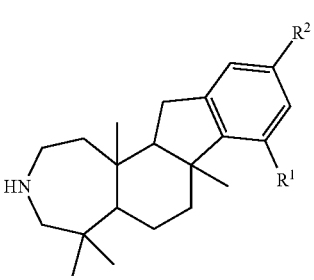

or (VI-2)
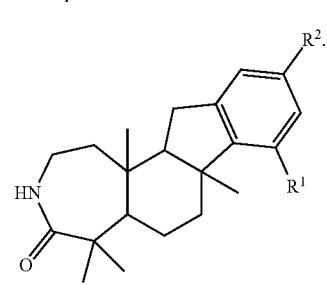

In yet other embodiments, A is —C(=O)—, and the compound has the following structure (VII):

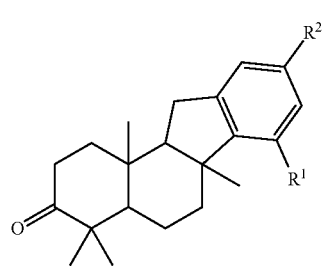
(VII)

In other embodiments, A is —C(=N—OR$^6$)—, and the compound has the following structure (VIII):

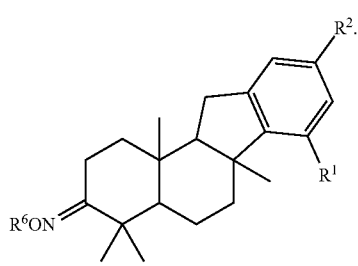
(VIII)

In other embodiments of structure (VIII), the compound has the following structure (VIII-1):

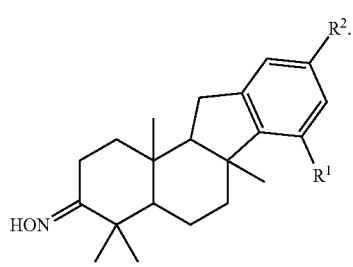
(VIII-1)

In other embodiments, the compound has one of the following structures (IX) or (X):

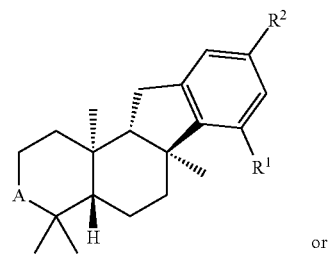
(IX)

or

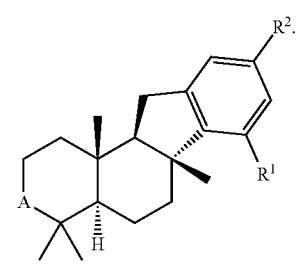
(X)

In other embodiments, R$^1$ is methyl and R$^2$ is methoxy or R$^2$ is hydroxyl and the compound has one of the following structures (XI) or (XII):

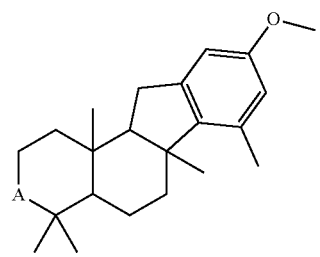
(XI)

or

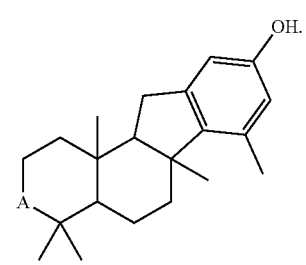
(XII)

In another embodiment of the present invention a compound is provided, the compound being selected from the group consisting of:

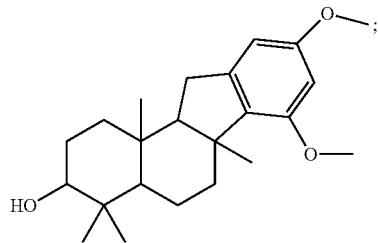

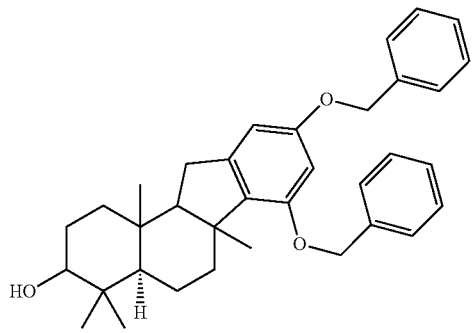

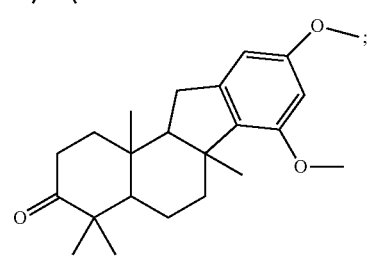

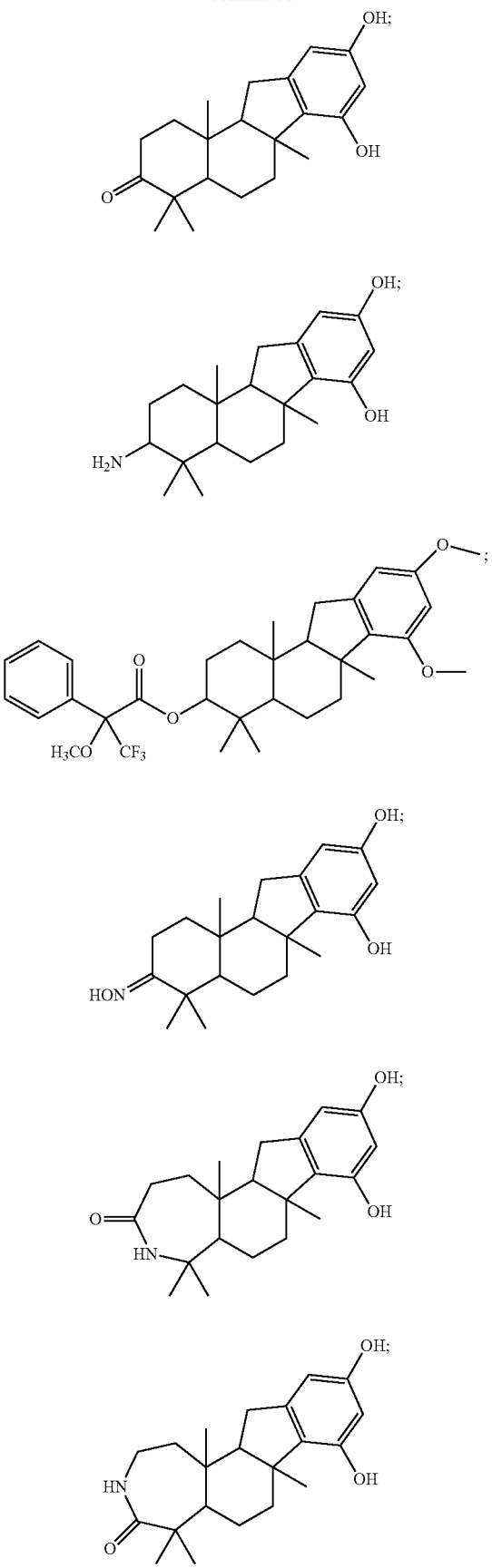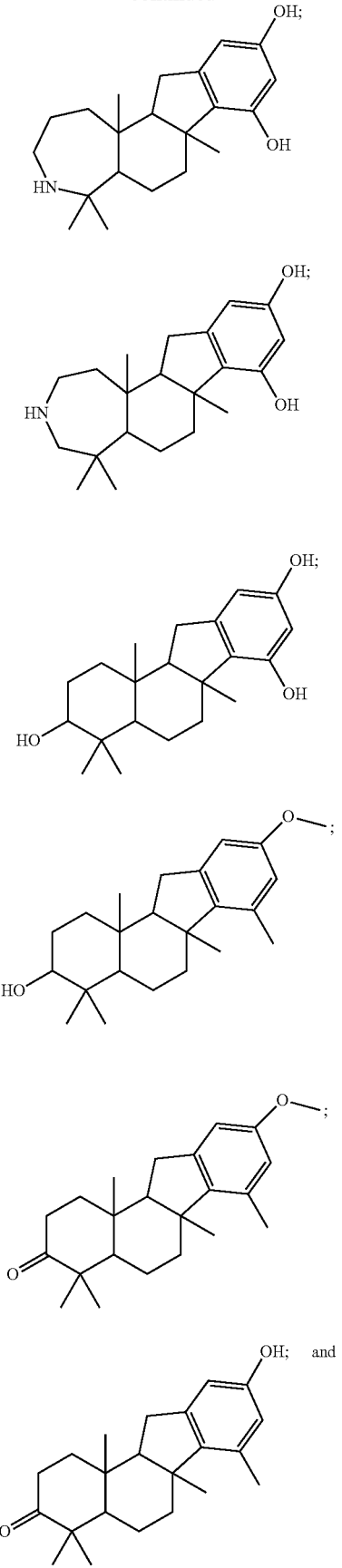

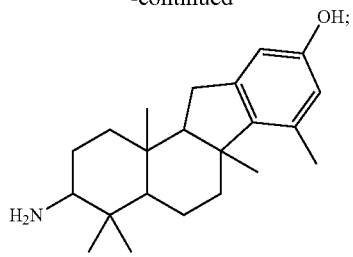
or a pharmaceutically acceptable salt or stereoisomer thereof.
In other embodiments the compound is selected from the group consisting of:
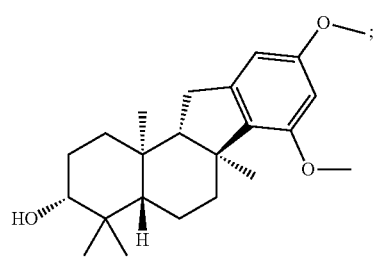
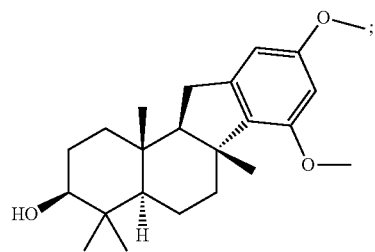
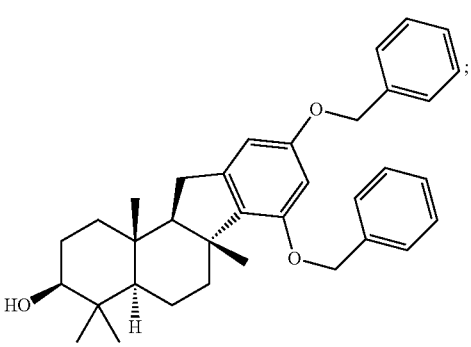
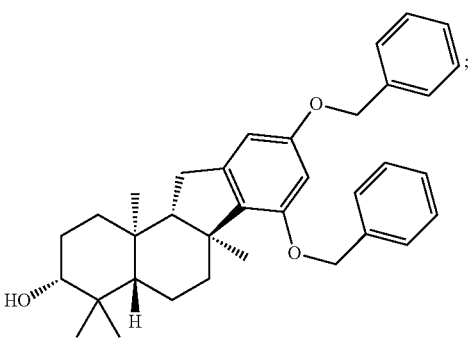
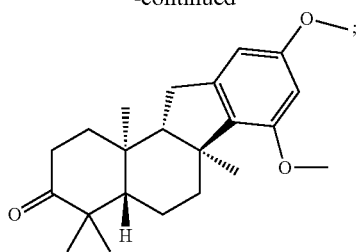
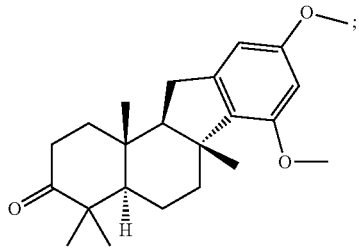
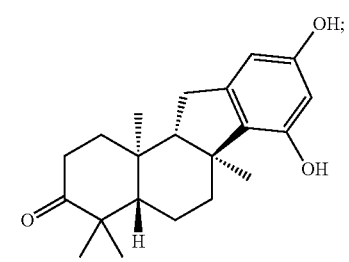
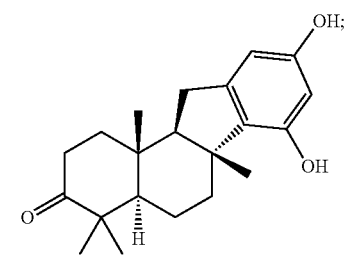
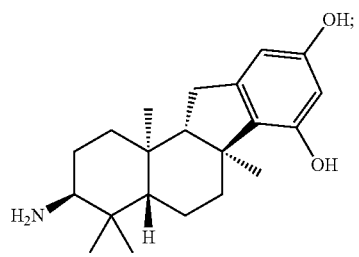
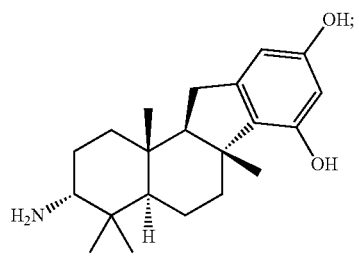

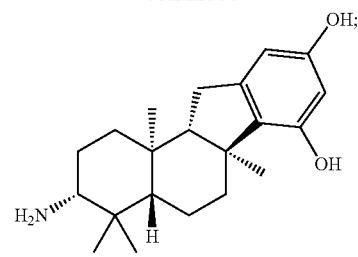
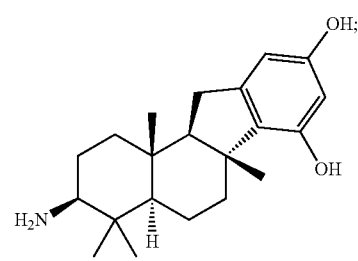
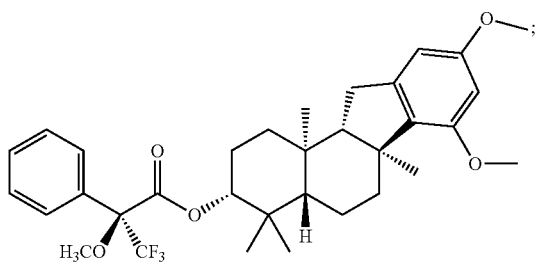
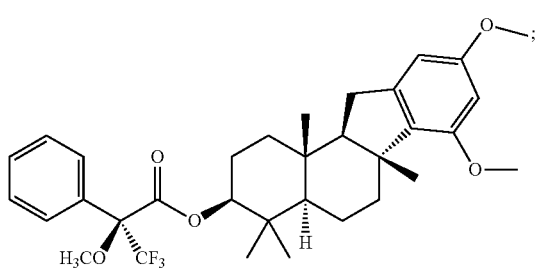
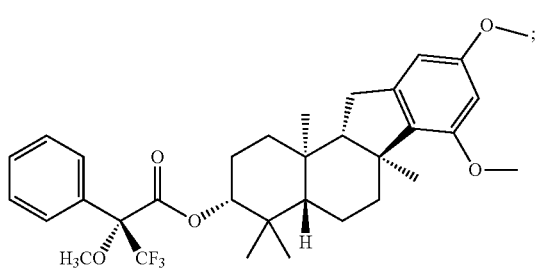
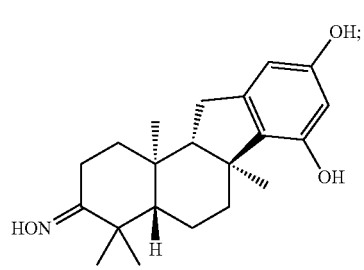
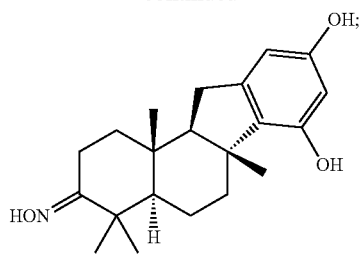
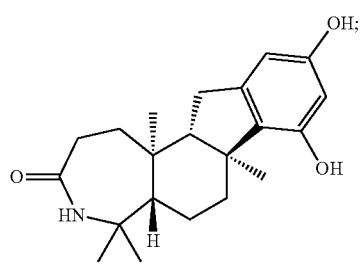
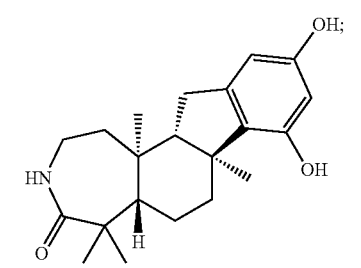
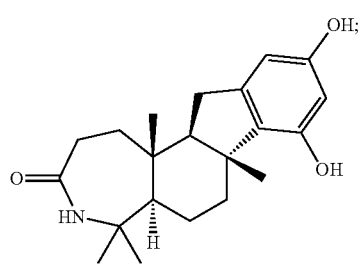
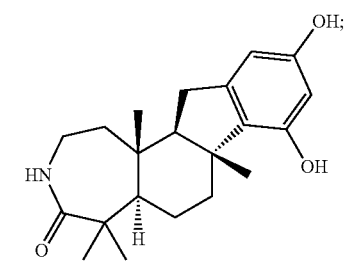
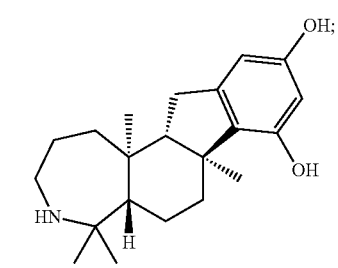

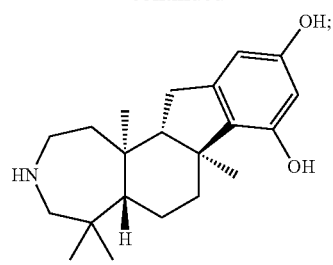
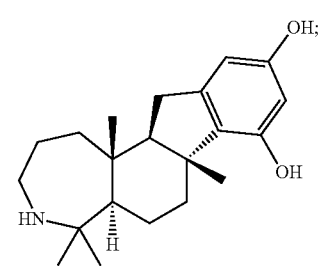
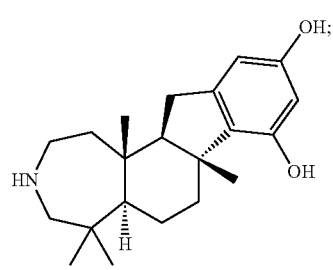
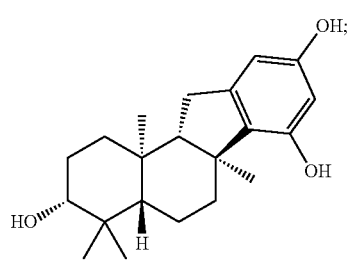
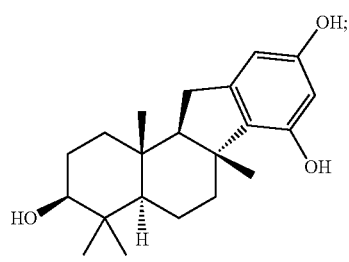
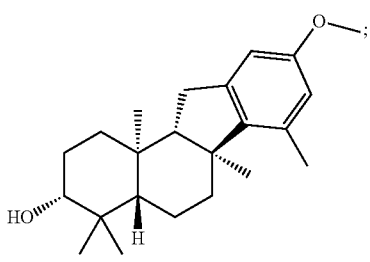
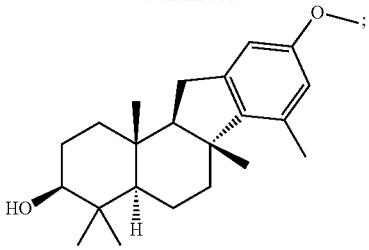
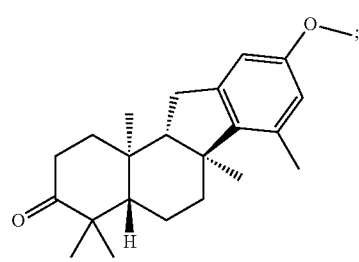
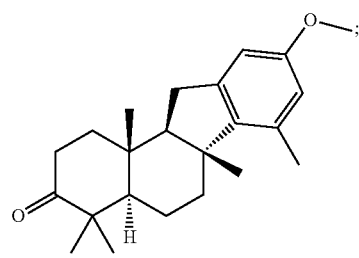
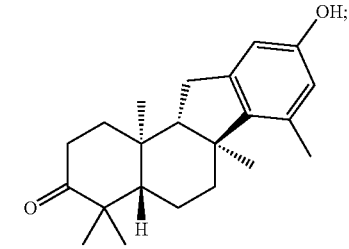
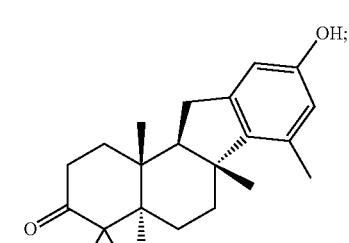
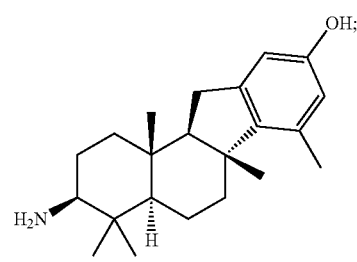

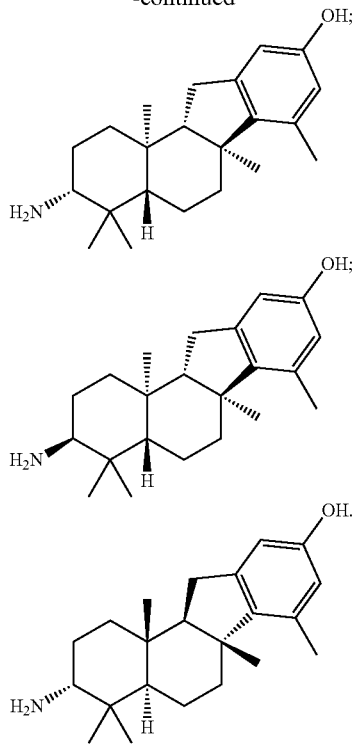

or a pharmaceutically acceptable salt or stereoisomer thereof.

In another embodiment, the present invention provides a composition comprising any of the foregoing compounds in combination with a pharmaceutically acceptable carrier or diluent.

Another embodiment of the present invention is a method for modulating SHIP1, the method comprises administering an effective amount of a composition comprising any of the foregoing compounds to an animal in need thereof.

In another embodiment, the present invention provides a method for treating a disease, disorder or condition comprising administering an effective amount of a composition comprising any of the foregoing compounds to an animal in need thereof, where the disease, disorder or condition is an autoimmune disease, disorder or condition, an inflammatory disease, disorder or condition, or a neoplastic or cell proliferative disease, disorder or condition.

For example, in some embodiments the disease, disorder or condition is an autoimmune disease, disorder or condition selected from idiopathic pulmonary fibrosis, an inflammatory bowel disease, rheumatoid arthritis, Still's Disease, Sjögren's Syndrome, systemic lupus erythematosus, and systemic sclerosis.

In some further embodiments, the disease, disorder or condition is an inflammatory bowel disease selected from Crohn's Disease and ulcerative colitis. While in other further embodiments, the disease, disorder or condition is an inflammatory disease, disorder or condition selected from allergic rhinitis, Alzheimer's Disease, asthma, an ocular inflammatory disease, chronic obstructive pulmonary disease, eczema, post operative inflammation, multiple sclerosis, psoriasis, a seronegative spondyloarthropathy, and vasculitis.

In other further exemplary embodiments, the disease, disorder or condition is an ocular inflammatory disease selected from allergic conjunctivitis, dry eye, and uveitis. In yet other further embodiments, the disease, disorder or condition is a seronegative spondyloarthropathy selected from anklyosing spondylitis, psoriatic arthritis, and Reiter's Syndrome, and in other further embodiments, the disease, disorder or condition is vasculitis selected from Wegener's Granulomatosis, polyarteritis nodosa, leucocytoclastic vasculitis, Churg-Strauss Syndrome, cryoglobulinemic vasculitis, and giant cell arteritis.

In some other embodiments, the disease, disorder or condition is a neoplastic or cell proliferative disease, disorder or condition selected from acute myelogenous leukemia, chronic myelogenous leukemia, acute lymphocytic leukemia, chronic lymphocytic leukemia, basophilic leukemia, cutaneous T-cell lymphoma, Sezary Syndrome, Hodgkin's Disease, Non-Hodgkin's Lymphoma, multiple myeloma, hypereosinophilic syndromes, mastocytosis and thrombocythemia The compounds of the present invention may be prepared by known organic synthesis techniques, including the methods described in more detail in the Examples. In general, the compounds of structure (I) may be made by the following General Schemes (Schemes A to D), wherein all substituents are as defined above unless indicated otherwise. Although not generally depicted in the following schemes, one skilled in the art will understand that appropriate protecting group strategies may be useful in preparing compounds of structure (I). For example, methoxy and/or benzyl groups may be used to protect hydroxyl groups. Methoxy groups can be removed by treatment with boron tribromide in dichloromethane, and benzyl groups may be removed under catalytic hydrogenation conditions. This, and other protecting group methodology, is well known to those skilled in the art (see, for example, PROTECTIVE GROUPS IN ORGANIC SYNTHESIS, Green, T. W. et. al., Wiley-Interscience, New York City, 1999).

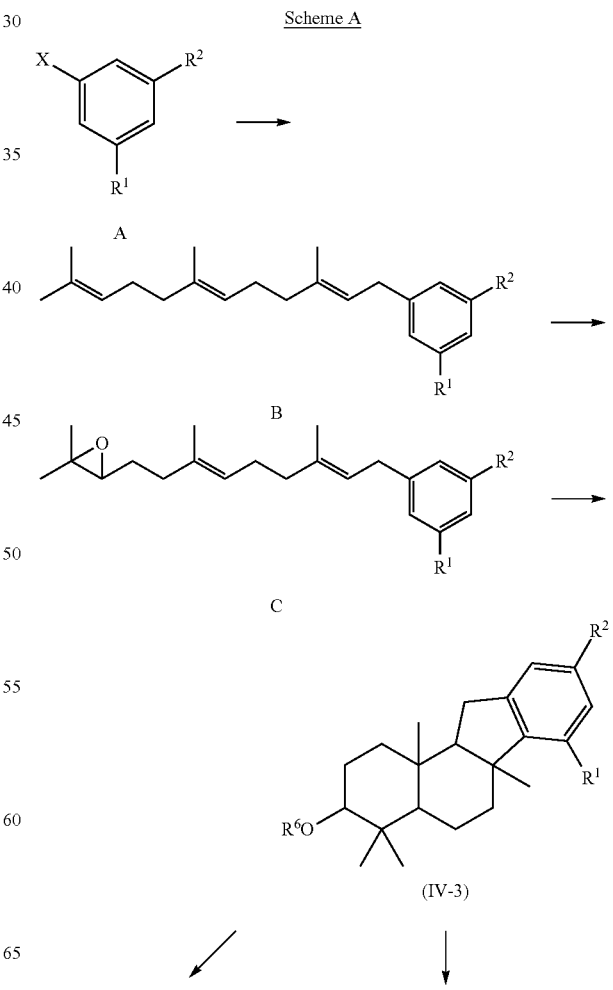

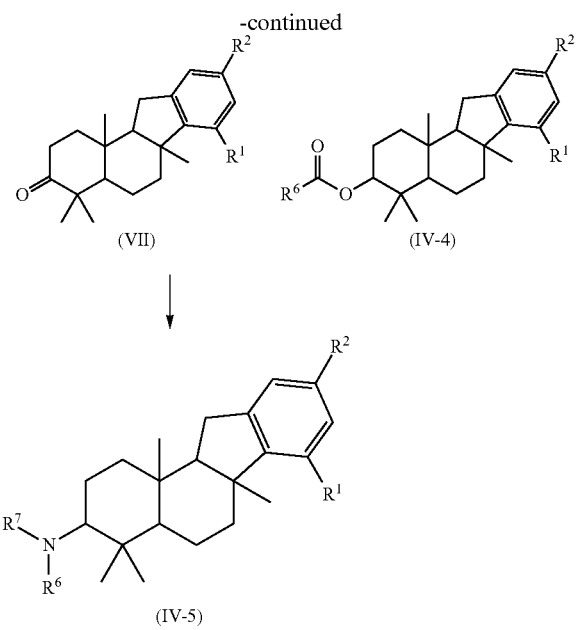

Exemplary compounds of structure (IV) (i.e., where A is —CHR³—) and structure (VII) (i.e., where A is —C(=O)—) may be prepared according to Scheme A. For example, compound A, where X is halogen, may be purchased or prepared according to methods known in the art and used to prepare an appropriate aryl cuprate, for example by treatment of A with n-butyl lithium followed by Li₂CuCl₄. The aryl cuprate can then be coupled with an appropriate allyl bromide, for example trans,trans-farnesyl bromide, to produce the aromatic allyl compound B. Epoxidation of compound B using appropriate methods, for example, conditions adapted from the published procedure (method C) from *J. Am. Chem. Soc.*, 1997, 119(46), 11224-11235, results in epoxide C. For exemplary purposes, epoxide C is depicted in Scheme A without stereochemistry, however epoxide C can be a racemic mixture, enantiomerically pure or enantiomerically enriched depending on the method of preparation. For example, in one embodiment of the present invention, a method for epoxidation of compound B under enantioselective conditions to yield enantiomerically pure or enantiomerically enriched compounds of structure C is provided. Such methods comprise the use of an enantioselective catalyst. For example, in some embodiments the enantioselective catalyst comprises (3aR,4'S,7aR)-2,2,2',2'-tetramethyldihydrospiro[[1,3]dioxolo[4,5-c]pyran-6,4'-[1,3]dioxolan]-7(7aH)-one or (3aS,4'R,7aS)-2,2,2',2'-tetramethyldihydrospiro[[1,3]dioxolo[4,5-c]pyran-6,4'-[1,3]dioxolan]-7(7aH)-one as described in more detail in the Examples.

Opening of the epoxide and subsequent cyclization of C under appropriate conditions, for example, by treatment with indium bromide, results in compounds of structure (IV-3), where R⁶ is H, and various tricyclic impurities.

After separation from the various tricyclic impurities, compounds of structure (IV-3) can be oxidized under appropriate conditions, for example, an excess of Dess-Martin periodinane (DMP) in dichloromethane (DCM) to yield compounds of structure (VII). Compounds of structure (VII) can then be reductively aminated using appropriate methods, for example, sodium cyanoborohydride treatment followed by treatment with ammonium acetate, to result in compounds of structure (IV-5). Generally, compounds of structure (IV-5) will be prepared as mixture of stereoisomers (at the carbon connecting —NR⁶R⁷ to the ring). Such mixtures can be separated using methods known to those skilled in the art. Alternatively, stereospecific preparation methods may be employed.

Alternatively, compounds of structure (IV-4) can be prepared by treatment of compounds of structure (IV-3), wherein R⁶ is H, with an appropriate acylating reagent, for example an appropriately substituted acid chloride, anhydride or other activated carbonyl compound.

Scheme B

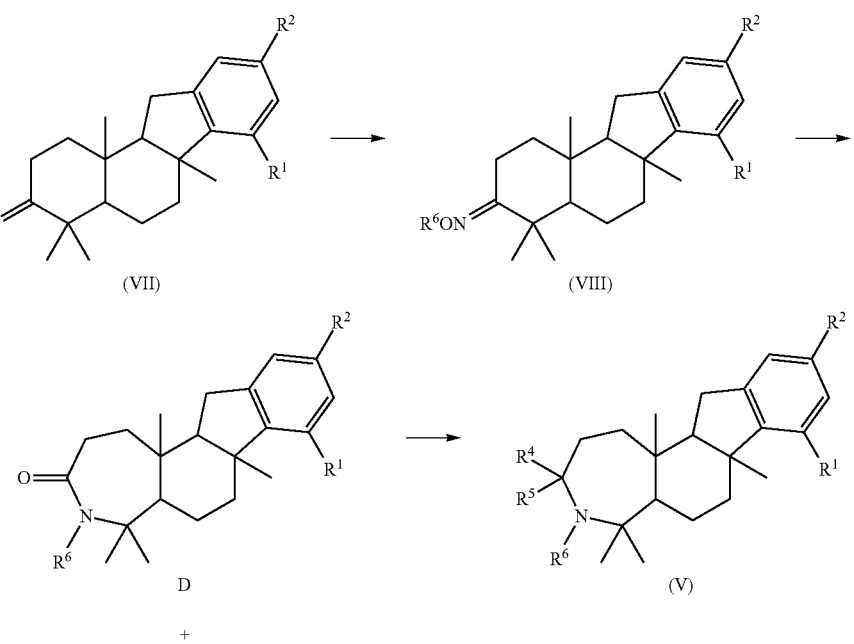

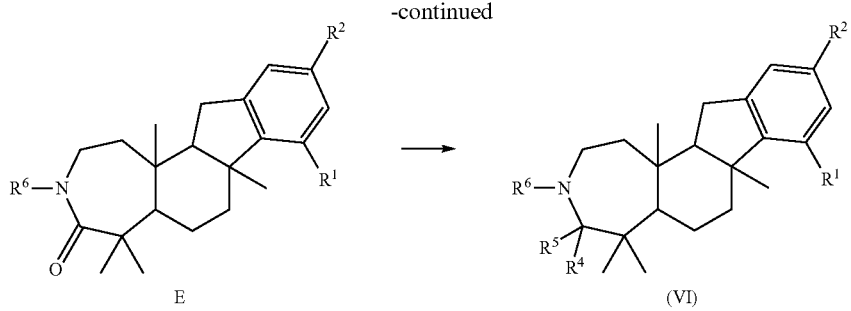

Other exemplary compounds of structure (I), wherein A is —C(R⁴)(R⁵)NR⁶—, —NR⁶C(R⁴)(R⁵)—, or —C(=N—OR⁶)—, may be prepared according to Scheme B. For example, compounds of structure (VII), which can be synthesized as described in Scheme A, can be treated with hydroxylamine, or an alkylated or arylated derivative thereof, to yield compounds of structure (VIII). Compounds of structure (VIII) can undergo a ring expansion, under appropriate conditions, for example, with trifluoroacetic anhydride, to produce regioisomers D and E (i.e., compounds of structure (I), wherein A is —C(R⁴)(R⁵)NR⁶— or —NR⁶C(R⁴)(R⁵)—, respectively, and wherein R⁴ and R⁵ are taken together to form an oxo moiety). Compounds D or E can be reduced under appropriate conditions, for example, by treatment with lithium aluminum hydride in THF, to provide compounds of structure (V) or (VI) wherein R⁴ and R⁵ are hydrogen.

Although depicted without stereochemistry, one skilled in the art will recognize that the compounds depicted in Schemes A and B can also be prepared in an optically pure form by utilizing the methods described in the description of Schemes A and B in combination with the methods for preparation of the tetracyclic core described in Schemes C and D below.

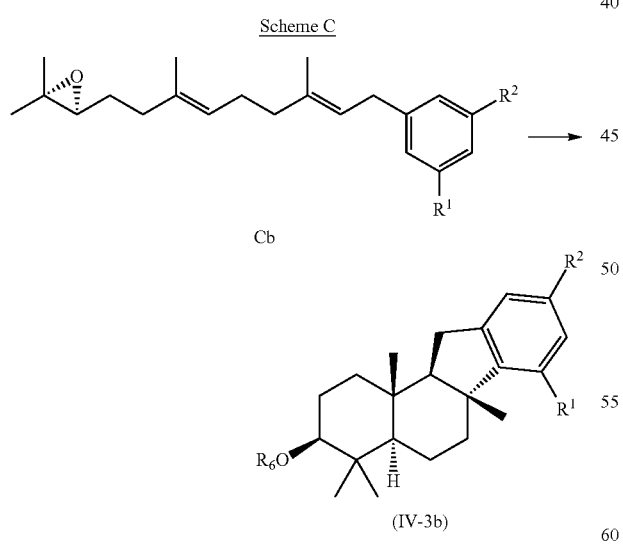

In reference to Scheme C, exemplary compounds of structure (I) may be prepared utilizing enantioselective methods for making enantiomerically pure epoxide Cb. For example, chiral epoxide Cb can be synthesized by the method described in Scheme A utilizing an appropriate chiral catalyst. Cyclization of Cb under the appropriate conditions, for example, by treatment with indium bromide, results in compounds of structure (IV-3b) and various tricyclic impurities. After separating the impurities from the mixture, (IV-3b) can be employed as starting material to prepare other compounds of structure (I) by utilizing the methods described in Schemes A and B.

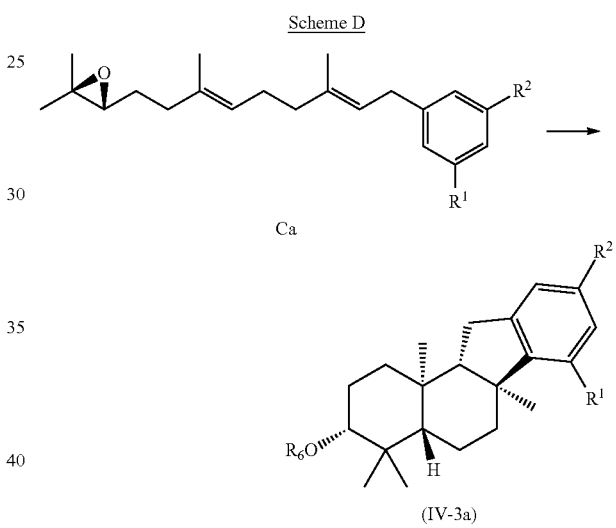

Referring to Scheme D, exemplary compounds of structure (I) may be prepared enantioselectively when methods for making an enantiomerically pure epoxide Ca are utilized. For example, chiral epoxide Ca can be synthesized by the method described in Scheme A by utilizing an appropriate chiral catalyst. Cyclization of Ca under the appropriate conditions, for example, by treatment with indium bromide, results in compounds of structure (IV-3a) and various tricyclic impurities. After separating the impurities from the mixture, compounds of structure (IV-3a) can be used as starting material to prepare other compounds of structure (I) by utilizing the methods described in reference to Schemes A and B.

In certain embodiments of the above methods (i.e., Schemes A-D), one or both of R¹ and R² may be alkoxy. In these embodiments, treatment with an appropriate deprotection reagent, for example boron tribromide in dichloromethane, results in compounds of structure (I) wherein one or both of R¹ and R² are hydroxyl.

In another embodiment, the present invention provides a method for enantioselective preparation of any of the foregoing compounds (i.e., compounds of structure (I)). The method comprises the step of cyclizing an epoxide of structure C to obtain a compound of structure (IV-3):

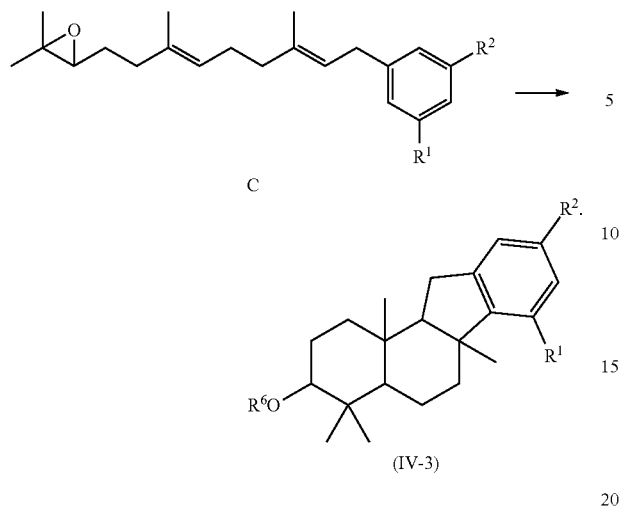

(IV-3)

In some further embodiments, cyclizing the epoxide of structure C comprises reacting the epoxide of structure C with indium bromide.

In other embodiments, the epoxide of structure C has been prepared by oxidizing a compound of structure B in the presence of a chiral catalyst according to the following scheme:

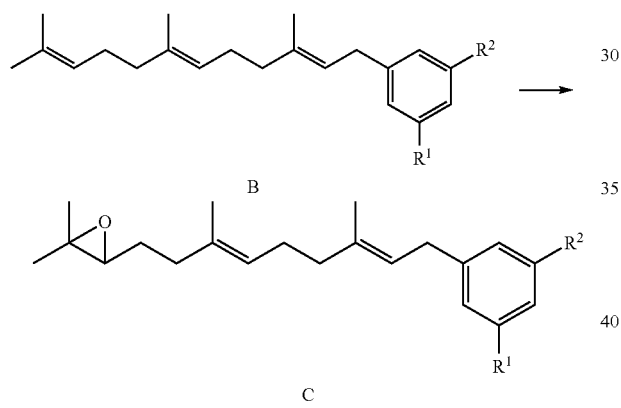

In some other embodiments, the epoxide of structure C has one of the following structures Ca or Cb:

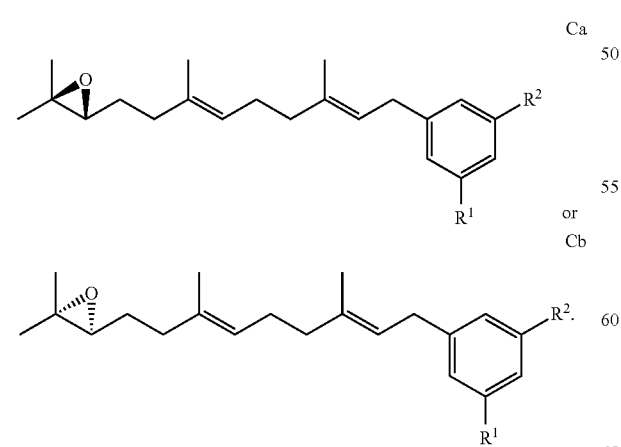

In some other embodiments, the chiral catalyst has one of the following structures 3a or 3b:

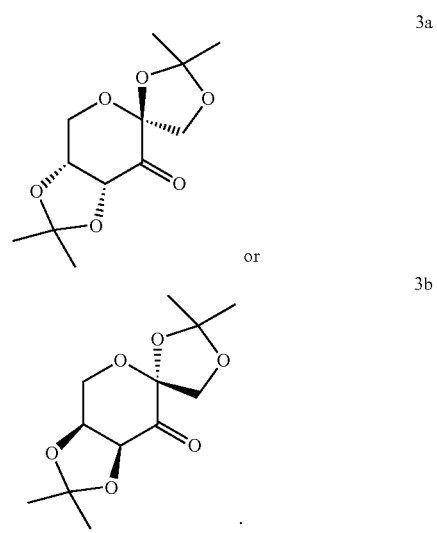

In some other embodiments, oxidizing the compound of structure B comprises treating the compound of structure B with an oxidation reagent. For example, in some embodiments the oxidation reagent comprises a peroxomonosulfate salt.

In some other embodiments, the method further comprises converting the compound of structure (IV-3) to a compound of structure (VII):

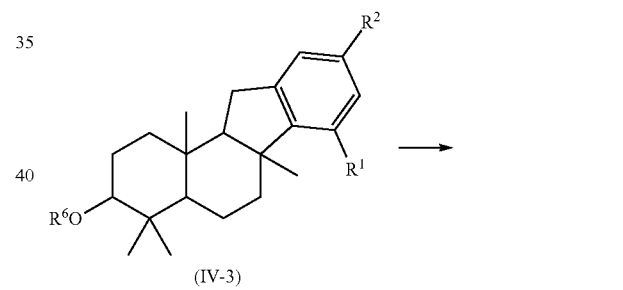

wherein the compound of structure (IV-3) has been prepared according to a method disclosed herein.

In some other embodiments, converting the compound of structure (IV-3) to a compound of structure (VII) comprises reacting the compound of structure (IV-3) with an oxidizing reagent. For example, in some embodiments, the oxidizing reagent is Dess-Martin periodinane.

In other embodiments, the method further comprises converting the compound of structure (VII) to a compound of structure (IV-5):

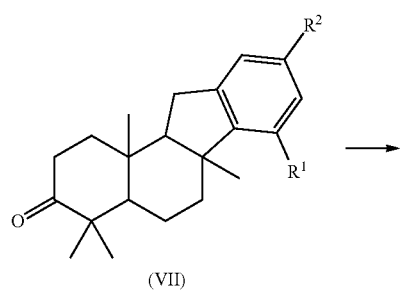

(VII)

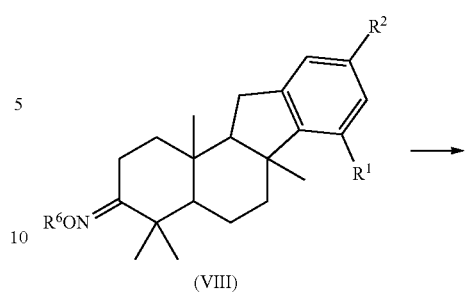

(VIII)

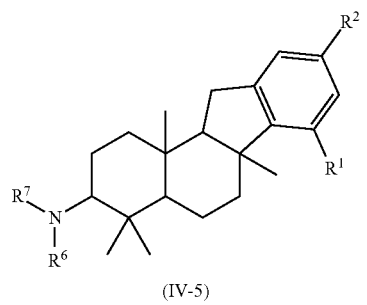

(IV-5)

wherein the compound of structure (VII) has been prepared according to a method disclosed herein.

In yet other embodiments, converting the compound of structure (VII) to a compound of structure (IV-5) comprises reductive amination of the compound of structure (VII). For example, in some embodiments reductive amination comprises treating the compound of structure (VII) with NaBH$_3$CN and NH$_4$OAc.

In some other embodiments, the method further comprises converting the compound of structure (VII) to a compound of structure (VIII):

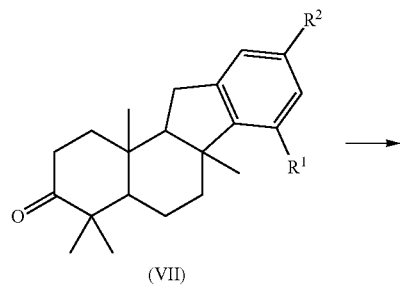

(VII)

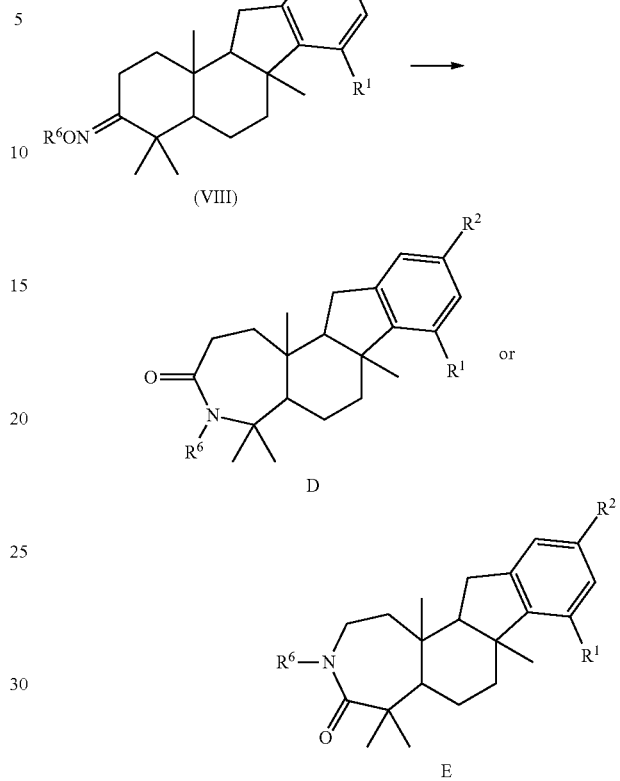

D or E wherein the compound of structure (VIII) has been prepared according to a method disclosed herein.

In some other embodiments, converting the compound of structure (VIII) to a compound of structure D or E comprises treating the compound of structure (VIII) with an alcohol activating reagent. For example, in some embodiments the alcohol activating reagent is trifluoroacetic anhydride.

In yet other embodiments, the method further comprises converting the compound of structure D or E to a compound of structure (V) or (VI), respectively:

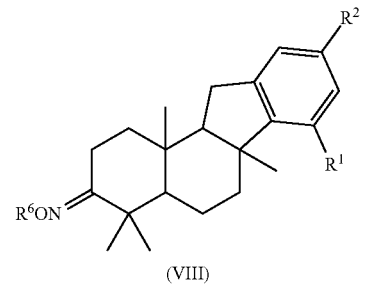

(VIII)

wherein the compound of structure (VII) has been prepared according to a method disclosed herein.

In some embodiments, converting the compound of structure (VII) to a compound of structure (VIII) comprises reacting the compound of structure (VII) with hydroxylamine or an alkylated derivative thereof.

In yet other embodiments, the method further comprises converting the compound of structure (VIII) to a compound of structure D or E:

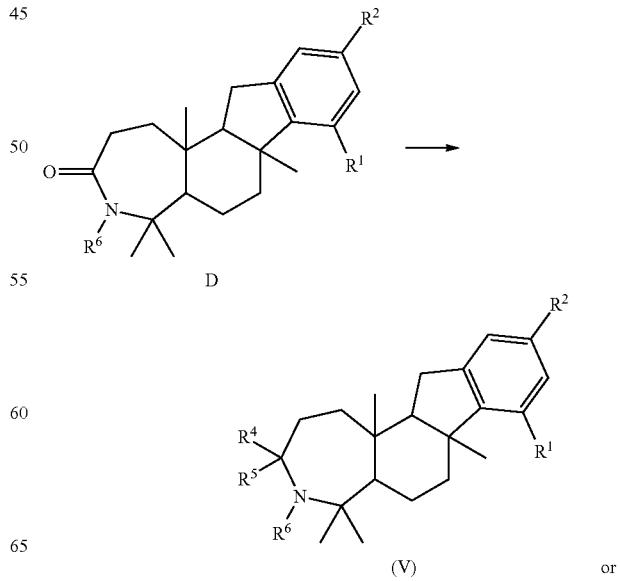

(V) or

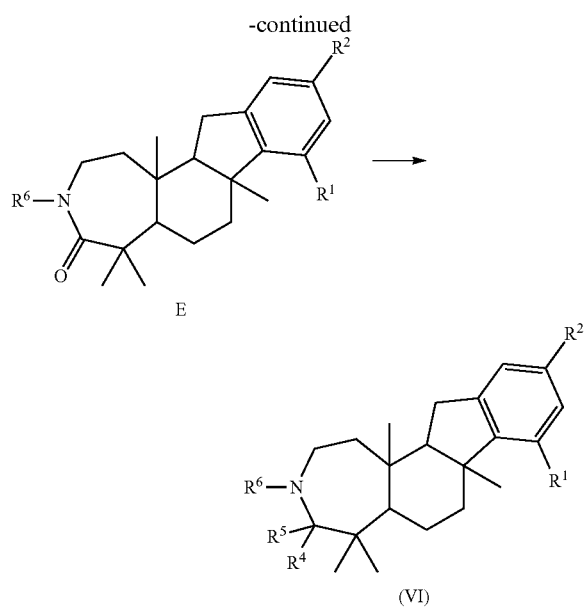

(VI)

wherein the compound of structure D or E has been prepared according to a method disclosed herein.

In other embodiments, converting the compound of structure D or E to a compound of structure (V) or (VI), respectively, comprises treating the compound of structure D or E with a reducing agent. For example, in some embodiments the reducing agent is LiAlH$_4$.

In other embodiments, the method further comprises converting the compound of structure (IV-3) to a compound of structure (IV-4):

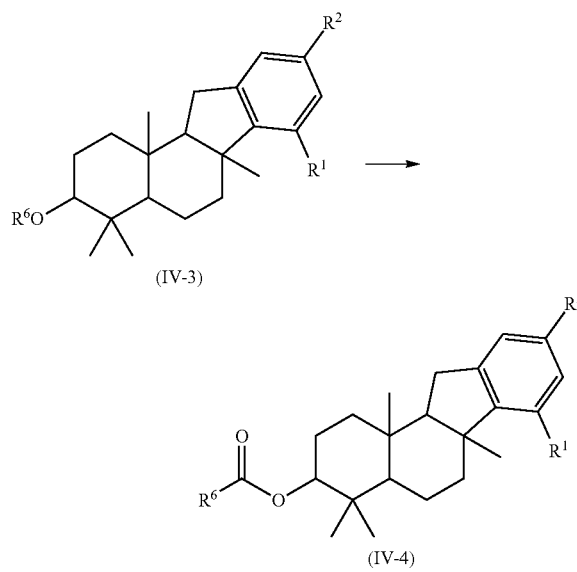

wherein the compound of structure (IV-3) has been prepared according to a method disclosed herein.

In further embodiments, converting the compound of structure (IV-3) to a compound of structure (IV-4) comprises reacting the compound of structure (IV-3) with an acylating, alkylating or arylating reagent. For example, in some embodiments, the acylating reagent comprises 3,3,3-trifluoro-2-methoxy-2-phenylpropanoyl chloride (MTPA-Cl) or a stereoisomer thereof.

The compounds of the present invention may generally be utilized as the free acid or free base. Alternatively, the compounds of this invention may be used in the form of acid or base addition salts. Acid addition salts of the free amino compounds of the present invention may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" of structure (I) is intended to encompass any and all acceptable salt forms.

In addition, prodrugs are also included within the context of this invention. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol and amine functional groups of the compounds of structure (I). Further, in the case of a carboxylic acid (—COOH), esters may be employed, such as methyl esters, ethyl esters, and the like.

With regard to stereoisomers, the compounds of structure (I) may have chiral centers and may occur as racemates, enantiomerically enriched mixtures, individual enantiomers, mixture or diastereomers or individual diastereomers. All such isomeric forms are included within the present invention, including mixtures thereof. Compounds of structure (I) may also possess axial chirality which may result in atropisomers. Furthermore, some of the crystalline forms of the compounds of structure (I) may exist as polymorphs, which are included in the present invention. In addition, some of the compounds of structure (I) may also form solvates with water or other organic solvents. Such solvates are similarly included within the scope of this invention.

Representative isomers of the compounds of structure (I) include, but are not limited to, the following structures (IX) and (X):

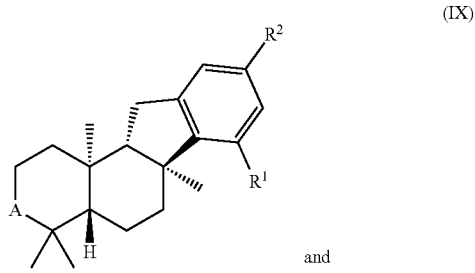

and

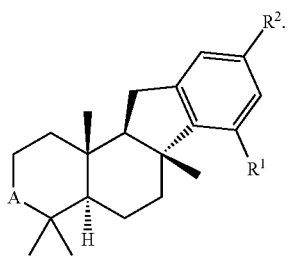
(X)
Representative compounds of this invention, which may be prepared according to the above Schemes, include (but are not limited to) the compounds listed in Table 1 below.
TABLE 1
| Representative Compounds | |
|---|---|
| Cpd. No. | Structure |
| 5a | |
| 5b | |
| 6a | |
| 6b | |
| 7a | |
| 7b | |
| 8a | |
| 8a·HCl | |
| 8b | |
| 8b·HCl | |

TABLE 1-continued

Representative Compounds

| Cpd. No. | Structure |
|---|---|
| 9a | |
| 9a·HCl | |
| 9b | |
| 9b·HCl | |
| 10a | |
| 10b | |
| 10c | |
| 11a | |
| 11b | |
| 12a | |
| 12b | |

TABLE 1-continued

Representative Compounds

| Cpd. No. | Structure |
|---|---|
| 13a | 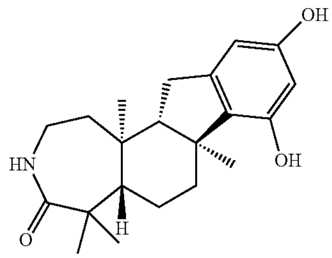 [SMILES: CC1(C)C(=O)NCC[C@]2(C)[C@@H]1CC[C@]1(C)c3c(O)cc(O)cc3C[C@@H]21] |
| 13b | 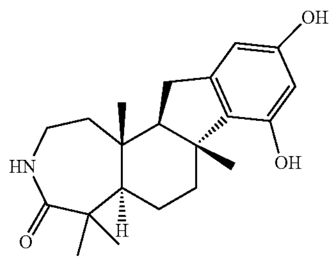 [SMILES: CC1(C)C(=O)NCC[C@]2(C)[C@H]3Cc4cc(O)cc(O)c4[C@]3(C)CC[C@@H]12] |
| 14a | 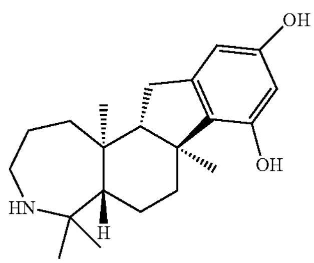 [SMILES: CC1(C)NCCC[C@]2(C)[C@@H]1CC[C@]1(C)c3c(O)cc(O)cc3C[C@@H]21] |
| 14a•HCl | 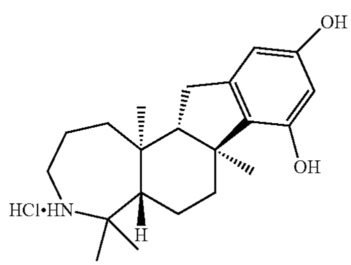 |
| 14b | 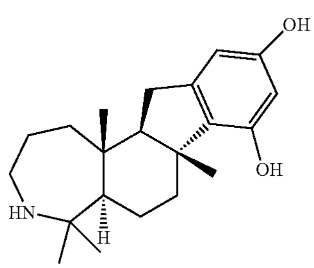 [SMILES: CC1(C)NCCC[C@]2(C)[C@H]3Cc4cc(O)cc(O)c4[C@]3(C)CC[C@@H]12] |
| 14b•HCl | |
| 15a | |
| 15a•HCl | |
| 15b | |
| 15b•HCl | |

TABLE 1-continued

Representative Compounds

| Cpd. No. | Structure |
|---|---|
| 16a | 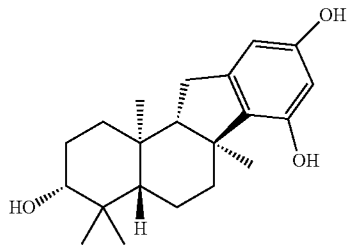 [SMILES: CC1(C)[C@H](O)CC[C@]2(C)[C@@H]1CC[C@]1(C)c3c(O)cc(O)cc3C[C@@H]21] |
| 16b | 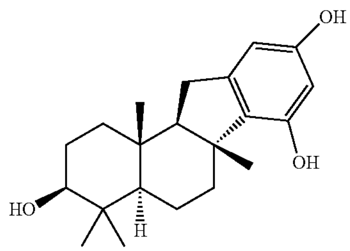 [SMILES: CC1(C)[C@@H](O)CC[C@]2(C)[C@H]3Cc4cc(O)cc(O)c4[C@]3(C)CC[C@@H]12] |
| 17a | 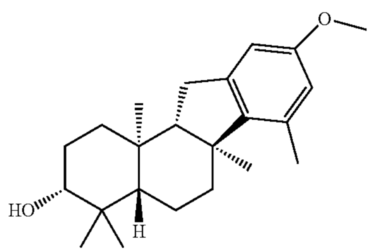 [SMILES: COc1cc(C)c2c(c1)C[C@H]1[C@]3(C)CC[C@@H](O)C(C)(C)[C@H]3CC[C@]21C] |
| 17b | 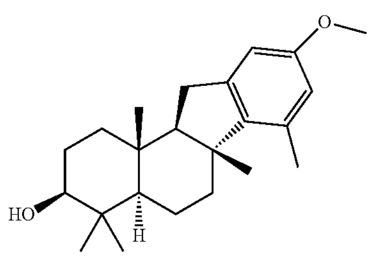 [SMILES: COc1cc(C)c2c(c1)C[C@@H]1[C@@]3(C)CC[C@H](O)C(C)(C)[C@@H]3CC[C@@]21C] |
| 18a | 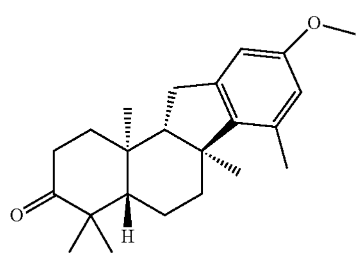 [SMILES: COc1cc(C)c2c(c1)C[C@H]1[C@]3(C)CCC(=O)C(C)(C)[C@H]3CC[C@]21C] |
| 18b | 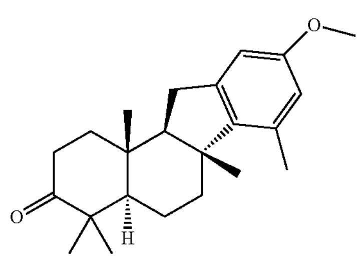 [SMILES: COc1cc(C)c2c(c1)C[C@@H]1[C@@]3(C)CCC(=O)C(C)(C)[C@@H]3CC[C@@]21C] |
| 19a | |
| 19b | |
| 20a | |
| 20a·HCl | |
| 20b | |
| 20b·HCl | |

TABLE 1-continued

Representative Compounds

| Cpd. No. | Structure |
|---|---|
| 21a | 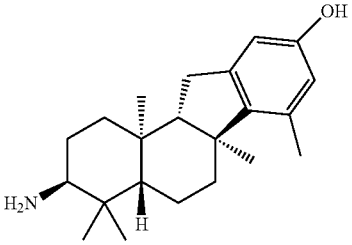 [SMILES: Cc1cc(O)cc2c1[C@@]1(C)CC[C@@H]3C(C)(C)[C@@H](N)CC[C@@]3(C)[C@@H]1C2] |
| 21a• HCl | 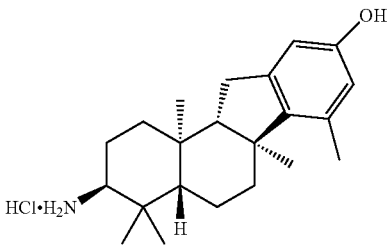 |
| 21b | 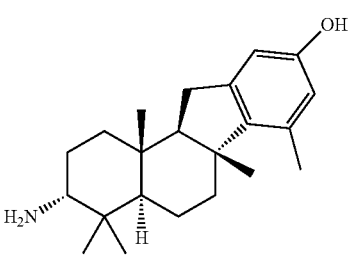 [SMILES: Cc1cc(O)cc2c1[C@]1(C)CC[C@H]3C(C)(C)[C@H](N)CC[C@]3(C)[C@H]1C2] |
| 21b• HCl | 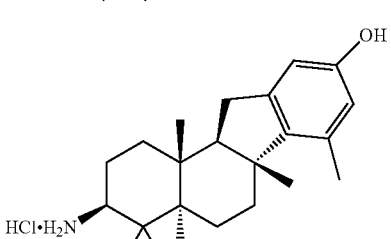 |
| NA | — |

The effectiveness of a compound as a SHIP1 modulator may be determined by any number of known techniques, including the assay set forth in Example 29. As SHIP1 modulators, the compounds of this invention have utility over a wide range of therapeutic applications, and may be used to treat a variety of conditions in men and women, as well as mammals in general. For example, such conditions include autoimmune diseases such as idiopathic pulmonary fibrosis, Still's Disease, Sjögren's Syndrome, systemic lupus erythematosus, and systemic sclerosis; inflammatory diseases such as allergic rhinitis, Alzheimer's Disease, asthma, ocular inflammatory diseases (including allergic conjunctivitis, dry eye, and uveitis), chronic obstructive pulmonary disease, eczema, inflammatory bowel disease (including Crohn's Disease and ulcerative colitis), post operative inflammation, multiple sclerosis, psoriasis, seronegative spondyloarthropathies (including anklyosing spondylitis, psoriatic arthritis, and Reiter's Syndrome) rheumatoid arthritis, and vasculitis (including Wegener's Granulomatosis, polyarteritis nodosa, leucocytoclastic vasculitis, Churg-Strauss Syndrome, cryoglobulinemic vasculitis and giant cell arteritis); and neoplastic diseases or other cell proliferative disorders such as acute myelogenous leukemia, chronic myelogenous leukemia, acute lymphocytic leukemia, chronic lymphocytic leukemia, basophilic leukemia, cutaneous T-cell lymphoma, Sezary Syndrome, Hodgkin's Disease, Non-Hodgkin's Lymphoma, multiple myeloma, hypereosinophilic syndromes, mastocytosis and thrombocythemia.

For the purposes of administration, the compounds of the present invention may be formulated as pharmaceutical compositions. Pharmaceutical compositions comprise one or more compounds of this invention in combination with a pharmaceutically acceptable carrier and/or diluent. The compound is present in the composition in an amount which is effective to treat a particular disorder—that is, in an amount sufficient to achieve SHIP1 modulation activity, and preferably with acceptable toxicity to the patient. Typically, the pharmaceutical compositions of the present invention may include a compound in an amount from 0.1 mg to 500 mg, 0.1 mg to 250 mg, 0.5 to 150 mg, 1 mg to 75 mg, 5 mg to 50 mg or 5 to 25 mg per dosage depending upon the route of administration. Typically, the pharmaceutical compositions of the present invention may include a compound in an amount from 1 mg to 60 mg per dosage. Appropriate concentrations and dosages can be readily determined by one skilled in the art.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a compound of this invention, diluents, dispersing and surface active agents, binders, and lubricants. One skilled in this art may further formulate the compounds in an appropriate manner, and in accordance with accepted practices, such as those disclosed in *Remington's Pharmaceutical Sciences*, Gennaro, Ed., Mack Publishing Co., Easton, Pa. 1990.

In another embodiment, the present invention provides a method for modulation SHIP1 generally and, more specifically, to treating the conditions as discussed above. Such methods include administering of a compound of the present invention to a warm-blooded animal in an amount sufficient to treat the condition. In this context, "treat" includes prophylactic administration. Such methods include systemic administration of a compound of this invention, preferably in the form of a pharmaceutical composition as discussed above. As used herein, systemic administration includes oral and parenteral methods of administration. For oral administration, suitable pharmaceutical compositions include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parenteral administration, the compounds of the present invention can be prepared in aqueous injection solutions which may contain buffers, antioxidants, bacteriostats, and other additives commonly employed in such solutions.

In another embodiment, the present invention provides SHIP1 modulators having enhanced water solubility compared to known SHIP1 modulators. Enhanced water solubility provides many advantages including ease of formulation and delivery as well as enhanced bioavailability. While not wishing to be bound by theory, the present inventors believe that the enhanced water solubility of the disclosed compounds may be a result of polar solublizing groups contained in A of structure (I). Thus, in one embodiment the present disclosure provides compounds of structure (I) which comprise 2 times, 5 times, 10 times, 50 times, 100 times, 500 times, 1000 times or greater solubility in water as compared to other known SHIP1 modulators. For example, in some embodiments the compound of structure (I) has a water solubility of greater than 10 µg/mL, greater than 50 µg/mL, greater than 100 µg/mL, greater than 250 µg/mL, greater than 500 µg/mL, greater than 1000 µg/mL, greater than 1,500 µg/mL, greater than 2,000 µg/mL or greater than 5,000 µg/mL in water.

EXAMPLES

The following examples are provided for purposes of illustration, not limitation. In summary, the following Examples disclose the synthesis of representative compounds of this invention as well as how they may be assayed.

Example 1

Synthesis of 1,3-dimethoxy-5-[(2E,6E)-3,7,11-trimethyldodeca-2,6,10-trien-1-yl]benzene (2)

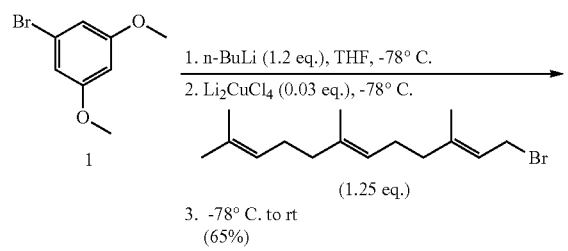

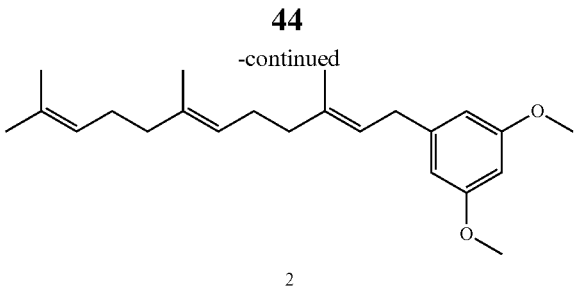

Aryl bromide 1 (1.0 g, 4.6 mmol, from Sigma-Aldrich) was dissolved in 23 mL of THF and brought to −78° C. To this solution, 3.45 mL of 1.6 M n-BuLi in hexanes (5.5 mmol) was added dropwise, and the reaction was allowed to stir for 15 minutes. To this solution was added 1.38 mL of 0.1 M $Li_2CuCl_4$ in THF (0.03×) and the solution was allowed to stir for 10 minutes at −78° C. Finally trans, trans-farnesyl bromide (trans, trans-1-bromo-3,7,11-trimethyl-2,6,10-dodecatriene, CAS No. 28290-41-7, 1.64 g, 5.75 mmol) dissolved in 20 mL of THF was added dropwise and the reaction was allowed to warm with stirring from −78° C. to room temperature overnight. The reaction was then quenched with saturated aqueous $NH_4Cl$ (50 mL), and the aqueous phase was extracted 3 times with methylene chloride (3×50 mL). The organic extracts were dried with $MgSO_4$ and concentrated. The crude mixture was then purified by flash chromatography (hexanes:ethyl acetate, 30:1) to give 2 as a clear oil (1.02 g, 2.99 mmol, 65%). $^1$H NMR (400 MHz, $CDCl_3$) δ6.36 (d, J=2.3 Hz, 2H), 6.30 (t, J=2.7 Hz, 1H), 5.34 (t, J=7.3 Hz, 1H), 5.15-5.08 (m, 2H), 3.78 (s, 6H), 3.31 (d, 2H), 2.16-1.96 (m, 8H), 1.71 (s, 3H), 1.69 (s, 3H), 1.60 (s, 6H); $^{13}$C NMR (100 MHz, $CDCl_3$) δ 160.8 (2C), 144.2, 136.5, 135.1, 131.2, 124.4, 124.1, 122.6, 106.4 (2C), 97.6, 55.2 (2C), 39.7 (2C), 34.4, 26.7, 26.6, 25.7, 17.6, 16.2, 16.0. ESIMS [M]$^+$ calcd for $C_{23}H_{35}O_2$ 343.2637, found 343.2628.

Example 2

Synthesis of (3R)-3-[(3E,7E)-9-(3,5-Dimethoxyphenyl)-3,7-dimethyl-nona-3,7-dienyl]-2,2-dimethyl-oxirane (4b)

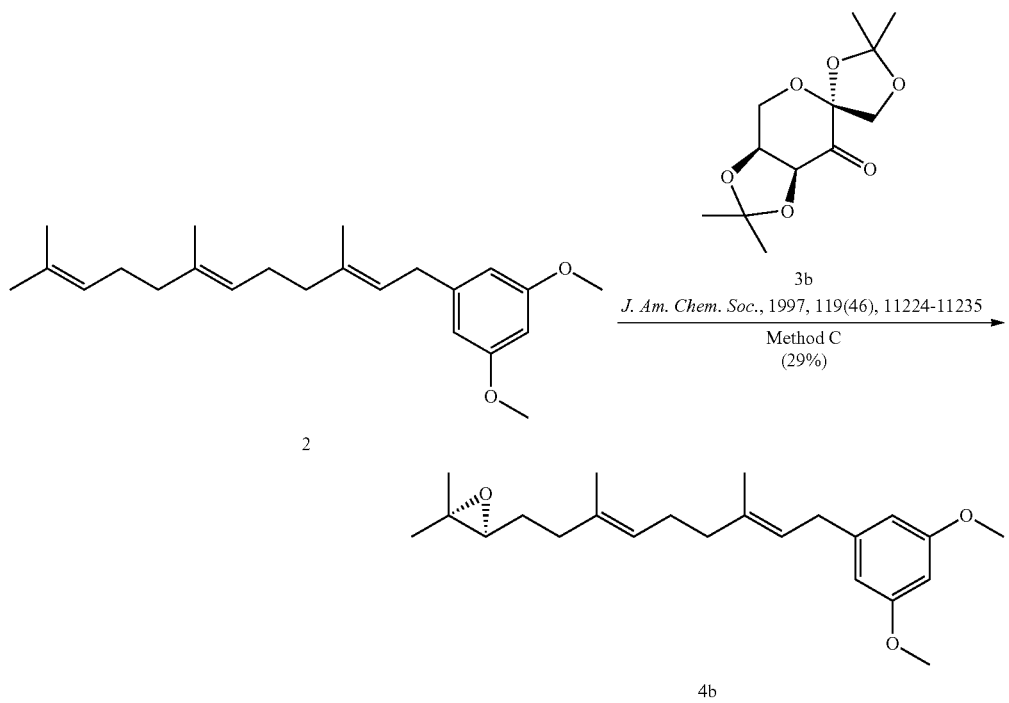

The method to prepare 4b was adapted from Wang, Z.-X., et al., *J. Am. Chem. Soc.*, 1997, 119(46), 11224-11235. Method C. Polyene 2 (1.00 g, 2.90 mmol) was oxidized to 4b (113 mg, 0.315 mmol, 11%), utilizing 3b (for synthesis of 3b see Zhao, M.-X. and Shi, Y., *J. Org. Chem.*, 2006, 71(14), 5377-9). The yield of 4b was 29% based on recovered starting material 2 (623 mg, 1.82 mmol). $^1$H NMR (400 MHz, CDCl$_3$) δ 6.34 (d, J=2.2 Hz, 2H), 6.29 (t, J=2.2 Hz, 1H), 5.33 (t, J=6.1 Hz, 1H), 5.18 (t, J=5.7 Hz, 1H), 3.76 (s, 6H), 3.29 (d, J=7.2 Hz, 2H), 2.68 (t, J=6.2 Hz, 1H), 2.11-2.14 (m, 4H), 2.04-2.08 (m, 4H), 1.71 (s, 3H), 1.62 (s, 3H), 1.29 (s, 3H), 1.25 (s, 3H); $^{13}$C NMR (100 MHz, CDCl$_3$) δ 160.6 (2C), 143.9 (2C), 136.1, 134.0, 124.6, 122.7, 106.3, 97.4, 63.9, 58.0, 55.0 (2C), 39.5, 36.1, 34.3, 27.3, 26.4, 24.7, 18.6, 16.0, 15.9. ESIMS [M+Na]$^+$ calcd for C$_{23}$H$_{34}$O$_3$Na 381.2406, found 381.2415.

Example 3

Synthesis of (3S,4aR,6aR,11aR,11bR)-7,9-Dimethoxy-4,4,6a,11b-tetramethyl-2,3,4,4a,5,6,6a,11,11a,11b-decahydro-1H-benzo[a]fluoren-3-ol (5b)

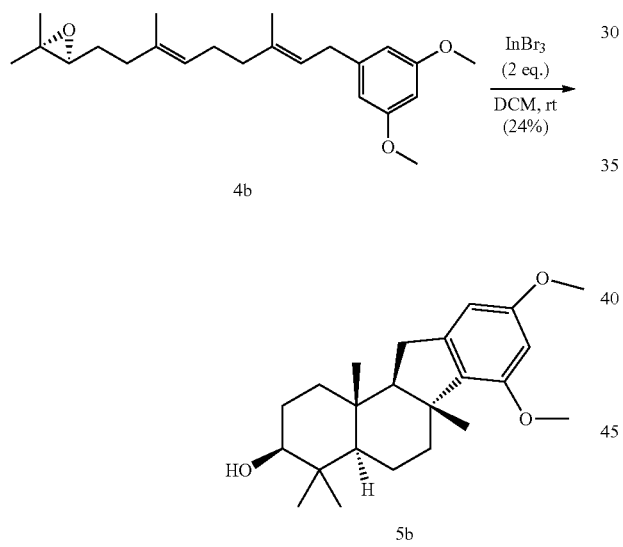

4b

5b

To epoxide 4b (3.53 g, 9.86 mmol) dissolved in 105 mL of methylene chloride was added indium bromide (InBr$_3$) (6.99 g, 19.7 mmol), and the reaction was allowed to stir for 1 hour. The reaction mixture was then quenched with saturated aqueous NaHCO$_3$ (50 mL), and the aqueous layer was extracted 3 times with methylene chloride (3×50 mL). The organic extracts were combined, dried with MgSO$_4$ and concentrated. The crude reaction mixture was purified by flash chromatography (hexanes:ethyl acetate, 3:1) to give a mixture of tetracycle 5b and various tricyclic impurities.

The product mixture was then crystallized using boiling solvent (hexanes:ethyl acetate 15:1) to give 5b (860 mg, 2.39 mmol, 24%). $^1$H NMR (400 MHz, CDCl$_3$) δ 6.40 (d, J=1.8 Hz, 1H), 6.26 (d, J=2.0 Hz, 1H), 3.77 (s, 3H), 3.75 (s, 3H), 3.22 (m, 1H), 2.62 (m, 1H), 2.50 (dd, J=14, 6.2 Hz, 1H), 2.45 (dd, J=9.5, 3.2 Hz, 1H), 1.74-1.55 (m, 7H), 1.18-1.11 (m, 1H), 1.08 (s, 3H), 1.03 (s, 3H), 0.99 (s, 3H)), 0.91 (m, 1H), 0.84 (s, 3H); $^{13}$C NMR (100 MHz, CDCl$_3$) δ 159.3, 155.8, 144.8, 133.4, 101.9, 96.8, 79.1, 64.4, 56.1, 55.4, 55.0, 46.0, 38.8, 38.5, 38.2, 36.6, 29.5, 27.9, 27.1, 20.3, 19.2, 16.2, 15.1. ESIMS [M+Na]$^+$ calcd for C$_{23}$H$_{34}$O$_3$Na 381.2406, found 381.2415. [α]$^{24}_D$=+18.86°.

Example 4

Synthesis of (4aR,6aR,11aR,11bR)-7,9-Dimethoxy-4,4,6a,11b-tetramethyl-1,2,4,4a,5,6,6a,11,11a,11b-decahydro-benzo[a]fluoren-3-one (6b)

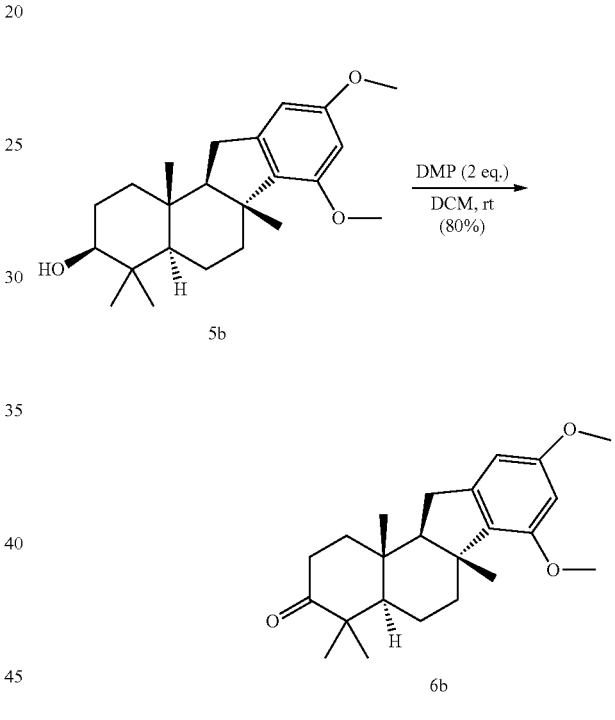

5b

6b

To alcohol 5b (600 mg, 1.67 mmol) dissolved in 85 mL of methylene chloride was added Dess-Martin periodinane (DMP, 1.41 g, 3.34 mmol), and the mixture was allowed to stir at room temperature for 1.5 hours. Upon reaction completion, saturated aqueous NaHCO$_3$ (50 mL) was added and the aqueous phase was extracted 3 times with methylene chloride (3×50 mL). The organic extracts were then combined, dried with MgSO$_4$, and concentrated. The crude mixture was purified using flash chromatography (hexanes:ethyl acetate 7:1) to give 6b (476 mg, 1.34 mmol, 80% yield) as a white crystalline solid. $^1$H NMR (400 MHz, CDCl$_3$) δ 6.41 (s, 1H), 6.27 (s, 1H), 3.77 (s, 3H), 3.75 (s, 3H), 2.71-2.65 (m, 1H), 2.64-2.56 (m, 2H), 2.54-2.41 (m, 2H), 1.87-1.81 (m, 1H), 1.78-1.73 (m, 2H), 1.71-1.48 (m, 4H), 1.13 (s, 3H), 1.11 (s, 6H), 1.09 (s, 3H); $^{13}$C NMR (100 MHz, CDCl$_3$) δ217.2, 159.5, 155.8, 144.4, 132.9, 101.9, 96.8, 63.4, 55.4, 55.3, 54.9, 47.5, 45.8, 38.8, 37.4, 36.2, 33.9, 29.5, 26.5, 20.7, 20.5, 19.8, 15.5. ESIMS [M+Na]+ calcd for $C_{23}H_{32}O_3Na$ 379.2249, found 379.2243. $[\alpha]^{24}_D$=+26.78°.

Example 5

Synthesis of (4aR,6aR,11aR,11bR)-7,9-Dihydroxy-4,4,6a,11b-tetramethyl-1,2,4,4a,5,6,6a,11,11a,11b-decahydro-benzo[a]fluoren-3-one (7b)

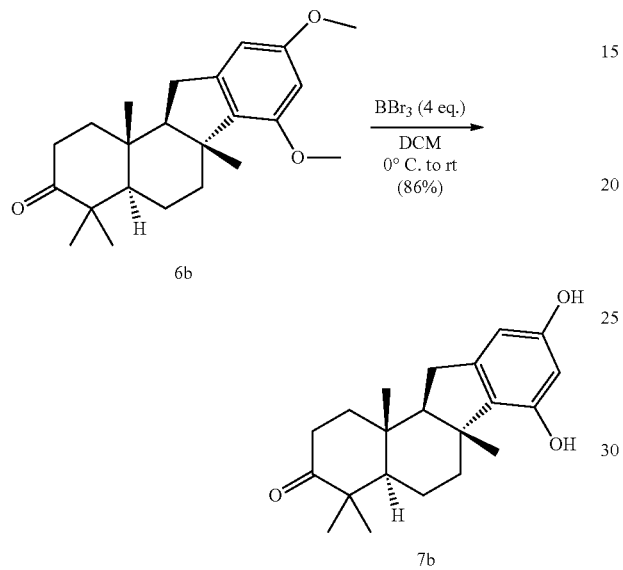

To ketone 6b (240 mg, 0.67 mmol) dissolved in 20 mL of methylene chloride stirring at 0° C. was added 2.7 mL of BBr₃ (1.0 M in methylene chloride, 2.69 mmol). After stirring for one hour at 0° C., 6b was still present, and the reaction was allowed to reach room temperature over the next two hours. The reaction was then quenched with methanol, and water was added to the mixture. The aqueous phase was then extracted 3 times with methylene chloride (3×50 mL). The combined organic extracts were dried with MgSO₄ and concentrated. The crude mixture was purified by flash chromatography to give 7b (190 mg, 0.578 mmol, 86%) as a white crystalline solid. ¹H NMR (400 MHz, (CD₃)₂CO) δ 7.76 (s, 1H), 7.73 (s, 1H), 6.24 (t, J=0.96 Hz, 1H), 6.13 (d, J=1.6 Hz, 1H)), 2.66-2.61 (m, 1H), 2.59-2.52 (m, 2H), 2.49-2.46 (m, 1H), 2.44-2.37 (m, 1H), 1.86-1.82 (m, 1H), 1.81-1.77 (m, 1H), 1.76-1.71 (m, 1H), 1.67-1.55 (m, 4H), 1.15 (s, 3H), 1.13 (s, 3H), 1.07 (s, 3H), 1.09 (s, 3H); ¹³C NMR (100 MHz, (CD₃)₂CO) δ 216.9, 158.5, 154.8, 146.7, 131.9, 105.8, 102.8, 65.4, 57.2, 48.9, 47.3, 40.5, 39.6, 38.0, 35.4, 30.9, 27.9, 22.2, 22.1, 21.3, 16.9. ESIMS [M+Na]+ calcd for $C_{21}H_{28}O_3Na$ 351.1936, found 351.1929. $[\alpha]^{24}_D$=+24.07°.

Example 6

Synthesis of (3R,4aR,6aR,11aR,11bR)-3-Amino-4,4,6a,11b-tetramethyl-2,3,4,4a,5,6,6a,11,11a,11b-decahydro-1H-benzo[a]fluorene-7,9-diol Hydrochloride (8b.HCl) and (3S,4aR,6aR,11aR,11bR)-3-Amino-4,4,6a,11b-tetramethyl-2,3,4,4a,5,6,6a,11,11a,11b-decahydro-1H-benzo[a]fluorene-7,9-diol Hydrochloride (9b.HCl)

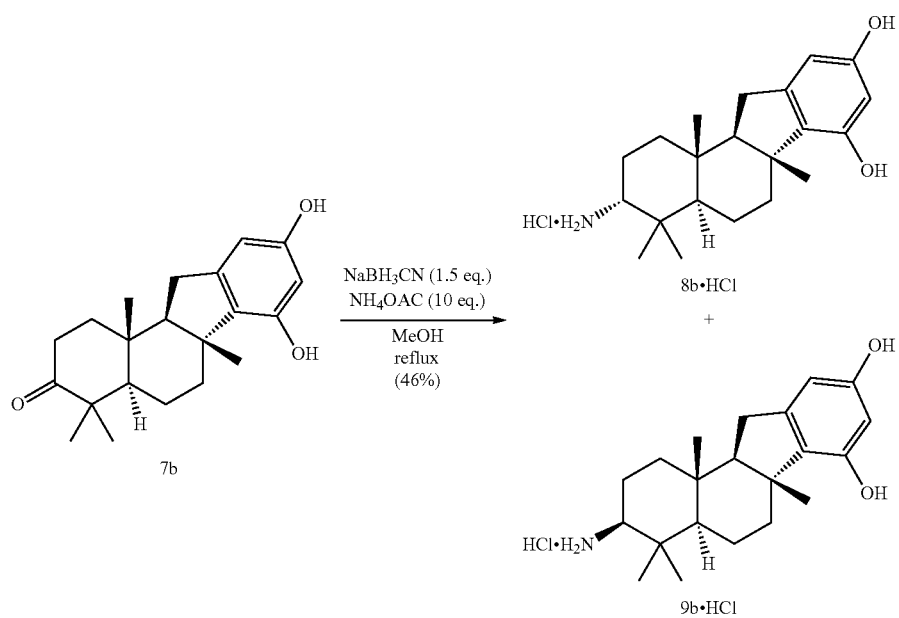

To a suspension of ketone 7b (250 mg, 0.761 mmol) in 50 mL of MeOH was added NaBH₃CN (71.7 mg, 1.14 mmol) and NH₄OAc (587 mg, 7.61 mmol). The reaction was then gently refluxed overnight. Upon the disappearance of staring material, the reaction was cooled and then concentrated to dryness. The crude material was partitioned between water (200 mL) and methylene chloride and acidified to pH 5 with 6 M HCl. The aqueous phase was then extracted 5 times with methylene chloride (5×50 mL). The resultant aqueous phase was frozen and lyophilized overnight to give a white amorphous solid. To this solid was added 10 mL of water and the mixture was sonicated to give a heterogeneous mixture which was loaded on to a 10 g reverse phase Sep-Pak® (which was washed with 100 mL of MeOH followed by 100 mL of H₂O). Once loaded, the column was flushed with water (100 mL), 60:40 H₂O:MeOH (100 mL, 3×), and MeOH. The fractions of interest were the first 60:40 H₂O:MeOH fraction containing 78.2 mg of 8b pure, and the second and third fraction contained 50.7 mg of a 2:1 mixture of 8b and 9b as the HCl salt and the free base, which was acidified and subsequently repurified using the same method. When fully purified the result was 8b.HCl (112 mg, 0.306 mmol, 40%), and 9b.HCl (16.9 mg, 0.0461 mmol, 6%), with a diastereomeric ratio between 8b.HCl and 9b.HCl of 20:3, respectively.

Compound 8b.HCl: $^1$H NMR (600 MHz, CD₃OD) δ 6.16 (s, 1H), 6.02, (d, J=1.5 Hz, 1H), 2.93 (dd, J=12, 4.3 Hz, 1H), 2.57 (t, J=13 Hz, 1H), 2.51 (dt, J=12, 2.9 Hz, 1H), 2.42 (dd, J=14, 6.0 Hz, 1H), 1.85 (qd, J=13, 3.4 Hz, 1H), 1.79-1.73 (m, 2H), 1.71-1.67 (m, 3H), 1.63 (td, J=12, 3.5 Hz, 1H), 1.27 (td, J=13, 3.4 Hz, 1H), 1.11 (dd, J=11, 2.3 Hz, 1H), 1.09 (s, 3H), 1.08 (s, 6H), 0.94 (s, 3H); $^{13}$C NMR (150 MHz, CD₃OD) δ 157.5, 154.2, 145.9, 131.7, 104.7, 101.9, 65.6, 61.7, 57.6, 46.8, 39.6, 39.2, 37.8, 37.7, 30.1, 28.2, 24.3, 20.8, 20.2, 16.4, 15.9. ESIMS [M+H]⁺ calcd for C₂₁H₃₂NO₂ 330.2433, found 330.2441. $[\alpha]^{24}_D$=+6.98°.

Compound 9b.HCl: $^1$H NMR (600 MHz, CD₃OD) δ 6.16 (s, 1H), 6.02 (d, J=1.2 Hz, 1H), 3.09 (m, 1H), 2.58 (t, J=13 Hz, 1H), 2.51 (m, 1H), 2.44 (dd, J=14, 6.0 Hz, 1H), 2.29 (tt, J=14, 3.3 Hz, 1H), 1.83 (dd, J=12, 6.1 Hz, 1H), 1.71-1.69 (m, 1H), 1.68-1.66 (m, 1H), 1.64-1.59 (m, 1H), 1.49 (dt, J=11, 2.1 Hz, 1H) 1.39 (d, J=8.5 Hz, 1H), 1.34-1.27 (m, 2H), 1.11 (s, 3H), 1.09 (s, 3H), 1.07 (s, 3H), 1.01 (s, 3H); $^{13}$C NMR (150 MHz, CD₃OD) δ 157.5, 154.2, 146.0, 131.8, 104.7, 101.9, 65.1, 59.5, 51.4, 47.1, 39.6, 37.9, 36.6, 34.1, 30.1, 28.4, 22.9, 22.7, 20.9, 20.2, 16.5. ESIMS [M+H]⁺ calcd for C₂₁H₃₂NO₂ 330.2433, found 330.2440. $[\alpha]^{24}_D$=−8.27°.

Example 7

Synthesis of (3S,4aR,6aR,11aR,11bR)-7,9-dimethoxy-4,4,6a,11b-tetramethyl-2,3,4,4a,5,6,6a,11,11a,11b-decahydro-1H-benzo[a]fluoren-3-yl (2S)-3,3,3-trifluoro-2-methoxy-2-phenylpropanoate (10b)

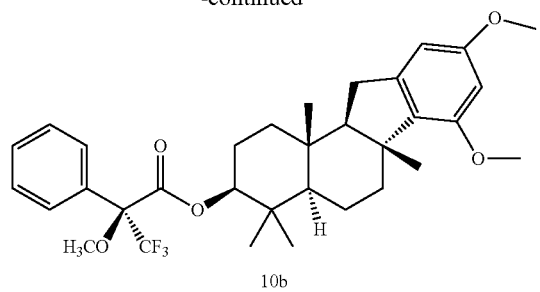

10b

Alcohol 5b (219 mg, 0.610 mmol) was dissolved in 4 mL of methylene chloride (DCM). To this mixture was added pyridine (0.074 mL, 0.92 mmol) and dimethylaminopyridine (DMAP) (7.4 mg, 0.061 mmol), and the mixture was taken to 0° C. To this mixture was added (R)-(−)-MTPA-Cl (170 mg, 0.671 mmol), and the mixture was allowed to warm to room temperature overnight. The reaction was quenched with saturated aqueous NH₄Cl (50 mL), and the aqueous layer was extracted 3 times with methylene chloride (3×50 mL). The organic extracts were combined and dried with MgSO₄ and concentrated. A $^1$H NMR (400 MHz) spectrum of the crude mixture showed the absence of diastereomers, meaning that alcohol 5b was enantiomerically pure after crystallization. The product mixture was then purified using flash chromatography (hexanes:ethyl acetate 12:1) to give 10b quantitatively. $^1$H NMR (400 MHz, CDCl₃) δ 7.54 (m, 2H), 7.41 (m, 3H), 6.40 (d, J=1.8 Hz, 1H), 6.26 (d, J=1.9 Hz, 1H), 4.72 (dd, J=12, 4.9 Hz, 1H), 3.77 (s, 3H), 3.75 (s, 3H), 3.54 (s, 3H), 2.62 (m, 1H), 2.51 (dd, J=14, 6.2 Hz, 1H), 2.46 (dd, J=8.4, 2.9 Hz, 1H), 1.85-1.76 (m, 1H), 1.74-1.67 (m, 3H), 1.65-1.57 (m, 3H), 1.23 (td, J=13, 4.2 Hz, 1H), 1.07 (s, 3H), 1.04 (s, 3H), 1.04 (m, 1H), 0.92 (s, 3H), 0.87 (s, 3H); $^{13}$C NMR (100 MHz, CDCl₃) δ 166.3, 159.5, 155.8, 144.7, 133.2, 132.3, 129.5, 128.3 (2C), 127.6 (2C), 124.9, 122.0, 101.9, 96.9, 84.5, 64.2, 56.2, 55.4, 55.3, 55.1, 46.1, 38.1, 38.0, 37.9, 36.5, 29.5, 28.1, 23.0, 20.3, 19.0, 16.2, 16.1. ESIMS [M+Na]⁺ calcd for C₃₃H₄₁O₅F₃Na 597.2804, found 597.2814. $[\alpha]^{24}_D$=−31.76°.

Example 8

Synthesis of (4aR,6aR,11aR,11bR)-3-(hydroxyimio)-4,4,6a,11b-tetramethyl-1H,2H,3H,4H,4aH,5H,6H,6aH,11H,11aH,11bH-cyclohexa[a]fluorene-7,9-diol (11b)

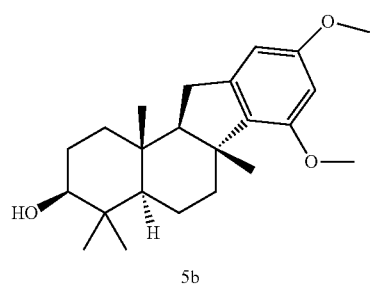

5b

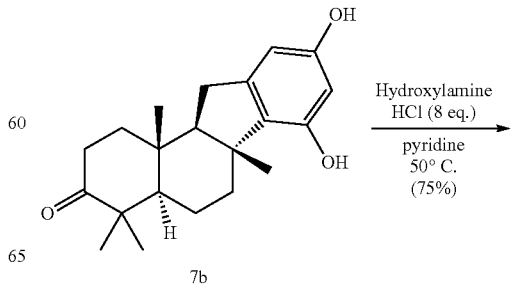

7b

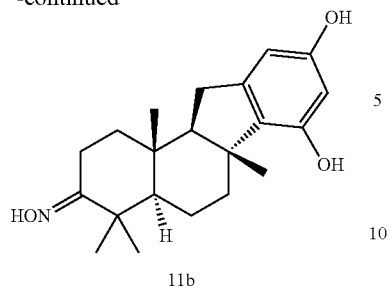

11b

To 7b (20 mg, 0.060 mmol) dissolved in 1 mL of pyridine was added hydroxylamine hydrochloride (33.8 mg, 0.487 mmol), and the mixture was gently heated at 50° C. After 3.5 hours, the reaction mixture was cooled and saturated aqueous ammonium chloride solution (50 mL) was added. The aqueous phase was then extracted 3 times with methylene chloride (3×50 mL). The organic extracts were combined and dried with MgSO$_4$, and concentrated. An acidic workup with 1 M HCl to remove the pyridine resulted in product degradation, therefore nitrogen was blown over the crude mixture until the disappearance of pyridine was observed by TLC. The crude mixture was purified with flash chromatography (hexanes: ethyl acetate 1:1) to give 11b as a white solid (15.5 mg, 0.045 mmol, 75%). $^1$H NMR (400 MHz, (CD$_3$)$_2$CO) δ 6.22 (s, 1H), 6.12 (s, 1H), 3.06 (ddd, J=16, 3.2, 2.7 Hz, 1H), 2.59 (t, J=14 Hz, 1H), 2.53 (dt, J=12, 3.2 Hz, 1H), 2.44 (dd, J=14, 6.1 Hz, 1H), 2.29 (ddd, J=19, 6.4, 5.8 Hz, 1H), 1.75-1.72 (m, 1H), 1.71-1.69 (m, 2H), 1.68-1.66 (m, 1H), 1.65-1.61 (m, 1H), 1.29-1.23 (m, 2H)), 1.15 (s, 3H), 1.14 (s, 3H), 1.11 (s, 3H), 1.08 (s, 3H); $^{13}$C NMR (100 MHz, (CD$_3$)$_2$CO) δ 171.9, 165.8, 158.5, 154.8, 146.8, 132.1, 105.8, 102.8, 65.9, 61.5, 58.3, 47.4, 41.7, 40.0, 38.4, 29.2, 24.3, 21.7, 18.1, 16.8, 15.5. ESIMS [M+H]$^+$ calcd for C$_{21}$H$_{30}$O$_3$N 344.2226, found 344.2230. $[\alpha]^{24}_D$=−14.94°.

Example 9

Synthesis of (5aR,7aR,12aR,12bR)-8,10-dihydroxy-5,5,7a,12b-tetramethyl-1H,2H,3H,4H,5H,5aH,6H,7H,7aH,12H,12aH,12bH-fluoreno[2,1-C]azepin-3-one (12b) and (5aR,7aR,12aR,12bR)-8,10-dihydroxy-5,5,7a,12b-tetramethyl-1H,2H,3H,4H,5H,5aH,6H,7H,7aH,12H,12aH,12bH-fluoreno[1,2-D]azepin-4-one (13b)

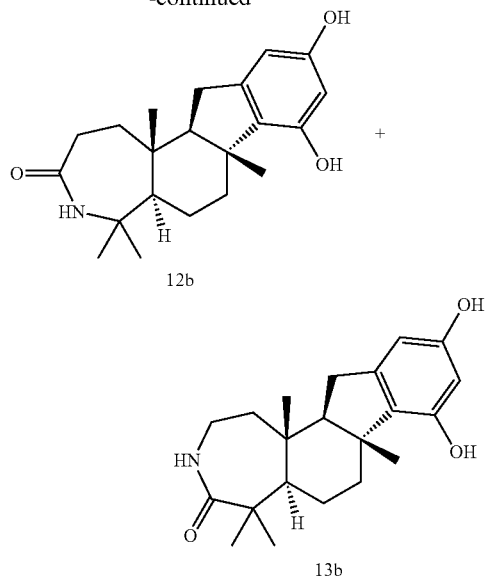

12b

13b

To 11b (10 mg, 0.029 mmol) dissolved in 1 mL of methylene chloride at 0° C. was added trifluoroacetic anhydride (TFAA, 0.11 mL, 0.78 mmol), and the mixture was allowed to stir for 1 hour. The reaction was quenched with water (0.1 mL) and concentrated under a stream of nitrogen. The crude mixture was purified with flash chromatography (methylene chloride:methanol 12:1) to give 12b and 13b.

Compound 12b: (10.0 mg, 0.029 mmol, 96%) as a white solid. $^1$H NMR (400 MHz, CD$_3$OD) δ 6.17 (d, J=1.7 Hz, 1H), 6.02 (d, J=1.9 Hz, 1H), 3.45 (s, 1H), 2.65-2.56 (m, 2H), 2.51-2.43 (m, 3H), 1.83-1.70 (m, 4H), 1.69-1.61 (m, 2H), 1.59-1.52 (m, 1H), 1.33 (s, 3H), 1.32 (s, 3H), 1.22 (s, 3H), 1.11 (s, 3H); $^{13}$C NMR (100 MHz, CD$_3$OD) δ 179.3, 157.5, 154.3, 145.8, 131.6, 104.6, 101.9, 65.5, 57.8, 56.9, 46.6, 41.2, 39.3, 39.0, 33.7, 32.6, 30.6, 26.4, 24.3, 20.3, 17.5. ESIMS [M+Na]$^+$ calcd for C$_{21}$H$_{29}$NO$_3$Na 366.2045, found 366.2035. $[\alpha]^{24}_D$=+122.1°

Compound 13b: A minor regioisomer formed in the production of 12b (less than 5% of product formed). $^1$H NMR (400 MHz, CD$_3$OD) δ 6.16 (d, J=1.6 Hz, 1H), 6.02 (d, J=1.9 Hz, 1H), 3.02 (dq, J=9.4, 6.0, 2.7 Hz, 1H), 2.58 (t, J=13 Hz, 1H), 2.50 (dt, J=12, 2.9 Hz, 1H), 2.42 (dd, J=14, 6.0 Hz, 1H), 2.33 (qd, J=12, 5.4 Hz, 1H), 1.75-1.57 (m, 4H), 1.34-1.19 (m, 3H), 1.16 (s, 3H), 1.13 (s, 3H), 1.09 (s, 6H); $^{13}$C NMR (100 MHz, CD$_3$OD) δ 167.0, 157.4, 154.2, 146.2, 131.9, 104.7, 101.9, 65.5, 57.8, 46.9, 41.2, 39.5, 39.4, 37.8, 30.2, 28.3, 23.3, 21.2, 20.5, 17.7, 16.1. ESIMS [M+H]$^+$ calcd for C$_{21}$H$_{30}$NO$_3$ 344.2226, found 344.2224. $[\alpha]^{24}_D$=−5.1°

Example 10

Synthesis of (5aR,7aR,12aR,12bR)-5,5,7a,12b-tetramethyl-1H,2H,3H,4H,5H,5aH,6H,7H,7aH,12H,12aH,12bH-fluoreno[2,1-C]azepine-8,10-diol Hydrochloride (14b-HCl)

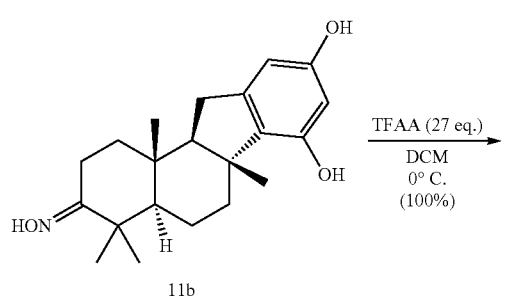

11b

TFAA (27 eq.)
DCM
0° C.
(100%)

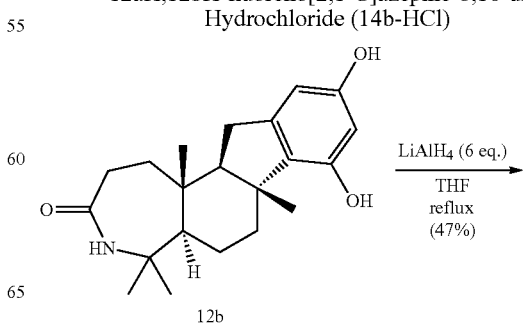

12b

LiAlH$_4$ (6 eq.)
THF
reflux
(47%)

-continued

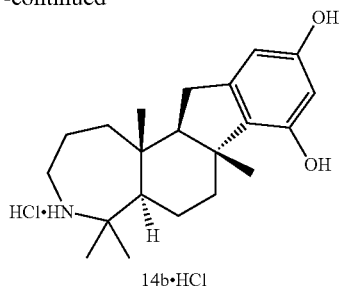

14b·HCl

To 12b (8.0 mg, 0.023 mmol) dissolved in 4 mL of THF was added LiAlH$_4$ (0.072 mL, 2. M in THF, 0.14 mmol), and the reaction was allowed to reflux overnight. Upon completion, the reaction was quenched with 0.1 mL methanol, and 0.1 mL of 6 M HCl was added. The mixture was then concentrated, lyophilized and then purified using a 2 g reverse phase Sep-Pak® (which was washed with 10 mL of MeOH followed by 10 mL of H$_2$O). Once loaded, the column was flushed with water (20 mL), 60:40 H$_2$O:MeOH (50 mL), and MeOH (50 mL). The H$_2$O:MeOH fraction after concentration and lyophilization contained 14b. HCl (4 mg, 0.01 mmol, 47%) as a white solid. $^1$H NMR (600 MHz, CD$_3$OD) δ 6.16 (s, 1H), 6.03 (d, J=1.5 Hz, 1H), 3.23-3.15 (m, 2H), 2.62 (t, J=14 Hz, 1H), 2.57 (dd, J=8.2, 6.2 Hz, 1H), 2.52 (dt, J=13, 2.9 Hz, 1H), 2.00-1.96 (m, 1H), 1.94-1.87 (m, 3H), 1.75-1.72 (m, 2H), 1.70-1.66 (m, 1H), 1.64-1.58 (m, 1H), 1.48 (s, 3H), 1.42 (s, 3H), 1.39 (m, 1H), 1.22 (s, 3H), 1.13 (s, 3H); $^{13}$C NMR (150 MHz, CD$_3$OD) δ 157.7, 154.3, 145.2, 131.2, 104.4, 101.9, 64.6, 63.6, 54.7, 46.2, 43.9, 42.6, 42.2, 38.3, 31.2, 27.9, 24.9, 24.3, 24.0, 19.5, 14.9. EIMS [M]$^+$ calcd for C$_{21}$H$_{31}$NO$_2$ 329.23548, found 329.23569. [α]$^{24}_D$=+20.50°.

Example 11

Synthesis of (3S)-3-[(3E,7E)-9-(3,5-Dimethoxyphenyl)-3,7-dimethyl-nona-3,7-dienyl]-2,2-dimethyl-oxirane (4A)

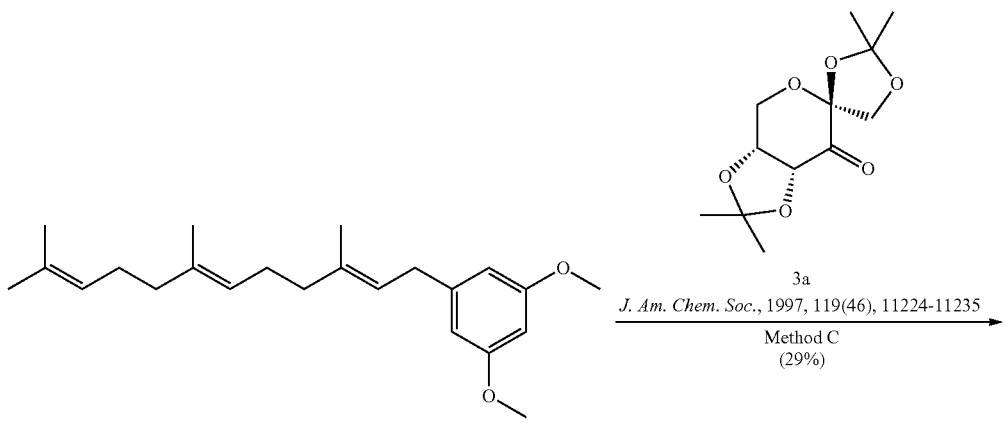

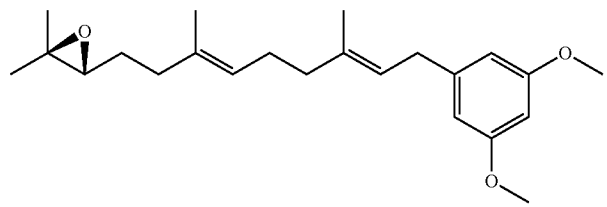

4a

Compound 4a was prepared by the method of Example 2 utilizing 3a as a catalyst. Following the procedures in Example 2, polyene 2 (1.0 g, 2.9 mmol) was converted to epoxide 4a (113.0 mg, 0.315 mmol). The yield of 4a was 29% based on recovered starting material 2 (623 mg, 1.82 mmol). $^1$H NMR and $^{13}$C NMR were identical to 4b from Example 2. ESIMS [M+Na]$^+$ calcd for C$_{23}$H$_{34}$O$_3$Na 381.2406, found 381.2415.

Example 12

Synthesis of (3R,4aS,6aS,11aS,11bS)-7,9-Dimethoxy-4,4,6a,11b-tetramethyl-2,3,4,4a,5,6,6a,11,11a,11b-decahydro-1H-benzo[a]fluoren-3-ol (5a)

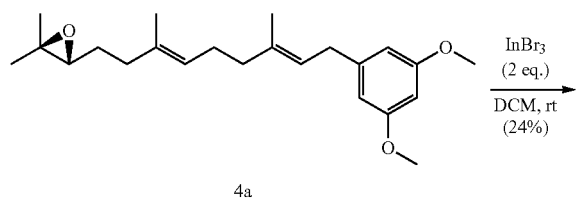

Using the procedure described in Example 3, Compound 4a (3.53 g, 9.86 mmol) was converted to 5a (860 mg, 2.39 mmol) in 24% yield. $^1$H NMR and $^{13}$C NMR were identical to 5b (from Example 3). ESIMS [M+Na]$^+$ calcd for $C_{23}H_{34}O_3Na$ 381.2406, found 381.2410. $[\alpha]^{24}_D$=−16.5°.

Example 13

Synthesis of (4aS,6aS,11aS,11bS)-7,9-Dimethoxy-4,4,6a,11b-tetramethyl-1,2,4,4a,5,6,6a,11,11a,11b-decahydro-benzo[a]fluoren-3-one (6a)

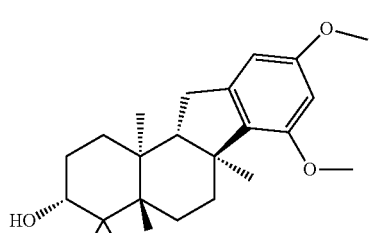

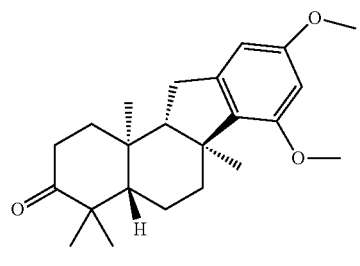

Using the procedure described in Example 4, Compound 5a (600 mg, 1.67 mmol) was converted to Compound 6a (476 mg, 1.34 mmol, 80%). Compound 6a was obtained as a white crystalline solid. $^1$H NMR and $^{13}$C NMR were identical to 6b from Example 4. ESIMS [M+H]$^+$ calcd for $C_{23}H_{33}O_3$ 357.2430, found 357.2426. $[\alpha]^{24}_D$=−27.83°.

Example 14

Synthesis of (4aS,6aS,11aS,11bS)-7,9-Dihydroxy-4,4,6a,11b-tetramethyl-1,2,4,4a,5,6,6a,11,11a,11b-decahydro-benzo[a]fluoren-3-one (7a)

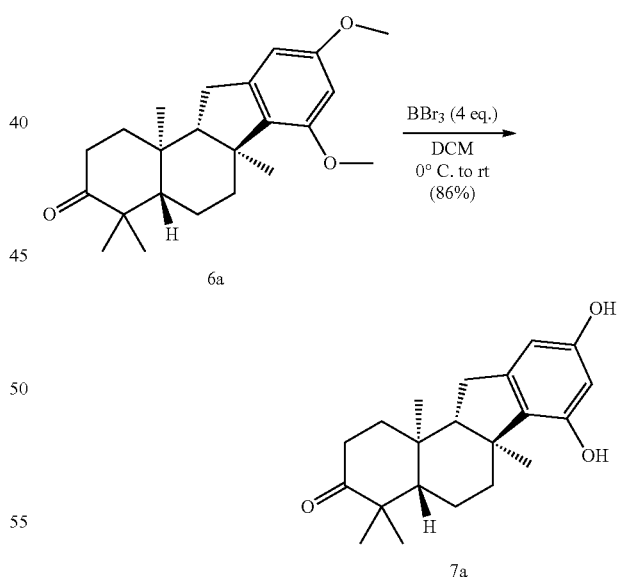

Compound 7a (190 mg, 0.578 mmol, 86%) was obtained as a white crystalline solid by reaction of 6a (240 mg, 0.67 mmol) under the conditions described in Example 5. $^1$H NMR and $^{13}$C NMR were identical to 7b from Example 5. ESIMS [M+Na]$^+$ calcd for $C_{21}H_{28}O_3Na$ 351.1936, found 351.1938. $[\alpha]^{24}_D$=+22.0°.

Example 15

Synthesis of (3S,4aS,6aS,11aS,11bS)-3-Amino-4,4,6a,11b-tetramethyl-2,3,4,4a,5,6,6a,11,11a,11b-decahydro-1H-benzo[a]fluorene-7,9-diol Hydrochloride (8a.HCl) and (3R,4aS,6aS,11aS,11bS)-3-Amino-4,4,6a,11b-tetramethyl-2,3,4,4a,5,6,6a,11,11a,11b-decahydro-1H-benzo[a]fluorene-7,9-diol Hydrochloride (9a.HCl)

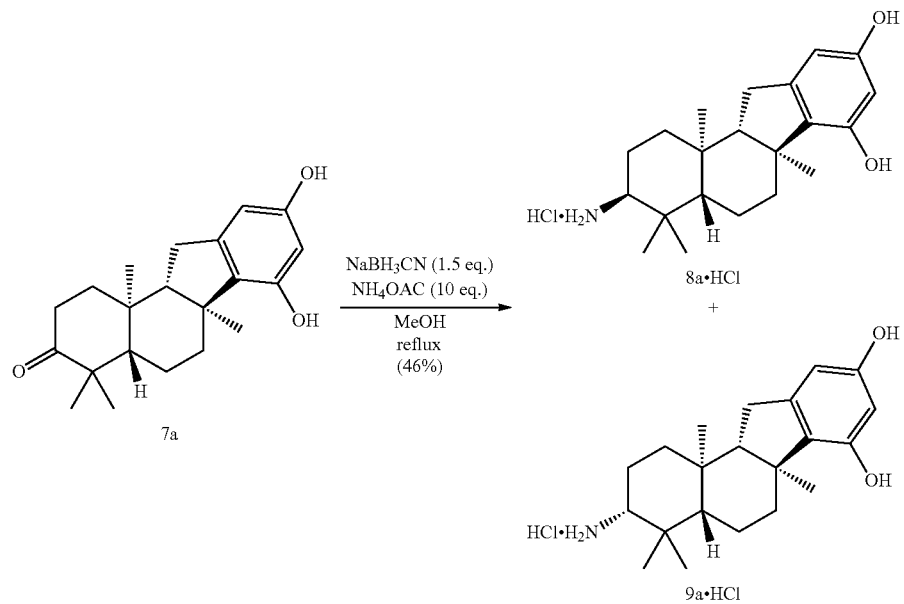

Compounds 8a.HCl (112 mg, 0.306 mmol, 40%) and 9a.HCl (16.9 mg, 0.0461 mmol, 6%), with a diastereomeric ratio between 8a.HCl and 9a.HCl of 20:3, respectively, were prepared from 7a (250 mg, 0.761 mmol) using the method of Example 6

Compound 8a.HCl: $^1$H NMR and $^{13}$C NMR were identical to 8b.HCl from Example 6. ESIMS [M+H]$^+$ calcd for $C_{21}H_{32}NO_2$ 330.2433, found 330.2440. $[\alpha]^{24}_D = -5.7°$.

Compound 9a.HCl: $^1$H NMR and $^{13}$C NMR were identical to 9b.HCl from Example 6. ESIMS [M+H]$^+$ calcd for $C_{21}H_{32}NO_2$ 330.2433, found 330.2433. $[\alpha]24_D = +5.0°$.

Example 16

Synthesis of (3R,4aS,6aS,11aS,11aS)-7,9-dimethoxy-4,4,6a,11b-tetramethyl-2,3,4,4a,5,6,6a,11,11a,11b-decahydro-1H-benzo[a]fluoren-3-yl ester (2S)-3,3,3-trifluoro-2-methoxy-2-phenylpropanoate (10a)

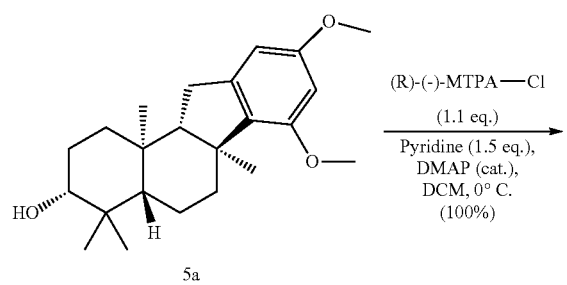

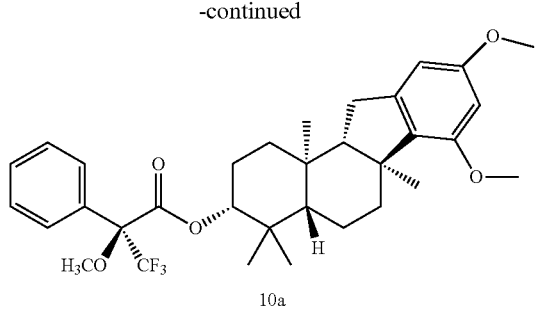

Compound 5a (219 mg, 0.610 mmol) was converted quantitatively to 10a using the method of Example 7. $^1$H NMR (400 MHz, CDCl$_3$) δ 7.57 (m, 2H), 7.41 (t, 3H), 6.41 (s, 1H), 6.26 (d, J=1.5 Hz, 1H), 4.75 (dd, J=10, 6.0 Hz, 1H), 3.77 (s, 3H), 3.75 (s, 3H), 3.58 (s, 3H), 2.64 (t, J=14 Hz, 1H), 2.52 (dd, J=14, 6.1 Hz, 1H), 2.46 (m, 1H), 1.91-1.79 (m, 2H), 1.75-1.70 (m, 2H), 1.66-1.62 (m, 4H), 1.25 (td, J=13, 5.0 Hz, 1H), 1.08 (s, 3H), 1.07 (s, 3H), 0.86 (s, 3H), 0.83 (s, 3H); $^{13}$C NMR (100 MHz, CDCl$_3$) δ 166.1, 159.5, 155.8, 144.7, 133.2, 132.7, 129.5, 128.3, 127.3, 124.9, 122.1, 101.9, 96.9, 84.3, 64.2, 56.2, 55.4 (2C), 55.1, 46.1, 38.1, 38.0, 37.9, 36.5, 29.5, 27.7, 23.4, 20.3, 19.0, 16.2, 15.9. ESIMS [M+Na]$^+$ calcd for $C_{33}H_{41}O_5F_3Na$ 597.2804, found 597.2814. $[\alpha]^{24}_D = -22.87°$.

Example 17

Synthesis of (3R,4aS,6aS,11aS,11aS)-7,9-Dimethoxy-4,4,6a,11b-tetramethyl-2,3,4,4a,5,6,6a,11,11a,11b-decahydro-1H-benzo[a]fluoren-3-yl ester (2R)-3,3,3-trifluoro-2-methoxy-2-phenylpropanoate (10C)

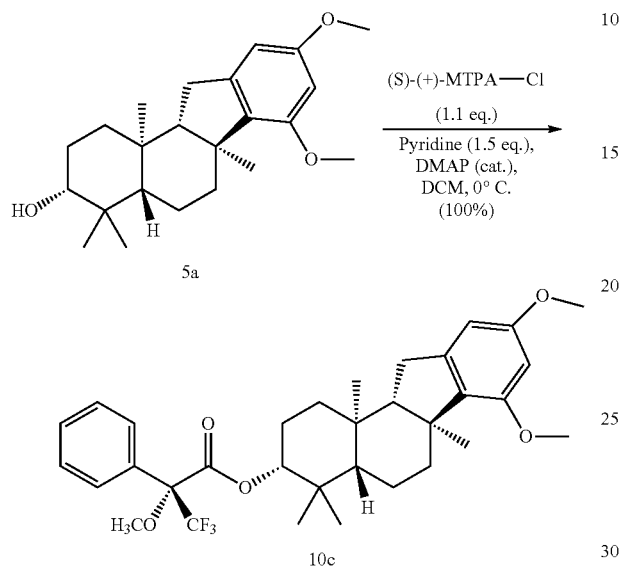

Compound 5a (219 mg, 0.610 mmol) was converted quantitatively to Compound 10c by the method of Example 7 except that (S)-(+)-MTPA-Cl was used. $^1$H NMR (400 MHz, CDCl$_3$) δ 7.55 (m, 2H), 7.42 (t, J=3.0 Hz, 3H), 6.41 (s, 1H), 6.27 (d, J=1.5 Hz, 1H), 4.73 (dd, J=12, 4.8 Hz, 1H), 3.78 (s, 3H), 3.75 (s, 3H), 3.54 (s, 3H), 2.63 (t, J=14 Hz, 1H), 2.52 (dd, J=14.4, 8.3 Hz, 1H)), 2.48 (m, 1H), 1.85-1.77 (m, 2H), 1.75-1.68 (m, 3H), 1.66-1.57 (m, 3H), 1.24 (dt, J=13, 3.8 Hz, 1H), 1.08 (s, 3H), 1.04 (s, 3H), 0.93 (s, 3H), 0.88 (s, 3H); $^{13}$C NMR (100 MHz, CDCl$_3$) δ 166.4, 159.5, 155.8, 144.7, 133.1, 132.4, 129.5, 128.3, 127.6, 124.9, 122.0, 101.9, 96.9, 84.5, 64.2, 56.2, 55.4, 55.3, 55.1, 46.0, 38.1, 38.0, 37.9, 36.5, 29.5, 28.1, 23.0, 20.3, 19.1, 16.2, 16.1. ESIMS [M+Na]$^+$ calcd for C$_{33}$H$_{41}$O$_5$F$_3$Na 597.2804, found 597.2793. [α]$^{24}_D$=+32.29°.

Example 18

Synthesis of (4aS,6aS,11aS,11bS)-3-(hydroxyimio)-4,4,6a,11b-tetramethyl-1H,2H,3H,4H,4aH,5H,6H,6aH,11H,11aH,11bH-cyclohexa[a]fluorene-7,9-diol (11a)

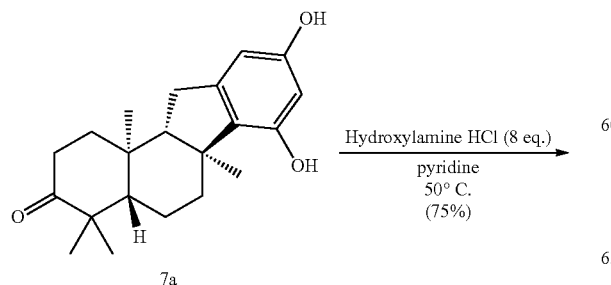

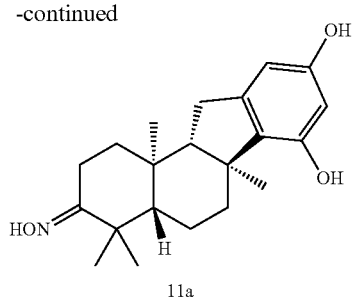

Compound 7a (20 mg, 0.060 mmol) was converted to Compound 11a by the method of Example 8. Compound 11a was obtained as a white solid (15 mg, 0.045 mmol, 75%). $^1$H NMR and $^{13}$C NMR were identical to 11b from Example 8. ESIMS [M+H]$^+$ calcd for C$_{21}$H$_{30}$O$_3$N 344.2226, found 344.2233. [α]$^{24}_D$=+13.18°.

Example 19

Synthesis of (5aS,7aS,12aS,12bS)-8,10-dihydroxy-5,5,7a,12b-tetramethyl-1H,2H,3H,4H,5H,5aH,6H,7H,7aH,12H,12aH,12bH-fluoreno[2,1-C]azepin-3-one (12a) and (5aS,7aS,12aS,12bS)-8,10-dihydroxy-5,5,7a,12b-tetramethyl-1H,2H,3H,4H,5H,5aH,6H,7H,7aH,12H,12aH,12bH-fluoreno[1,2-D]azepin-4-one (13a)

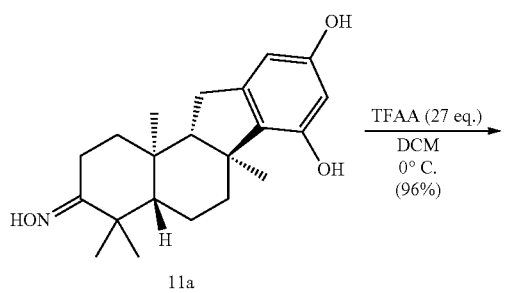

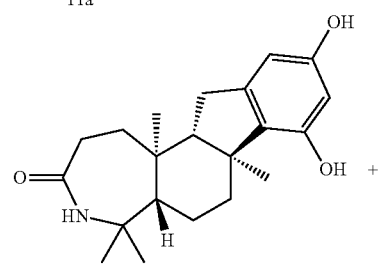

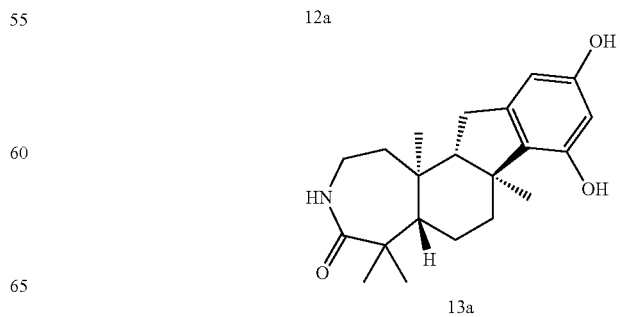

Compound 12a and minor regioisomer 13a were obtained by reaction of 11a (10 mg, 0.029 mmol) using the method of Example 9 yielding 12a and 13a (10 mg, 0.029 mmol, 96%) as a white solid.

Compound 12a: $^1$H NMR and $^{13}$C NMR were identical to 12b from Example 9. ESIMS [M+Na]$^+$ calcd for $C_{21}H_{29}NO_3Na$ 366.2045, found 366.2047. $[\alpha]^{24}_D$=−4.76°.

Compound 13a: $^1$H NMR and $^{13}$C NMR were identical to 13b from Example 9. ESIMS [M+H]$^+$ calcd for $C_{21}H_{30}NO_3$ 344.2226, found 344.2219. $[\alpha]^{24}_D$=+8.7°.

Example 20

Synthesis of (5aR,7aR,12aR,12bR)-5,5,7a,12b-tetramethyl-1H,2H,3H,4H,5H,5aH,6H,7H,7aH,12H,12aH,12bH-fluoreno[2,1-C]azepine-8,10-diol Hydrochloride (14a.HCl)

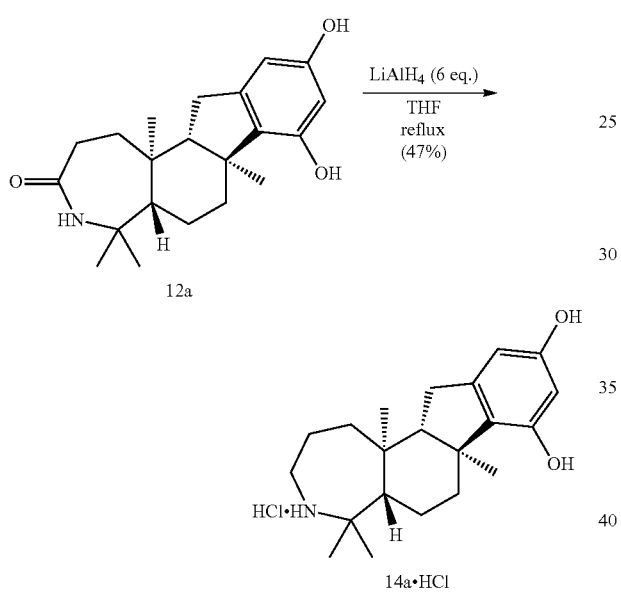

Compound 12a (8.0 mg, 0.023 mmol) was converted to Compound 14a.HCl by the method of Example 10 to provide a white solid (4 mg, 0.01 mmol, 47%). $^1$H NMR and $^{13}$C NMR were identical to 14b.HCl from Example 10. EIMS [M+H]$^+$ calcd for $C_{21}H_{32}NO_2$ 330.2433, found 330.2432. $[\alpha]^{24}_D$=−17.5°.

Example 21

Synthesis of 1,3-Bis-benzyloxy-5-bromobenzene (22)

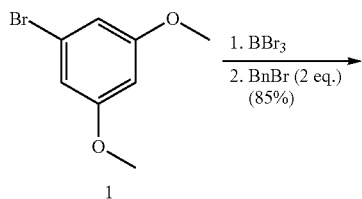

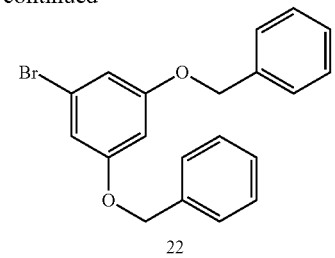

1,3-Dimethoxy-5-bromobenzene (14.5 g, 66.7 mmol) was dissolved in 40 mL $CH_2Cl_2$ and cooled to 0° C. $BBr_3$ (100 mL, 1.0 M in $CH_2Cl_2$, 100 mmol) was added and the solution was stirred for 12 h at room temperature. The reaction was carefully quenched with MeOH and then concentrated to dryness. The resulting syrup was redissolved in EtOAc and was washed with $H_2O$ (3×25 mL). The organic phase was then dried over $Na_2SO_4$, filtered and concentrated to dryness. The residue was then dissolved in DMF (50 mL) and $K_2CO_3$ (20.2 g, 146.7 mmol) was added, followed by benzyl bromide (BnBr, 17.4 mL, 146.7 mmol). The reaction mixture was stirred for 3 h after which TLC analysis (60% EtOAc/hexanes) indicated that the reaction was complete. The reaction mixture was then diluted in EtOAc and washed with water (3×50 mL). The organic phase was dried over $Na_2SO_4$, filtered and concentrated to yield the crude product. The product was crystallized from isopropanol to yield 1,3-bis-Benzyloxy-5-bromobenzene 22 (21 g, 57 mmol, 85° A) yield) as a white powder. $^1$H NMR ($CD_2Cl_2$) δ 7.3-7.5 (m, 10H), 6.71 (s, 2H), 6.60 (s, 1H), 5.05 (s, 4H); $^{13}$C NMR ($CD_2Cl_2$) δ 161.2, 137.2, 128.9, 128.4, 127.8, 123.1, 111.0, 101.5, 70.0.

Example 22

Synthesis of (3S,4aR,6aR,11aR,11bR)-2,3,4,4a,5,6,6a,11,11a,11b-decahydro-4,4,6a,11b-tetramethyl-1H-benzo[a]fluorene-3,7,9-triol (16b)

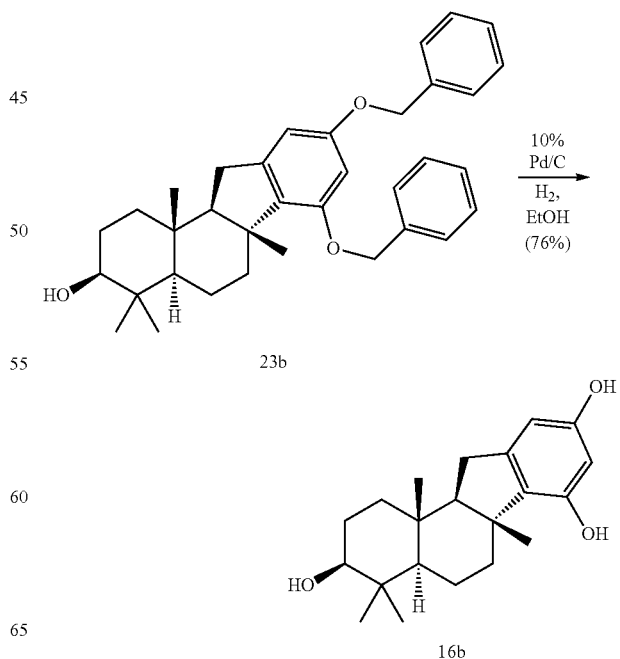

Compound 23b was prepared from compound 22 according to the procedures described above. Compound 23b (51.7 mg, 0.101 mmol) was dissolved in 1 mL ethanol (EtOH), and to this solution was added 10% Pd/C (20 mg). The reaction mixture was then exposed to $H_2$ under balloon pressure for 24 hours after which time the mixture was filtered through filter paper and washed with ethyl acetate (25 mL). The crude mixture was purified by flash chromatography (1:1 hexanes: ethyl acetate, $R_f$=0.30) to give 25.4 mg (76% yield) of compound 16b. Racemic mixtures and/or other stereoisomers (e.g., compound 16a) can also be prepared using analogous procedures.

Example 23

Synthesis of 1-methoxy-3-methyl-5-[(2E,6E)-3,7,11-trimethyldodeca-2,6,10-trien-1-yl]benzene (24)

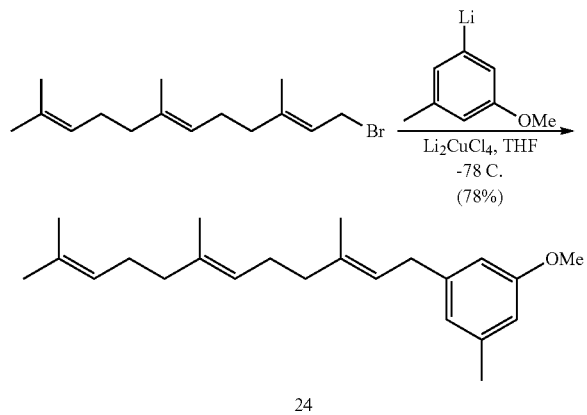

24

To a solution of 3-methoxy-5-bromotoluene (0.50 g, 2.49 mmol) in dry THF (8 mL) was added n-BuLi (1.71 mL, 2.74 mmol, 1.6 M in Hexane) dropwise at −78° C. After the reaction mixture was stirred for 15 min, $Li_2CuCl_4$ (0.1 mL, 0.1 mmol, 0.1 M in THF) was added, and the mixture was stirred for another 10 min at the same temperature. Then, a solution of (E,E)-farnesyl bromide (0.70 mL, 2.58 mmol) in THF (3 ml) was added over 0.5 hour and stirring was continued for 2 hours at −78° C. After the reaction was complete, the mixture was warmed to room temperature and saturated aqueous $NH_4Cl$ (20 mL) was added, followed by 10% $NH_4OH$ (40 mL) and $Et_2O$ (3×50 mL). The combined organic layer was washed with water, brine, and dried with $Na_2SO_4$. The crude product was purified by flash silica gel chromatography (hexanes/EtOAc 60:1, 30:1, 20:1 and 10:1) to yield compound 24 (658.1 mg, 78%) as a colorless oil.

Example 24

Synthesis of 3-((3E,7E)-9-(3-methoxy-5-methylphenyl)-3,7-dimethylnona-3,7-dienyl)-2,2-dimethyloxirane (25)

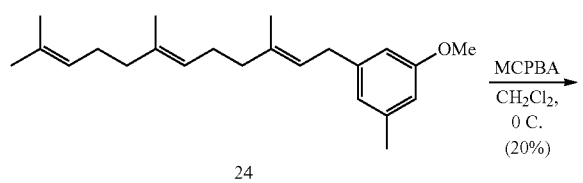

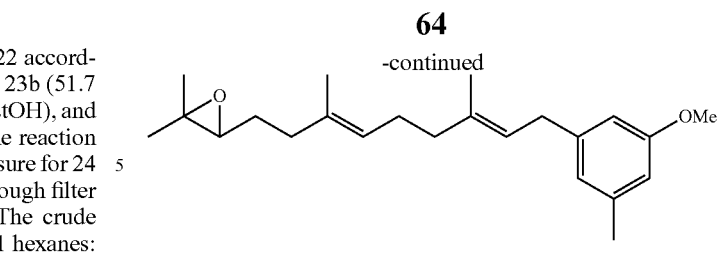

25

To a solution of 24 (488.2 mg, 1.5 mmol) in 12 mL of dry $CH_2Cl_2$ at 0° C. was added a solution of MCPBA (403.4 mg, 1.80 mmol in 4 mL of $CH_2Cl_2$), the reaction mixture was stirred at 0° C. for 1 hr and then quenched with saturated aqueous $NaHCO_3$ (50 mL). $Et_2O$ (3×50 mL) was then added, and the organic layer was washed with saturated aqueous $NaHCO_3$, water, and brine, and dried with $MgSO_4$ and concentrated to give a crude product. The crude product was passed through a silica gel column (hexanes/EtOAc 80:1, 40:1, 20:1) to give the pure epoxide 25 (104 mg: yield 20%) as a colorless oil.

Example 25

Synthesis of (3R,4aS,6aS,11aS,11bS)-9-methoxy-4,4,6a,7,11b-pentamethyl-2,3,4,4a,5,6,6a,11,11a,11b-decahydro-1H-benzo[a]fluoren-3-ol (17a) and (3S,4aR,6aR,11aR,11bR)-9-methoxy-4,4,6a,7,11b-pentamethyl-2,3,4,4a,5,6,6a,11,11a,11b-decahydro-1H-benzo[a]fluoren-3-ol (17b)

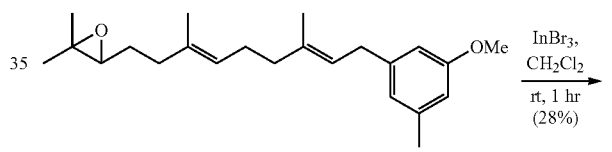

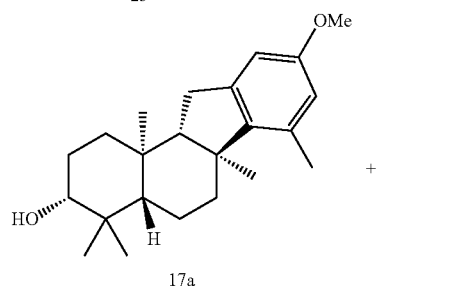

To a solution of 25 (104 mg, 0.31 mmol) in 4 mL of dry $CH_2Cl_2$ was added $InBr_3$ (218.0 mg, 0.62 mmol). The reaction mixture was stirred for 1 hr at room temperature, and quenched with 4 mL of water. The $CH_2Cl_2$ layer was washed with saturated aqueous $NaHCO_3$ followed by brine and dried with MgSO$_4$. After the CH$_2$Cl$_2$ solution was concentrated and dried under high vacuum, the crude product was purified through a silica gel column (hexanes/EtOAc 40:1, 30:1, 20:1, 15:1, 5:1) to give a racemic mixture of 17a and 17b (29.0 mg: yield 28%) as a colorless oil.

Example 26

Synthesis of (4aS,6aS,11aS,11bS)-9-methoxy-4,4,6a, 7,11b-pentamethyl-4,4a,5,6,6a,11,11a,11b-octahydro-1H-benzo[a]fluoren-3(2H)-one (18a) and (4aR, 6aR,11aR,11bR)-9-methoxy-4,4,6a,7,11b-pentamethyl-4,4a,5,6,6a,11,11a,11b-octahydro-1H-benzo[a]fluoren-3(2H)-one (18b)

H$_2$O and brine, concentrated, and dried to give a crude product, which was passed through a silica gel column (hexanes/EtOAc 30:1, 20:1, 10:1) to give a racemic mixture of 18a and 18b (15.5 mg: yield 56%) as a white solid.

Example 27

Synthesis of (4aS,6aS,11aS,11bS)-9-hydroxy-4,4,6a, 7,11b-pentamethyl-4,4a,5,6,6a,11,11a,11b-octahydro-1H-benzo[a]fluoren-3(2H)-one (19a) and (4aR, 6aR,11aR,11bR)-9-hydroxy-4,4,6a,7,11b-pentamethyl-4,4a,5,6,6a,11,11a,11b-octahydro-1H-benzo[a]fluoren-3(2H)-one (19b)

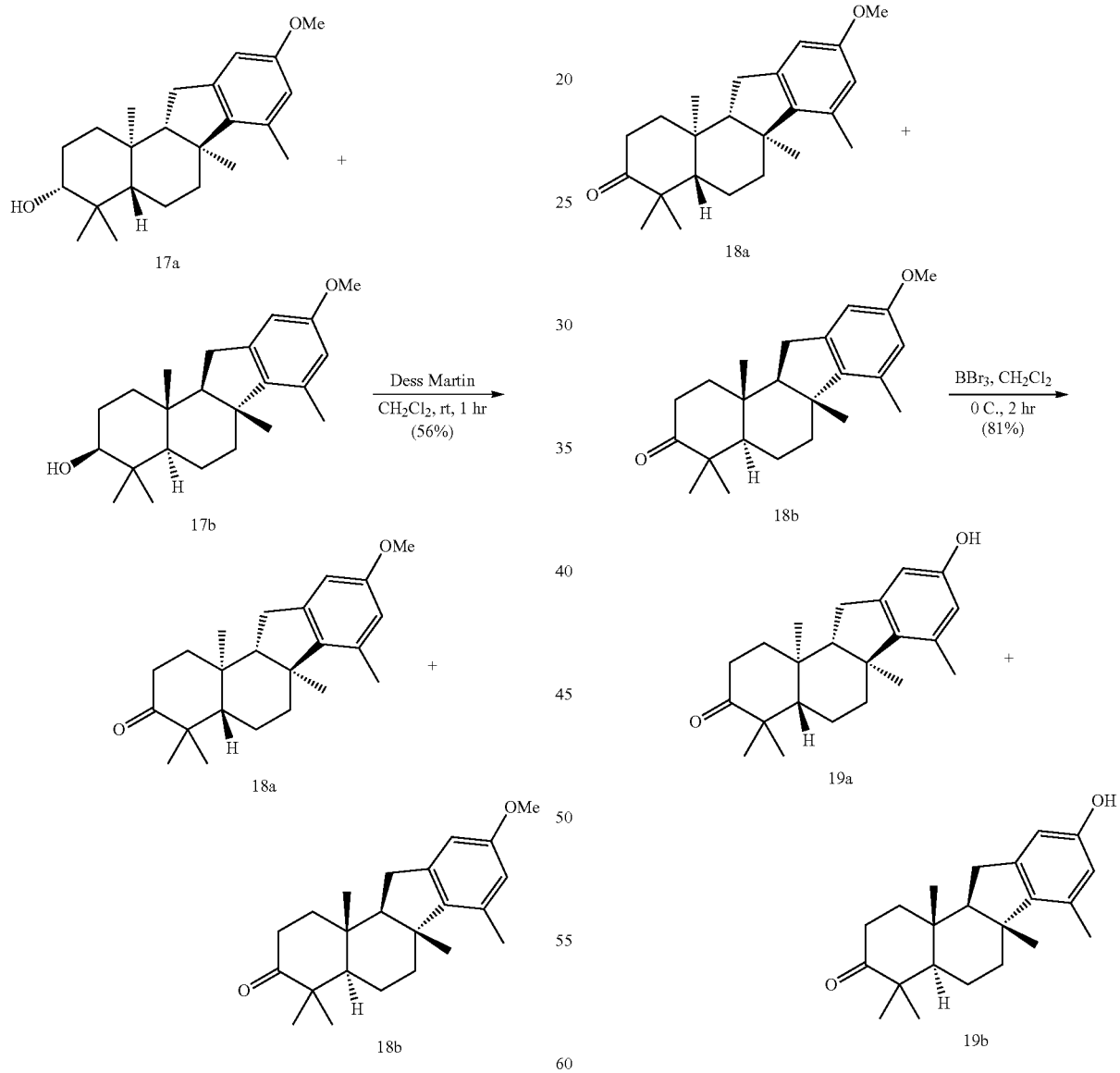

To a solution of a racemic mixture of 17a and 17b (28.0 mg, 0.082 mmol) in 1 mL of dry CH$_2$Cl$_2$ was added Dess-Martin periodinane (70 mg, 0.164 mmol, in 1 mL of dry CH$_2$Cl$_2$). The reaction mixture was stirred at room temperature for 1 hr, diluted with 2 mL of Et$_2$O, and then quenched with saturated aqueous Na$_2$S$_2$O$_3$ (3 mL). The organic layer was washed with To a solution of racemic 18a and 18b (14.5 mg, 0.043 mmol) in 0.5 mL of dry CH$_2$Cl$_2$ was added BBr$_3$ (0.43 mL, 0.43 mmol, 1.0 M in CH$_2$Cl$_2$). The reaction mixture was stirred at 0° C. for 2.5 hr, quenched with 1 mL of ice water, and then diluted with 1 mL of CH$_2$Cl$_2$. The organic layer was washed with saturated aqueous NaHCO$_3$, H$_2$O, and brine, and then concentrated and dried. The crude product was purified on a silica gel Sep-Pak® (2 g) column (hexane/EtOAc 30:1, 20:1, 10:1) to give a racemic mixture of 19a and 19b (11.2 mg: yield 81%) as a white solid.

Example 28

Synthesis of (3R,4aS,6aS,11aS,11bS)-3-amino-4,4,6a,7,11b-pentamethyl-2,3,4,4a,5,6,6a,11,11a,11b-decahydro-1H-benzo[a]fluoren-9-ol (20a), (3S,4aR,6aR,11aR,11bR)-3-Amino-4,4,6a,7,11b-pentamethyl-2,3,4,4a,5,6,6a,11,11a,11b-decahydro-1H-benzo[a]fluoren-9-ol (20b), (3S,4aS,6aS,11aS,11bS)-3-amino-4,4,6a,7,11b-pentamethyl-2,3,4,4a,5,6,6a,11,11a,11b-decahydro-1H-benzo[a]fluoren-9-ol (21a) and (3R,4aR,6aR,11aR,11bR)-3-amino-4,4,6a,7,11b-pentamethyl-2,3,4,4a,5,6,6a,11,11a,11b-decahydro-1H-benzo[a]fluoren-9-ol (21b)

Example 29

His-hSHIP1 Activity of Representative Compounds

Test compounds are dissolved in 95% ethanol to form stock solutions. Before screening, the stock solutions are diluted with Phosphatase Assay Buffer (20 mM Tris-HCL, 10 mM $MgCl_2$ pH 7.5, 0.02% Tween 20) to form working assay solutions that contain 10% ethanol. The assay is carried out on 96-well microtiter plates using a modified procedure of that reported by Ong et al., *Blood* 110, 1942-1949, 2007 and Yang et al., *Org Lett* 7, 1073-1076, 2005, both of which references are incorporated herein by reference in their entirety.

Each reaction contains 5 µL of His-hSHIP1 enzyme (15-20 ng), 10 µL of the substrate, 1,3,4,5-inositol tetrakisphosphate (IP4; 50 µM final), 5 µL of Phosphatase Assay Buffer, and 5 µL of test compound at various concentrations in 10% ethanol (0-300 µM final). Control blanks are also prepared by replacing His-hSHIP1 enzyme, IP4, or test compounds with Phos-

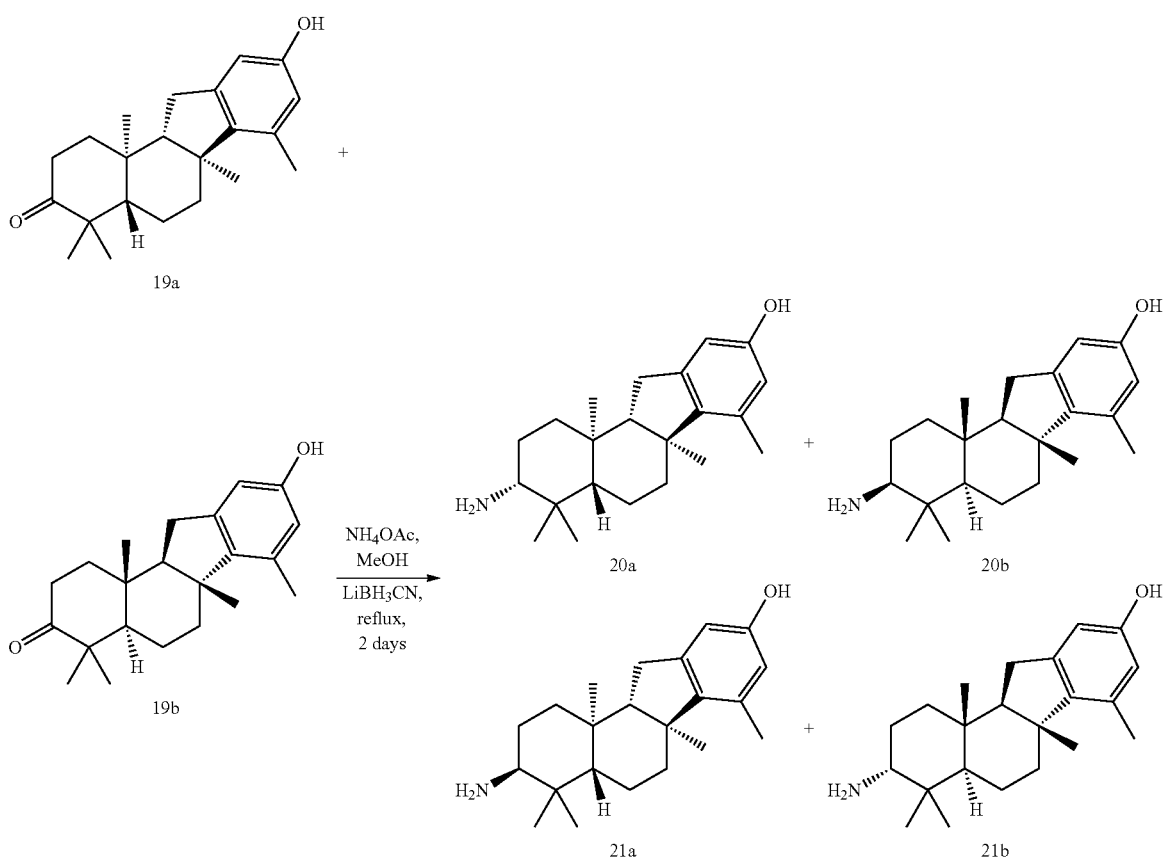

To a solution of 19 (4.5 mg, 0.014 mmol) in 0.9 mL of dry MeOH was added $NH_4OAc$ (11.6 mg, 0.15 mmol) and $LiBH_3CN$ (0.94 mg, 0.015 mmol). The mixture was stirred at 65-70° C. for 2 days. After cooling to room temperature and removal of MeOH, the mixture was dissolved in 1 mL of acidic $H_2O$ (pH<2, with conc. HCl) and partitioned with EtOAc (3×1 mL). The aqueous layer was then basified to pH>10 with KOH and extracted with EtOAc (3×1 mL). The organic layer was concentrated and dried to give a mixture of stereoisomers 20a, 20b, 21a and 21b.

phatase Assay Buffer. After adding the reaction components in a 96-well microtiter plate on ice, the reaction is mixed by briefly shaking the plate vigorously. The reaction is then incubated at 37° C. for 15 min with gentle shaking followed by addition of 100 µL of Biomol Green Reagent (BIOMOL, PA, USA) to terminate the reaction. The free phosphate released from IP4 by His-hSHIP1 binds to the Biomol Green Reagent, which turns the dye to green color. After incubating the mixture for 20 min at room temperature for color development, the absorbance is read with SpectraMax Plus 96-well plate reader (Molecular Devices, Sunnyvale, Calif., USA) at a wavelength of 650 nm.

According to the above assay, the representative compounds listed in Table 2 below were found to activate His-hSHIP1 enzyme at concentrations ≤300 μM. Percent (%) activation in Table 2 is expressed as a percentage increase relative to background. Scoring is expressed as follows: +(<25%); ++(≥25% but <50%); +++(≥50%).

TABLE 2

Activation of His-hSHIP1 Enzyme

| Cpd. No. | Scoring |
|---|---|
| 5a/5b* | ++ |
| 9a•HCl/9b•HCl* | ++ |
| 9b | + |
| 8a•HCl/8b•HCl* | ++ |
| 8a•HCl | + |
| 7a/7b* | +++ |
| 16a/16b* | ++ |
| 17a/17b* | ++ |
| 19a/19b* | ++ |

*Compounds were tested as racemic mixture

Example 30

Activity of Representative Compounds on Akt Phosphorylation in Lymphocytes

Phosphorylation of AKT has been shown to be modulated by SHIP1 (Helgason et al., *J Exp Med* 191, 781-794, 2000). Jurkat (PTEN-/SHIP1-) or Molt-4 (PTEN-/SHIP1+) cells are starved in serum free RPMI for overnight. In a 15 mL conical tube, 2-3 million serum starved cells (1 million cells per mL) are treated with various concentrations of test compound (0.1, 1, or 10 μM final in 0.1% DMSO) for 30 min at 37° C. followed by stimulation with 100 ng/mL of IGF-1 for 1 hour at 37° C. After stimulation, cells are washed once with ice-cold DPBS and lysed with Lysis Buffer (20 mM Tris-HCl, pH 7.5, 140 mM NaCl, 1% NP-40, Complete Mini Protease Inhibitor Cocktail, 10 mM NaF, 1 mM $Na_3VO_4$, 1 mM β-glycerolphosphate) on ice for 30 min with vortexing every 10 min. Samples are then centrifuged at 13,000 rpm for 20 min, and supernatants are collected as total cell lysate samples. Protein concentration is determined using bicinchonic acid assay, and about 15 μg of total protein from each sample is loaded and separated on a 4-12% Tris-Glycine gel. After SDS-PAGE, proteins are transferred from the gel to a nitrocellulose membrane. The membrane is blocked in 5% BSA in PBS containing 0.1% Tween-20 (PBS-T) for 1 hour at room temperature before probing with primary antibodies for overnight at 4° C. The following antibodies are used: mouse anti-SHIP1 (1:500 dilution; Santa Cruz, Calif., USA), rabbit anti-phospho-Akt(Ser473) (1:1000 dilution; Cell Signaling Technologies, MA, USA), rabbit anti-Akt (1:1000; Cell Signaling Technologies, MA, USA), and rabbit anti-actin (1:2000; Cell Signaling Technologies, MA, USA). The membrane is then incubated with goat anti-rabbit or anti-mouse secondary antibodies (1:3000) for 1 hour at room temperature. Target proteins on the membrane are detected with ECL solution and exposed on a film.

According to the above assay, the representative compound listed in Table 3 below was found to inhibit Akt phosphorylation at ≥10 μM in Molt-4 (SHIP1+), but not Jurkat (SHIP1−) lymphocytes. Scoring in Table 4 is expressed as follows: +(inhibits Akt phosphorylation at 10 μM); −(no effect on Akt phosphorylation at 10 μM).

TABLE 3

Inhibition of Akt Phosphorylation

| Cpd. No. | Molt-4 (SHIP +) | Jurkat (SHIP1 −) |
|---|---|---|
| 9a•HCl/9b•HCl* | + | − |

*Compound tested as racemic mixture

Example 31

Activity of Representative Compounds on Passive Cutaneous Anaphylaxis in Mice

The activity of representative compounds on passive cutaneous anaphylaxis in mice was evaluated according to the procedures disclosed by Ovary, *J Immunol* 81, 355-357, 1958 and Halpern et al., *Br J Pharmacol Chemother* 20, 389-398, 1963, both of which are incorporated herein by reference in their entirety.

To induce a passive cutaneous anaphylaxis, mice undergo intradermal ear inoculation on their right ear with 25 ng in 20 μL of anti-DNP-IgE. The left ears are untreated and serve as negative controls. Twenty-four hours after inoculation, all mice are administered test compound by oral gavage (PO). Sixty minutes after oral administration, mice are given a tail vein injection of 2% Evan's Blue (0.2 μM filtered, in 200 μL saline) followed by a second tail IV injection of 100 μg DNP-HSA (in 200 μL). Sixty minutes following the DNP-HAS injection, mice are euthanized using $CO_2$ inhalation. Subsequently, ear biopsies are performed by taking four millimeter punches from both ears, which then undergo Evan's Blue extraction using formamide incubation in 96 well plates. Eighty μL of eluents are transferred to flat-bottom 96-well plates and absorbance read using SpectraMax M5 spectrophotometer (Molecular Devices, Sunnyvale, Calif., USA) at 620 nm. Background readings from all samples are taken at 740 nm and subtracted from the 620 nm readings. Data are reported as OD.

According to the above assay, the representative compound listed in Table 4 below was found to inhibit allergen-induced passive cutaneous anaphylaxis at doses less than 20 mg/kg. Scoring in Table 4 is expressed as follows: + (1-30% inhibition); ++ (31-50% inhibition); +++ (>50% inhibition).

TABLE 4

Inhibition of Allergen-Induced Passive Cutaneous Anaphylaxis

| Cpd. No. | % Inhibition |
|---|---|
| 9a•HCl/9b•HCl* | +++ |

*compound tested as a racemic mixture

Example 32

Water Solubility of Exemplary Compounds

Samples are weighed accurately in duplicate (~3 mg each) in 4 mL glass vials. The appropriate amount of deionized water is added to obtain a final concentration of 6 mg/mL. A stir bar is placed in the vial and the two mixtures are stirred for 24 hours, after which the samples are filtered using a glass filter membrane. The resulting filtrate is centrifuged in a glass conical tube for 10 minutes at 10,000 rpm to sediment any precipitate that may have passed through the glass membrane. The supernatant is sampled for HPLC analysis. The concentration of the test compound is determined by HPLC using a six-point standard curve of the compound prepared in methanol. Data is summarized in Table 5.

TABLE 5

Water Solubility of Exemplary Compounds

| Compound | Soluble Concentration (μg/mL) |
|---|---|
| 8a•HCl | 1397 |
| 16b | 133 |

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A compound having the following structure (I):

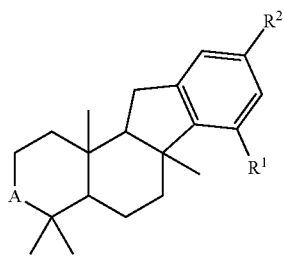

(I)

or a pharmaceutically acceptable salt or stereoisomer thereof, wherein $R^1$ and $R^2$ are each hydroxyl;
A is —CHR$^3$—, —C(R$^4$)(R$^5$)NR$^6$—, —NR$^6$C(R$^4$)(R$^5$)—, —C(=O)— or —C(=N—OR$^6$)—;
$R^3$ is —OR$^6$, —OC(=O)R$^6$ or —NR$^6$R$^7$;
$R^4$ and $R^5$ are each hydrogen or both of $R^4$ and $R^5$ may be taken together to form an oxo moiety; and
$R^6$ and $R^7$ are, at each occurrence, independently hydrogen, alkyl, optionally substituted aryl or optionally substituted aralkyl.

2. The compound of claim 1, wherein A is —CHR$^3$—, and the compound has the following structure (IV):

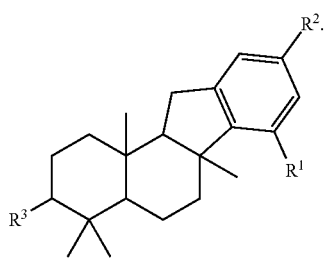

(IV)

3. The compound of claim 2, wherein the compound has one of the following structures (IV-1) or (IV-2):

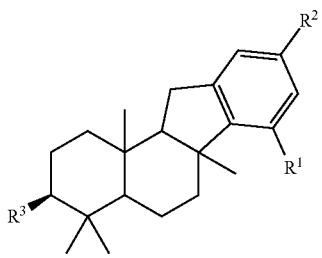

(IV-1)

or

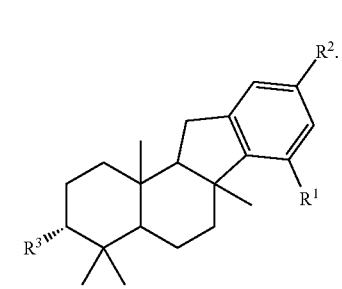

(IV-2)

4. The compound of claim 2, wherein the compound has one of the following structures (IV-3), (IV-4) or (IV-5):

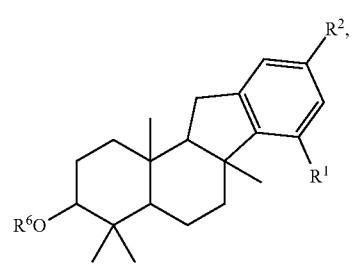

(IV-3)

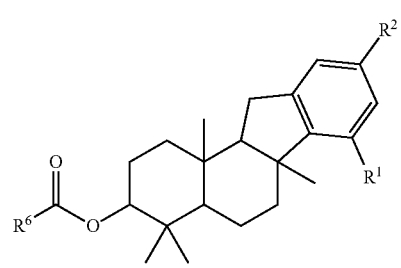

(IV-4)

or

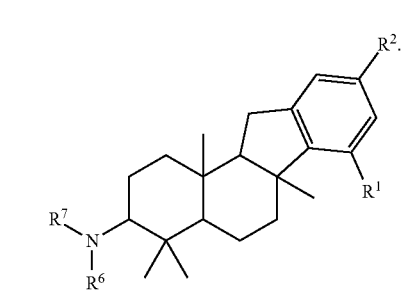

(IV-5)

5. The compound of claim 2, wherein the compound has one of the following structures (IV-6), (IV-7), (IV-8), (IV-9), (IV-10), (IV-11), (IV-12), (IV-13), (IV-14), (IV-15), (IV-16), (IV-17), (IV-18), (IV-19) or (IV-20):

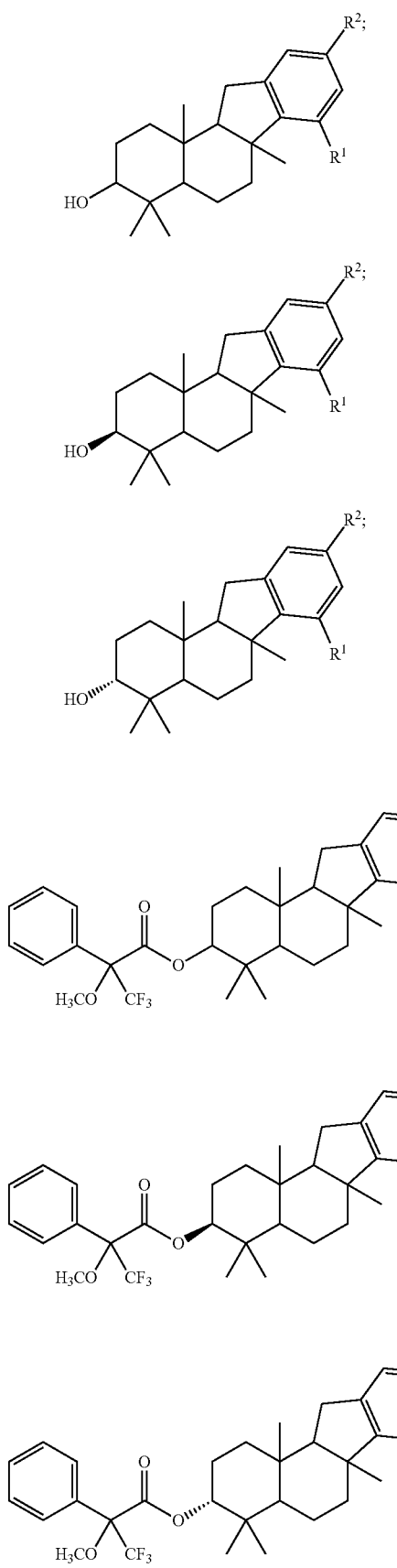
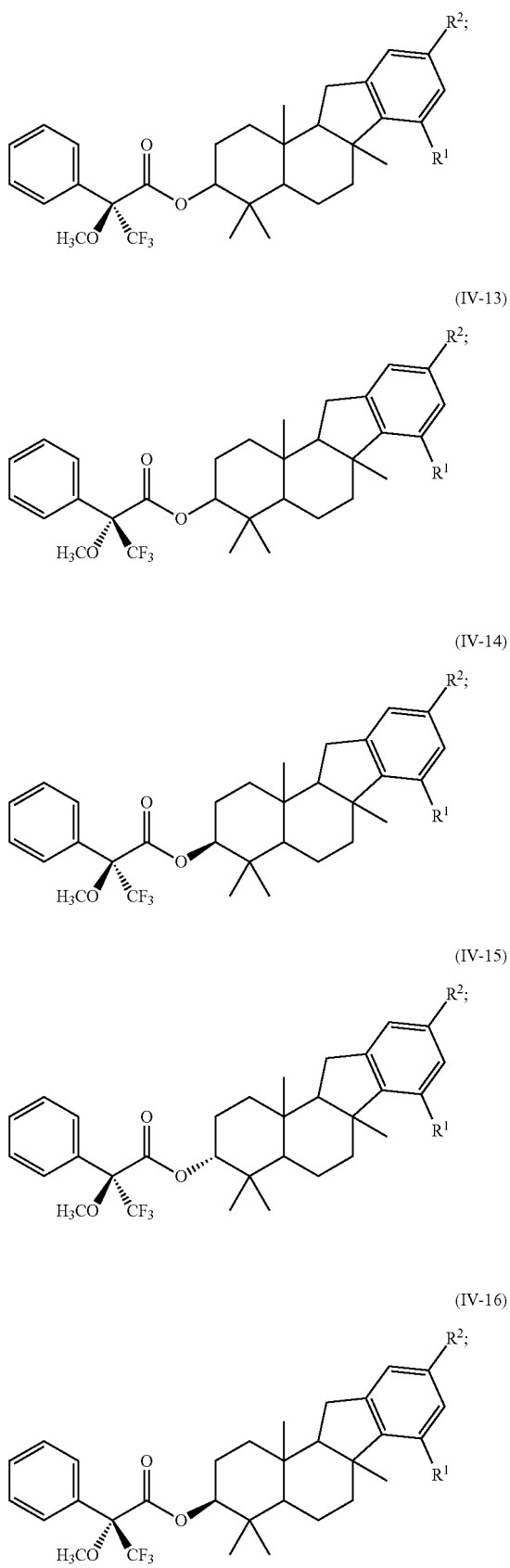

(IV-17)
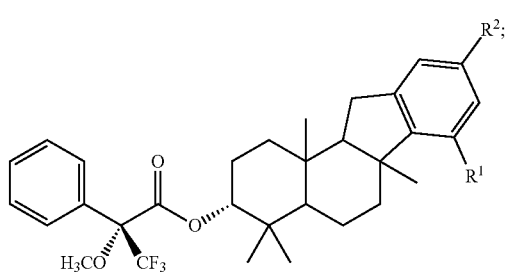

(IV-18)
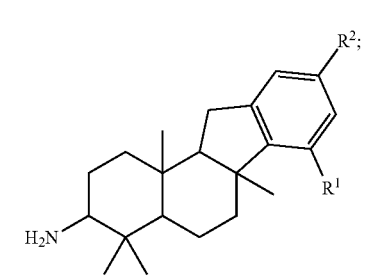

(IV-19)
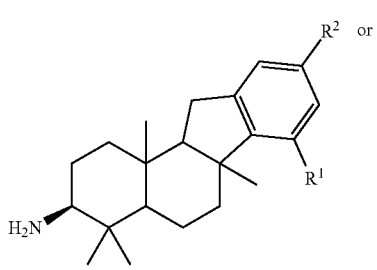

(IV-20)
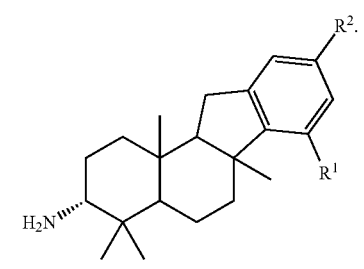

6. The compound of claim 1, wherein A is —C(R⁴)(R⁵)NR⁶— and the compound has the following structure (V):

(V)
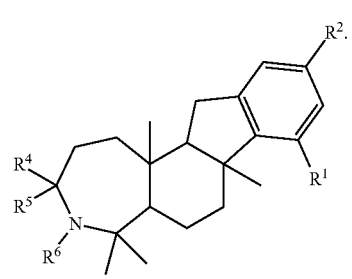

7. The compound of claim 6, wherein the compound has one of the following structures (V-1) or (V-2):

(V-1)

or (V-2)

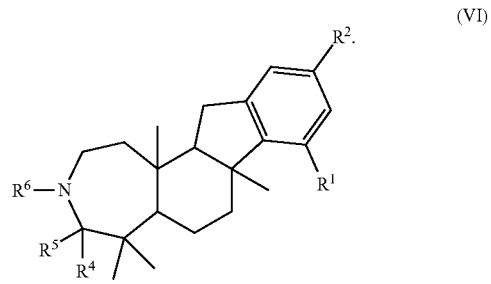

8. The compound of claim 1, wherein A is —NR⁶C(R⁴)(R⁵)— and the compound has the following structure (VI):

(VI)
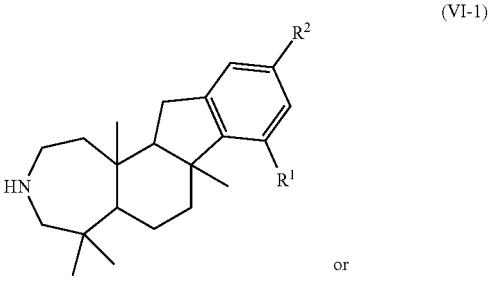

9. The compound of claim 8, wherein the compound has one of the following structures (VI-1) or (VI-2):

(VI-1)

or (VI-2)

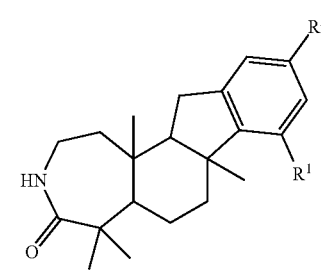

10. The compound of claim 1, wherein A is —C(=O)— and the compound has the following structure (VII):

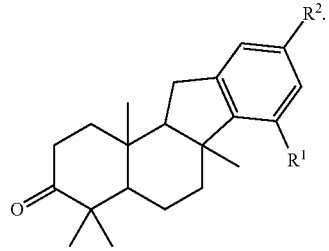
(VII)

11. The compound of claim 1, wherein A is —C(=N—OR⁶)—, and the compound has the following structure (VIII):

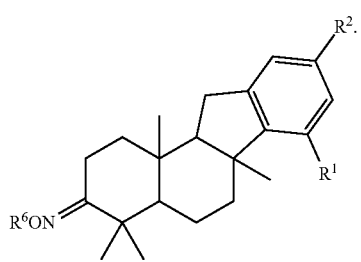
(VIII)

12. The compound of claim 11, wherein the compound has the following structure (VIII-1):

(VIII-1)

13. The compound of claim 1, wherein the compound has one of the following structures (IX) or (X):

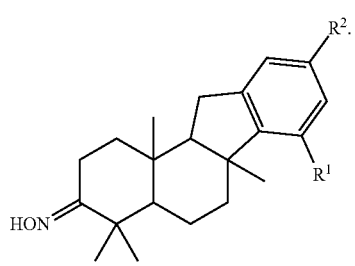
(IX)

or

-continued

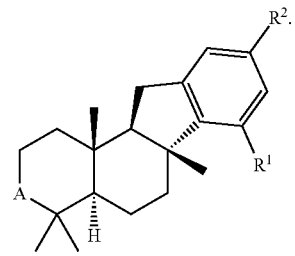
(X)

14. A compound selected from the group consisting of:

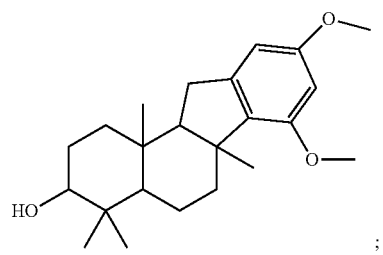
;

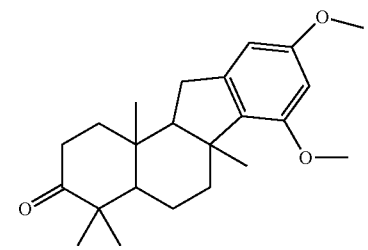
;

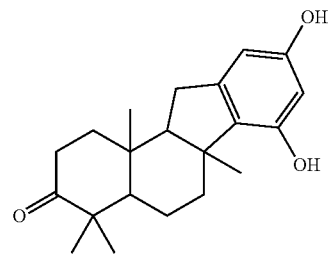
;

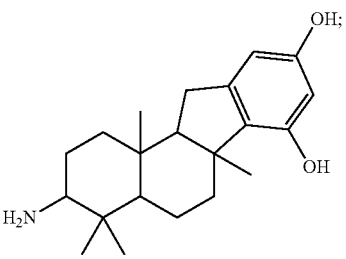
;

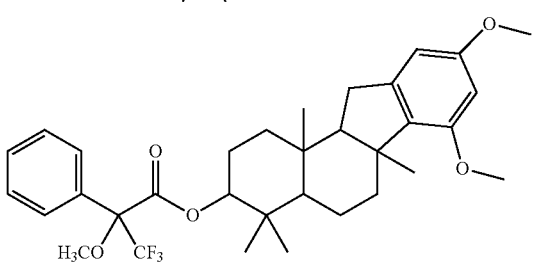
;

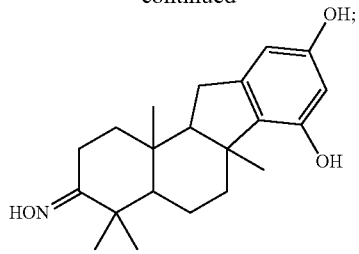
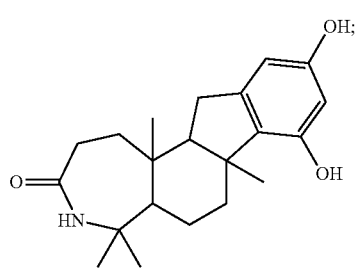
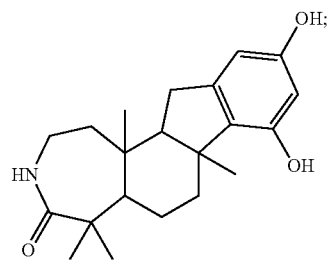
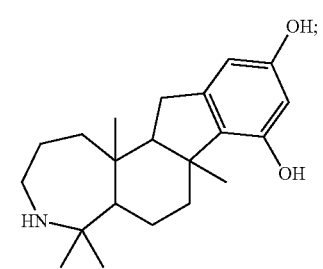
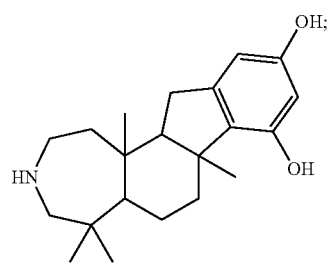
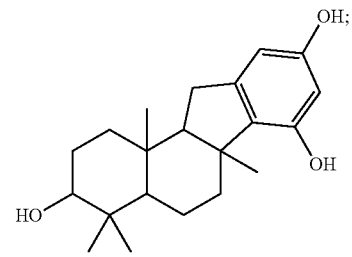
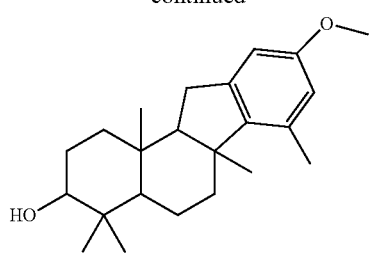
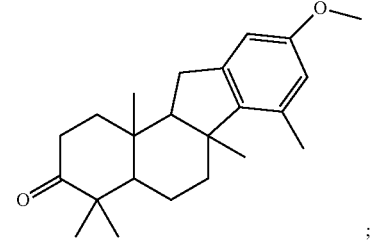
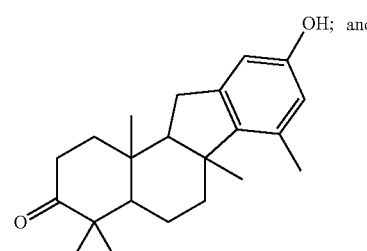
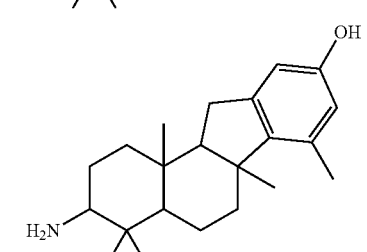
or a pharmaceutically acceptable salt or stereoisomer thereof.
15. A compound according to claim 14 selected from the group consisting of:
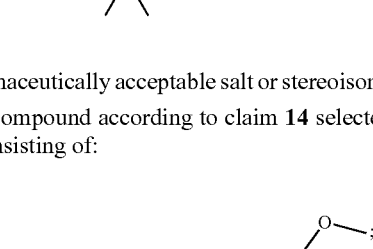
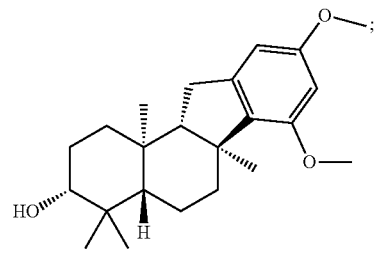

81
-continued
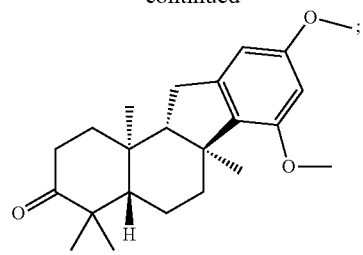
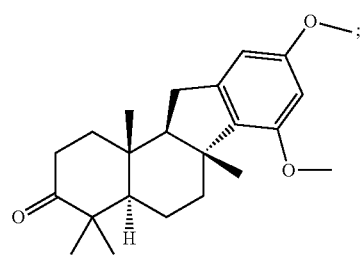
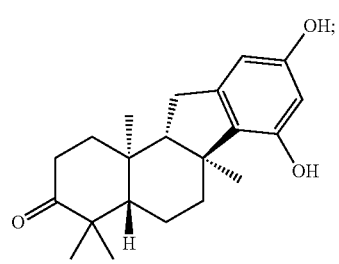
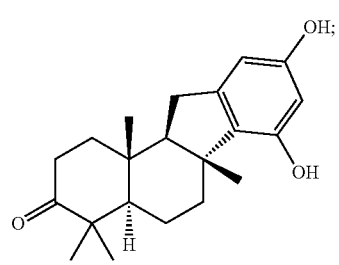
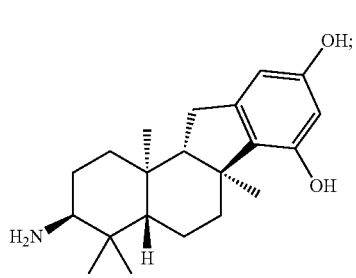
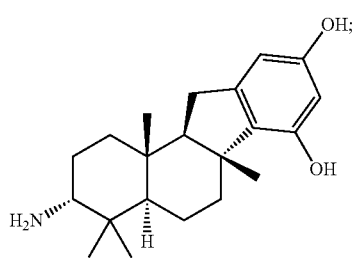
82
-continued
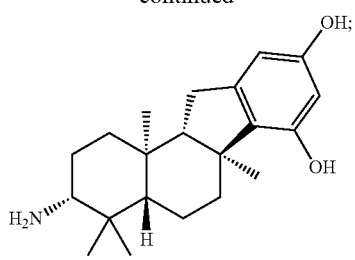
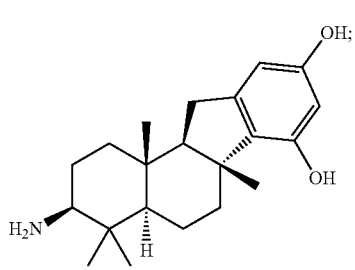
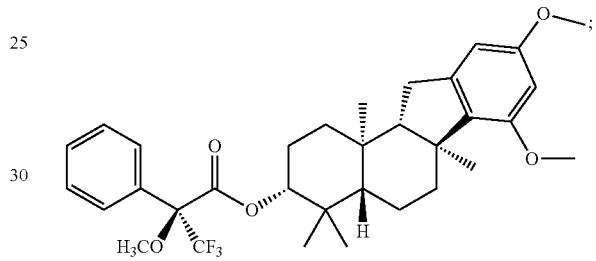
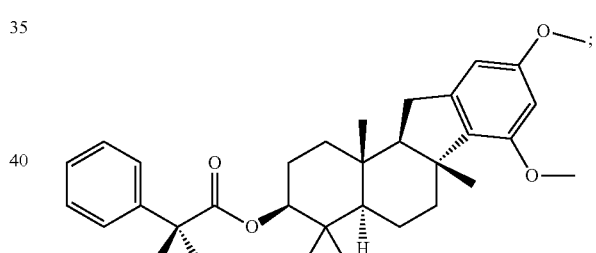
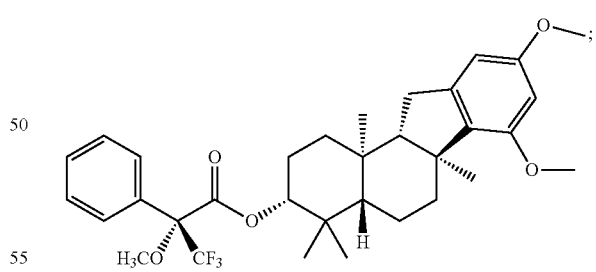
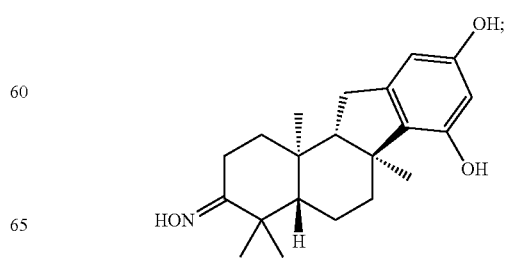

-continued
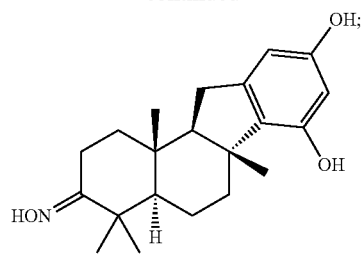
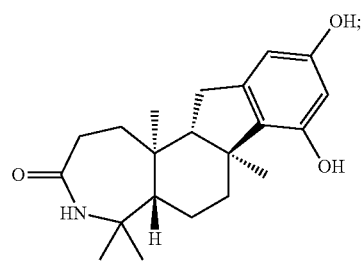
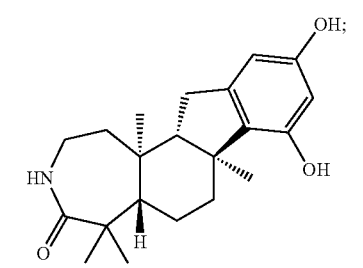
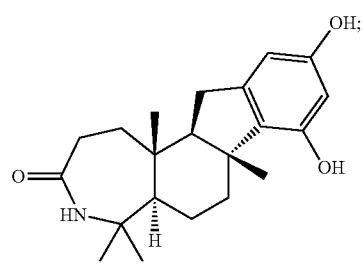
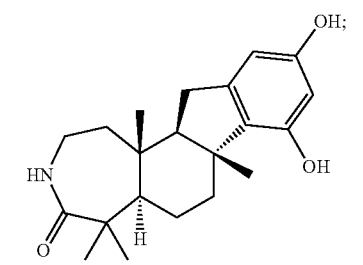
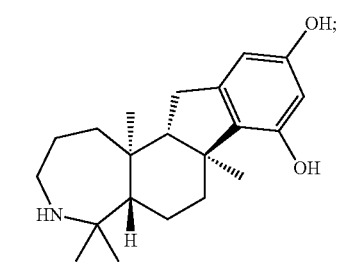
-continued
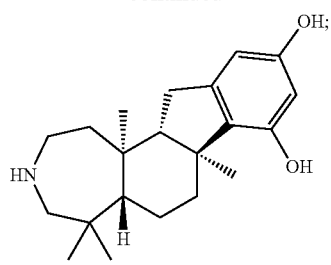
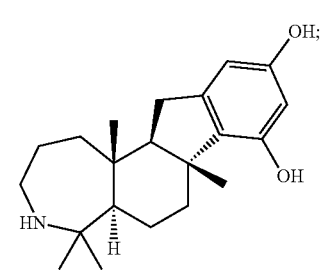
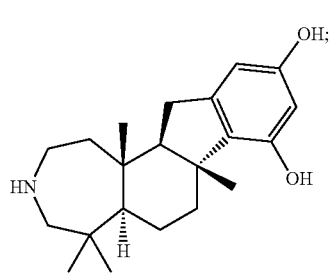
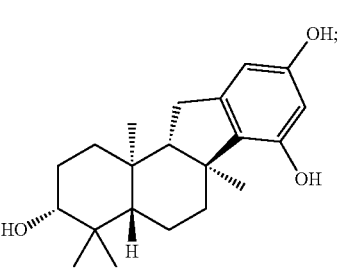
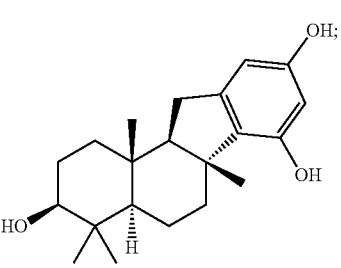
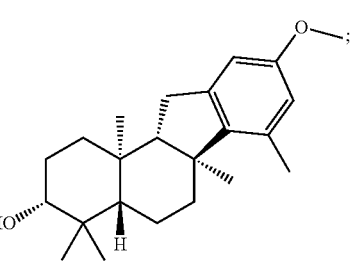

-continued
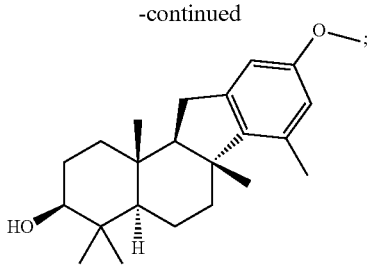
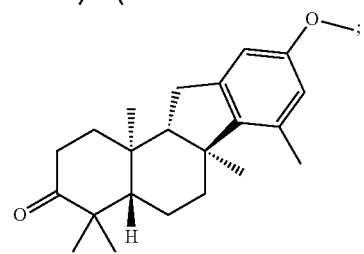
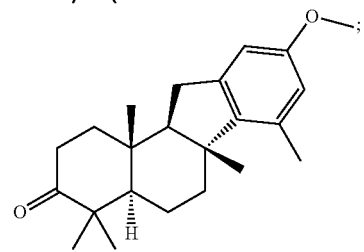
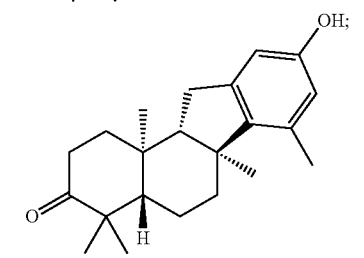
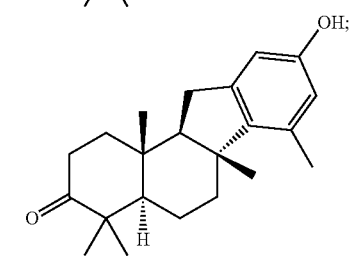
-continued
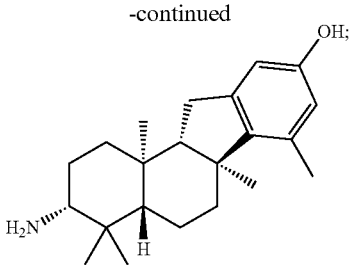
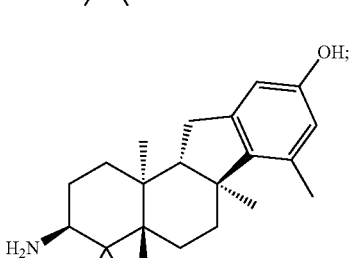
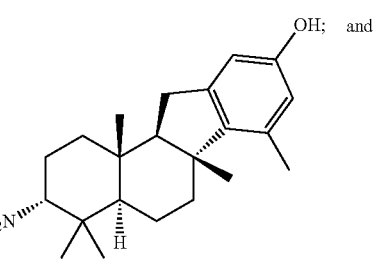
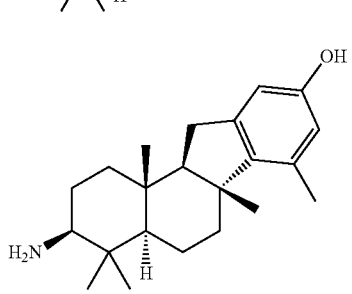
or a pharmaceutically acceptable salt or stereoisomer thereof.
16. A composition comprising a compound of claim 1 in combination with a pharmaceutically acceptable carrier or diluent.
* * * * *